US006900200B2

(12) United States Patent
Failli et al.

(10) Patent No.: US 6,900,200 B2
(45) Date of Patent: May 31, 2005

(54) TRICYCLIC HYDROXY CARBOXAMIDES AND DERIVATIVES THEREOF TOCOLYTIC OXYTOCIN RECEPTOR ANTAGONISTS

(75) Inventors: Amedeo Arturo Failli, Princeton Junction, NJ (US); Jay Scott Shumsky, Hightstown, NJ (US); Thomas Joseph Caggiano, Morrisville, PA (US); Joseph P. Sabatucci, Collegeville, PA (US); Eugene John Trybulski, Princeton Junction, NJ (US); Kevin Anthony Memoli, Cranbury, NJ (US); William Jennings Sanders, Fox Lake, IL (US)

(73) Assignee: Wyeth, Madison, NJ (US)

( * ) Notice: Subject to any disclaimer, the term of this patent is extended or adjusted under 35 U.S.C. 154(b) by 158 days.

(21) Appl. No.: 10/120,100

(22) Filed: Apr. 10, 2002

(65) Prior Publication Data

US 2003/0018026 A1 Jan. 23, 2003

Related U.S. Application Data

(60) Provisional application No. 60/283,261, filed on Apr. 12, 2001.

(51) Int. Cl.$^7$ .................. C07D 487/04; A61K 31/5517; A61P 15/16

(52) U.S. Cl. ........................................ 514/220; 540/561

(58) Field of Search ........................... 514/220; 540/561

(56) References Cited

U.S. PATENT DOCUMENTS

| | | | | |
|---|---|---|---|---|
| 4,766,108 | A | 8/1988 | Ali | |
| 5,055,448 | A | 10/1991 | Manning et al. | |
| 5,070,187 | A | 12/1991 | Gavras et al. | |
| 5,258,510 | A | 11/1993 | Ogawa et al. | |
| 5,436,333 | A | 7/1995 | Venkatesan et al. | |
| 5,459,131 | A | 10/1995 | Albright et al. | |
| 5,466,584 | A | 11/1995 | Tanizawa et al. | |
| 5,512,563 | A | 4/1996 | Albright et al. | |
| 5,516,774 | A | 5/1996 | Albright et al. | |
| 5,521,173 | A | 5/1996 | Venkatesan et al. | |
| 5,532,235 | A | 7/1996 | Albright et al. | |
| 5,536,718 | A | 7/1996 | Albright et al. | |
| 5,609,851 | A | 3/1997 | Bennani | |
| 5,654,297 | A | 8/1997 | Albright et al. | |
| 5,665,719 | A | 9/1997 | Bock et al. | |
| 5,670,509 | A | 9/1997 | Evans et al. | |
| 5,726,172 | A | 3/1998 | Sparks et al. | |
| 5,736,540 | A | 4/1998 | Albright et al. ............ | 514/220 |
| 5,753,644 | A | 5/1998 | Ogawa et al. | |
| 5,756,497 | A | 5/1998 | Bell et al. | |
| 5,756,504 | A | 5/1998 | Bock et al. | |
| 5,780,471 | A | 7/1998 | Venkatesan et al. | |
| 5,849,735 | A | 12/1998 | Albright et al. | |
| 5,880,122 | A | 3/1999 | Trybulski et al. | |
| 5,968,930 | A | 10/1999 | Albright et al. ............ | 514/220 |
| 6,268,359 | B1 | 7/2001 | Ogawa et al. | |
| 6,340,678 | B1 | 1/2002 | Matsuhisa et al. | |
| 2002/0183311 | A1 * | 12/2002 | Failli et al. ................. | 514/220 |
| 2002/0198196 | A1 | 12/2002 | Failli et al. ................. | 514/220 |
| 2003/0004159 | A1 | 1/2003 | Failli et al. ................. | 514/220 |
| 2003/0008863 | A1 | 1/2003 | Failli et al. ................. | 514/220 |
| 2003/0027815 | A1 | 2/2003 | Failli et al. ................. | 514/220 |
| 2003/0055046 | A1 | 3/2003 | Failli et al. ................. | 514/220 |
| 2003/0055047 | A1 | 3/2003 | Failli et al. ................. | 514/220 |

FOREIGN PATENT DOCUMENTS

| | | |
|---|---|---|
| EP | 0 382 185 | 8/1990 |
| EP | 0 470 514 | 2/1992 |
| EP | 0 514 667 | 11/1992 |
| EP | 0 533 240 | 3/1993 |
| EP | 0 533 242 | 3/1993 |
| EP | 0 533 243 | 3/1993 |
| EP | 0 533 244 | 3/1993 |
| EP | 0 620 216 | 10/1994 |
| GB | 2 326 410 | 12/1998 |
| GB | 2 326 639 | 12/1998 |
| WO | WO 91/05549 | 5/1991 |
| WO | WO 94/01113 | 1/1994 |
| WO | WO 94/04525 | 3/1994 |
| WO | WO 94/12476 | 6/1994 |
| WO | WO 94/14796 | 7/1994 |
| WO | WO 94/20473 | 9/1994 |
| WO | WO 96/09824 | 4/1996 |
| WO | WO 96/22282 | 7/1996 |
| WO | WO 96/22292 | 7/1996 |
| WO | WO 96/22294 | 7/1996 |
| WO | WO 96/22775 | 8/1996 |
| WO | WO 97/25992 | 7/1997 |
| WO | WO 98/20011 | 5/1998 |
| WO | 98/20011 | 5/1998 |
| WO | 0 636 625 B1 | 1/1999 |
| WO | WO 99/06409 | 2/1999 |
| WO | WO 99/24051 | 5/1999 |

OTHER PUBLICATIONS

Wolff, Manfred E. "Burger's Medicinal Chemistry, 5ed, Part I", John Wiley & Sons, 1995, pp. 975–977.*

Banker, G.S. et al, "Modern Pharmaceutics, 3ed.", Marcel Dekker, New York, 1996, p. 596.*

(Continued)

*Primary Examiner*—Mark L Berch
*Assistant Examiner*—Thomas McKenzie
(74) *Attorney, Agent, or Firm*—Woodcock Washburn LLP

(57) ABSTRACT

This invention provides novel substituted tricyclic carboxamides which act as oxytocin receptor competitive antagonists, as well as methods of their manufacture, pharmaceutical compositions and methods of their use in treatment, inhibition, suppression or prevention of preterm labor, dysmenorrhea and endometritis, suppression of labor at term prior to caesarean delivery, and to facilitate antinatal transport to a medical facility. These compounds are also useful in enhancing fertility rates, enhancing survival rates and synchronizing estrus in farm animals; and may be useful in the prevention and treatment of disfunctions of the oxytocin system in the central nervous system including obsessive compulsive disorder (OCD) and neuropsychiatric disorders.

15 Claims, No Drawings

OTHER PUBLICATIONS

PubMed Abstract 12848639, also cited as Acta Obstet Gynecol, 2003, 82(8), 687–704.
PubMed Abstract 12436949, also cited as Prog Brain Res, 2002, 139, 359–65.
PubMed Abstract 9891619, also cited as Clin Perinatol, 1998, 25(4), 859–71.
Mats Akerlund, Acta Obstet. Gynecol. Scand., 1987, 459–461, 66.
Mats Akerlund, Reg. Pept., 1993, 187–191, 45.
Ian M. Bell et al., J. Med. Chem., 1998, 2146–2163, 41.
Ya Li Chen et al., Eur. J. Pharmacol., 1999, 25–51, 376.
J.J. Evans et al., J. Endocrinol., 1989, 107–116, 122.
Ben E. Evans et al., J. Med. Chem., 1993, 3993–4006, 36.
Ben E. Evans et al., J. Med. Chem., 1992, 3919–3927, 35.
Anna–Riitta Fuchs et al., Science, 1982, 1396–1398, 215.
Andre Giroux et al., Tetr. Lett., 1997, 3841–3844, 38.
T. Murphy Goodwin et al., Obstet. Gynecol., 1996, 331–336, 88.
Aleksandar Jovanovic et al., Br. J. Pharmacol., 1997, 1468–1474, 12.
Mario Maggi et al., J. Clin. Endocrinol. Metab., 1990, 1142–1154, 70.
A. Okano, J. Reprod. Dev., 1996, 67–70, 42 (Suppl.).
D.J. Pettibone et al., Biochem. Soc. Trans., 1997, 1051–1057, 25(3).
V. Rettori et al., Proc. Nat. Acad. Sci. U.S.A., 1997, 2741–2744, 94.
G. Robinson et al., J. Endocrinol., 1990, 425–432, 125.
Olga Wellnitz et al., J. Dairy Res., 1999, 1–8, 66.
Gabor L. Kovacs et al., Psychoneuroendocrinology, 1998, 945–962, 23(8).
Margaret M. McCarthy et al., Molecular Medicine Today, 1997, 269–275, 3(6).
James. F. Leckman et al., Psychoeuroendocrinology, 1994, 723–749, 19(8).

* cited by examiner

TRICYCLIC HYDROXY CARBOXAMIDES AND DERIVATIVES THEREOF TOCOLYTIC OXYTOCIN RECEPTOR ANTAGONISTS

This application claims priority from provisional application Ser. No. 60/283,261, filed Apr. 12, 2001, the entire disclosure of which is hereby incorporated by reference.

This invention concerns novel substituted tricyclic carboxamides which act as oxytocin receptor competitive antagonists, as well as methods of their manufacture, methods of treatment and pharmaceutical compositions utilizing these compounds. The compounds of the present invention are useful therapeutic agents in mammals, particularly in humans. More specifically, they can be used in the treatment and/or prevention and/or suppression of preterm labor and dysmenorrhea, for the suppression of labor at term prior to caesarean delivery, and to facilitate antinatal transport to a medical facility. These compounds are also useful in enhancing fertility rates, enhancing survival rates and synchronizing estrus in farm animals; and may be useful in the prevention and treatment of disfunctions of the oxytocin system in the central nervous system including obsessive compulsive disorder (OCD) and neuropsychiatric disorders.

BACKGROUND OF THE INVENTION

Premature labor remains the leading cause of perinatal mortality and morbidity. Infant mortality dramatically decreases with increased gestational age. The survival rate of prematurely born infants increases from 20% at 24 weeks to 94% at 30 weeks. Moreover the cost associated with the care of an infant born prematurely is extremely high. While many agents have been developed for the treatment of premature labor in the last 40 years, the incidence of pre-term births and low birth weight infants has remained relatively unchanged. Therefore there remains an unmet need for the development of a safe and effective treatment of preterm labor.

Tocolytic (uterine relaxing) agents currently in use include $\beta_2$ adrenergic receptor agonists such as Ritodrine which is moderately effective in suppressing preterm labor, but it is associated with maternal hypotension, tachycardia, and metabolic side effects. Several other agents have been used to suppress premature labor, including other $\beta_2$ adrenergic agonists (terbutaline, albuterol), magnesium sulfate, NSAIDs (indomethacin), and calcium channel blockers. The consensus is that none of these agents are very effective; there is no clinical evidence showing that these compounds can prolong gestation for more than 7 days (Johnson, *Drugs*, 45, 684–692 (1993)). Furthermore, their safety profile is not ideal. Adverse effects include respiratory depression and cardiac arrest (magnesium sulfate), hemodynamic effects (calcium channel blockers), premature closure of the ductus arteriosus and oligohydramnios (NSAIDs; prostaglandin synthase inhibitors). Therefore, there is an unmet need for safer and more efficacious agents for the treatment of preterm labor with better patient tolerability. Specific requirements with regard to safety include a product with no or low rates of tachycardia, limited anxiety, improved fetal safety, and few, if any, adverse cardiovascular effects.

One target of interest is the oxytocin receptor in the uterus, and a selective oxytocin receptor antagonist has been proposed as an ideal tocolytic agent. While the exact role of oxytocin (OT) in parturition has not been clearly defined, there is evidence strongly suggesting that it may play a critical role in the initiation and progression of labor in humans (Fuchs et al. *Science* 215, 1396–1398 (1982); Maggi et al. *J. Clin. Endocrinol. Metab.* 70, 1142–1154 (1990); Akerlund, *Reg. Pept.* 45,187–191 (1993); Akerlund, Int. Congr. Symp. Semin. Ser., *Progress in Endocrinology* 3, 657–660 (1993); Akerlund et al., in *Oxytocin*, Ed. R. Ivell and J. Russel, Plenum Press, New York, pp 595–600 (1995)). Preliminary clinical trials with oxytocin receptor antagonists support the concept that a blockade of OT receptors reduces uterine myometrial activity and delays the onset of labor (Akerlund et al., *Br. J. Obst. Gynaecol.* 94, 1040–1044, (1987); Andersen et al., *Am. J. Perinatol.* 6, 196–199 (1989); Melin, *Reg. Pept.* 45, 285–288 (1993)). Thus, a selective oxytocin antagonist is expected to block the major effects of oxytocin exerted mainly on the uterus at term, and to be more efficacious than current therapies for the treatment of preterm labor. By virtue of its direct action on the receptors in the uterus an oxytocin antagonist is also expected to have fewer side effects and an improved safety profile.

The following prior art references describe peptidic oxytocin antagonists: Hruby et al., Structure-Activity Relationships of Neurohypophyseal Peptides, in *The Peptides: Analysis, Synthesis and Biology*, Udenfriend and Meienhofer Eds., Academic Press, New York, Vol. 8, 77–207 (1987); Pettibone et al., *Endocrinology*, 125, 217 (1989); Manning et al., Synthesis and Some Uses of Receptor-Specific Agonists and Antagonists of Vasopressin and Oxytocin, *J. Recept. Res.*, 13, 195–214 (1993); Goodwin et al., Dose Ranging Study of the Oxytocin Antagonist Atosiban in the Treatment of Preterm Labor, *Obstet. Gynecol.*, 88, 331–336 (1996). Peptidic oxytocin antagonists suffer from a lack of oral activity and many of these peptides are non-selective antagonists since they also exhibit vasopressin antagonist activity. Bock et al. [*J. Med. Chem.* 33, 2321 (1990)], Pettibone et al. [*J. Pharm. Exp. Ther.* 256, 304 (1991)], and Williams et al. [*J. Med. Chem.*, 35, 3905 (1992)] have reported on potent hexapeptide oxytocin antagonists which also exhibit weak vasopressin antagonistic activity in binding to $V_1$ and $V_2$ receptors.

Various non-peptidic oxytocin antagonists and/or oxytocin/vasopressin (AVP) antagonists have recently been reported by Pettibone et al., *Endocrinology*, 125, 217 (1989); Yamamura et al., *Science*, 252, 572–574 (1991); Evans et al., *J. Med. Chem.*, 35, 3919–3927 (1992); Pettibone et al., *J. Pharmacol. Exp. Ther*, 264, 308–314 (1992); Ohnishi et al., *J. Clin. Pharmacol.* 33, 230–238, (1993); Evans et al., *J. Med. Chem.* 36, 3993–4006 (1993); Pettibone et al., *Drug Dev. Res.* 30, 129–142 (1993); Freidinger et al., General Strategies in Peptidomimetic Design: Applications to Oxytocin Antagonists, in *Perspect. Med. Chem.* 179–193 (1993), Ed. B. Testa, Verlag, Basel, Switzerland; Serradeil-Legal, *J. Clin. Invest.*, 92, 224–231 (1993); Williams et al., *J. Med. Chem.* 37, 565–571 (1994); Williams et al., *Bioorg. Med. Chem.* 2, 971–985 (1994); Yamamura et al., *Br. J. Pharmacol.*, 105, 546–551 (1995); Pettibone et al., *Advances in Experimental Medicine and Biology* 395, 601–612 (1995); Williams et al., *J. Med. Chem.* 38, 4634–4636 (1995); Hobbs et al., *Biorg. Med. Chem. Lett.* 5, 119 (1995); Williams et al., *Curr. Pharm. Des.* 2, 41–58 (1996); Freidinger et al., *Medicinal Research Reviews*, 17, 1–16 (1997); Pettibone et al., *Biochem. Soc. Trans.* 25 (3), 1051–1057 (1997); Bell et al., *J. Med. Chem.* 41, 2146–2163 (1998); Kuo et al., *Bioorg. Med. Chem. Left.* 8, 3081–3086 (1998); Williams et al., *Biorg. Med. Chem. Left.* 9, 1311–1316 (1999).

Certain carbostyril derivatives and bicyclic azepines are disclosed as oxytocin and vasopressin antagonists by Ogawa et al. in WO 94/01113 (1994); benzoxazinones are disclosed as oxytocin and vasopressin receptor antagonists by Sparks et al. in WO 97/25992 (1997); Williams et al. disclose piperidine oxytocin and vasopressin receptor antagonists in WO 96/22775 (1996); Bock et al. disclose benzoxazinone and benzopyrimidinone piperidines useful as oxytocin and vasopressin receptor antagonists in U.S. Pat. No. 5,665,719 (1997); piperazines and spiropiperidines useful as oxytocin and vasopressin receptor antagonists are disclosed by Evans et al. in U.S. Pat. No. 5,670,509 (1997) and by Bock et al. in U.S. Pat. No. 5,756,504 (1998); Bell et al. disclose piperazine oxytocin receptor antagonists in UK Patent Application, GB 2 326 639 A (1998); Bell et al. disclose benzoxazinone and quinolinone oxytocin and vasopressin receptor antagonists in UK Patent Application GB 2 326 410 A (1998); Bell et al. disclose benzoxazinone oxytocin and vasopressin receptor antagonists in U.S. Pat. No. 5,756,497 (1998); Matsuhisa et al. disclose difluoro tetrahydrobenzazepine derivatives as oxytocin antagonists in WO 98/39325 (1998); Ogawa et al. disclose heterocyclic bisamides with vasopressin and oxytocin antagonist activity in U.S. Pat. No. 5,753,644 (1998); and Ogawa et al. disclose benzazepine derivatives with anti-vasopressin activity, oxytocin antagonistic activity and vasopressin agonist activity, useful as vasopressin antagonists, vasopressin agonists and oxytocin antagonists in WO 97/22591 (1997) and U.S. Pat. No. 6,096,736 (2000).

Trybulski et al. disclose 3-carboxamide derivatives of pyrrolobenzodiazepine bisamides with vasopressin antagonist activity in U.S. Pat. No. 5,880,122 (1999); bicyclic thienoazepines with vasopressin and oxytocin receptor antagonist activity are disclosed by Albright et al. in WO 96/22294 (1996) and U.S. Pat. No. 5,654,297 (1997); and tricyclic benzazepines with vasopressin and oxytocin receptor antagonist activity are disclosed by Albright et al. in U.S. Pat. No. 5,849,735 (1998).

Albright et al. broadly disclose tricyclic benzazepine vasopressin antagonists in WO 96/22282A1 (1996) possessing antagonistic activity at the $V_1$ and/or $V_2$ receptors and which exhibit in vivo vasopressin antagonistic activity, as well as antagonistic activity at the oxytocin receptors.

Venkatesan et al. broadly disclose tricyclic benzazepines with vasopressin and oxytocin antagonist activity in U.S. Pat. No. 5,521,173 (1996), WO 96/22292 (1996), and in U.S.

Compounds which behave as potent oxytocin antagonists by binding with high affinity and selectivity to the oxytocin receptors, thus preventing oxytocin from binding to its receptors and exerting its biological and pharmacologic effects in vivo, can be useful for the treatment and/or prevention and/or suppression of preterm labor, for the suppression of term labor prior to a caesarian delivery, and to facilitate antinatal transport to a medical facility. They can also produce contraception in mammals given that oxytocin antagonists have been shown to inhibit the release of oxytocin-stimulated luteneizing hormone (LH) from pituitary cells (Rettori et al., *Proc. Nat. Acad. Sci. U.S.A*. 94, 2741–2744 (1997); Evans et al., *J. Endocrinol*., 122, 107–116 (1989); Robinson et al., *J. Endocrinol*. 125, 425–432 (1990)).

Oxytocin antagonists further have the ability to relax uterine contractions induced by oxytocin in mammals and thus can be also useful for the treatment of dysmenorrhea, a condition characterized by pain during menstruation (Akerlund, Int. Congr. Symp. Semin. Ser., *Progress in Endocrinology* 3, 657–660 (1993); Akerlund, *Reg. Pept*. 45, 187–191 (1993); Melin, *Reg. Pept*. 45, 285–288 (1993)). Primary dysmenorrhea is associated with ovulatory cycles, and it is the most common complaint of gynecologic patients. Myometrial hypercontractility and decreased blood flow to the uterus are thought to be causative factors for for the symptoms of primary dysmenorrhea (Åkerlund, *Acta Obstet. Gynecol. Scand*. 66, 459–461 (1987). In particular, vasoconstriction of small uterine arteries by vasopressin and oxytocin is thought to produce tissue ischemia and pain (Jovanovic et al., *Br. J. Pharmacol*. 12, 1468–1474 (91997); Chen et al., *Eur. J. Pharmacol*. 376, 25–51 (1999)).

The administration of oxytocin receptor antagonists to farm animals after fertilization has been found to enhance fertility rates by blocking oxytocin induced luteolysis leading to embryonic loss (Hickey et al., WO 96/09824 μl (1996), Sparks et al., WO 97/25992 A1 (1997); Sparks et al., U.S. Pat. No. 5,726,172 A (1998)). Thus, oxytocin receptor antagonists can be useful in farm animal husbandry to control timing of parturition and delivery of newborns resulting in enhanced survival rates. They can also be useful for the synchronization of estrus by preventing oxytocin induced corpus luteum regression and by delaying estrus (Okano, *J. Reprod. Dev*. 42 (Suppl.), 67–70 (1996)). Furthermore oxytocin receptor antagonists have been found to have a powerful effect in inhibiting oxytocin-induced milk ejection in dairy cows (Wellnitz et al., *Journal of Dairy Research* 66, 1–8 (1999)).

Oxytocin is also synthesized in the brain and released in the central nervous system. Recent studies have established the importance of central oxytocin in cognitive, affiliative, sexual and reproductive behavior, and in regulating feeding, grooming and response to stress in animals. Oxytocin may also influence normal behavior in humans. Modulators of oxytocin binding to its receptors in the central nervous system may be useful in the prevention and treatment of disfunctions of the oxytocin system, including obsessive compulsive disorder (OCD) and other neuropsychiatric disorders (Kovacs et al., *Psychoneuroendocrinology* 23, 945–962 (1998); McCarthy et al., *U.K. Mol. Med. Today* 3, 269–275 (1997); Bohus, *Peptidergic Neuron,* [*Int. Symp. Neurosecretion*], $12^{th}$ (1996), 267–277, Publ. Birkhauser, Basel, Switz.; Leckman et al., *Psychoneuroendocrinology* 19, 723–749 (1994)).

Compounds which act to competitively inhibit binding of vasopressin to its receptors are useful in the treatment or prevention of state diseases involving vasopressin disorders in mammals, which include vasodilation and aquaresis (free-water diuresis), treating hypertension and inhibiting platelet aggregation. They are useful in the treatment of congestive heart failure, cirrhosis with ascites, and in the syndrome of inappropriate secretion of antiduretic hormone (SIADH). Furthermore, vasopressin receptor antagonists have been found to be useful in treating disturbances or illnesses of the inner ear, particularly those related to Meniere's disease (Zenner et al., WO 99/24051-A2 (1999)); and for the prevention and treatment of ocular circulatory disorders, particularly intraocular hypertension or glaucoma and vision disorders such as shortsightedness (Ogawa et al., WO 99/38533-Al (1999); Ohtake et al., WO 99/65525 (1999)).

SUMMARY OF THE INVENTION

This invention comprises novel compounds selected from those of Formula (I):

(I)

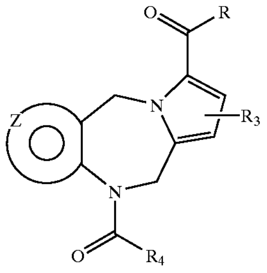

wherein:

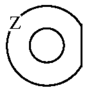

is selected from the moieties:

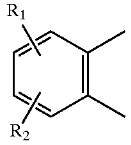
or
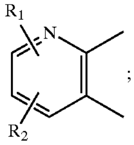
;

$R_1$ and $R_2$ are, independently, selected from hydrogen, $(C_1-C_6)$lower alkyl, halogen, cyano, trifluoromethyl, hydroxy, amino, $(C_1-C_6)$ lower alkylamino, $(C_1-C_6)$ lower alkoxy, $—OCF_3$, $(C_1-C_6)$ lower alkoxycarbonyl, $—NHCO[(C_1-C_6)$lower alkyl], carboxy, $—CONH_2$, $—CONH[(C_1-C_6)$ lower alkyl] or $—CON[(C_1-C_6)$ lower alkyl$]_2$;

$R_3$ is a substituent selected from hydrogen, $(C_1-C_6)$ lower alkyl, $(C_1-C_6)$ lower alkoxy, hydroxy, amino, $(C_1-C_6)$ lower alkylamino, —CO lower alkyl $(C_1-C_6)$, or halogen;

$R_4$ consists of the moiety B—C; wherein:

B is selected from the group consisting of:

(a)

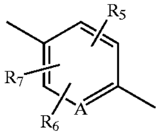

or (b)

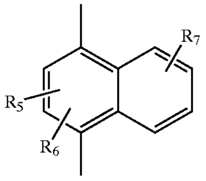

and C is selected from the group consisting of:

(c)

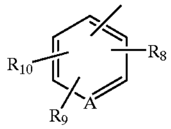

(d)

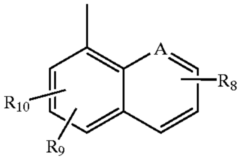

(e)

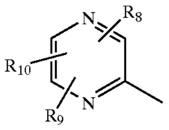

(f)

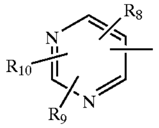

or (g)

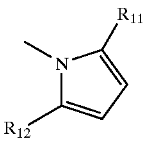

wherein:

A is CH or N;

$R_5$, $R_6$, $R_7$, $R_8$, $R_9$, $R_{10}$ are, independently, selected from hydrogen, $(C_1-C_6)$ lower alkyl, $(C_1-C_6)$ lower alkoxy, hydroxy $(C_1-C_6)$ lower alkyl, alkoxy $(C_1-C_6)$ lower alkyl, acyloxy $(C_1-C_6)$ lower alkyl, $(C_1-C_6)$ lower alkylcarbonyl, $(C_3-C_6)$ lower alkenyl, $(C_3-C_6)$ lower alkynyl, $(C_3-C_8)$ cycloalkyl, formyl, cycloalkylcarbonyl, carboxy, lower alkoxycarbonyl, cycloalkyloxycarbonyl, aryl alkyloxycarbonyl, carbamoyl, $—O—CH_2—CH{=}CH_2$, halogen, halo lower alkyl, trifluoromethyl, $—OCF_3$, $—S[(C_1-C_6)$ lower alkyl], $—OC(O)N[(C_1-C_6)$ lower alkyl$]_2$, $—CONH[(C_1-C_6)$ lower alkyl], $—CON[(C_1-C_6)$ lower alkyl$]_2$, $(C_1-C_6)$ lower alkylamino, di-$[(C_1-C_6)$ lower alkyl]amino, $(C_1-C_6)$ lower alkyl di-$[(C_1-C_6)$ lower alkyl]amino, hydroxy, cyano, trifluoromethylthio, nitro, amino, $(C_1-C_6)$ lower alkylsulfonyl, aminosulfonyl, $(C_1-C_6)$ lower alkylaminosulfonyl,

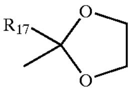
, phenyl or naphthyl;

$R_{11}$ and $R_{12}$ are, independently, selected from the group of hydrogen, $(C_1-C_6)$ lower alkyl, $(C_3-C_6)$ lower alkenyl, $(C_1-C_6)$ lower alkynyl, cyclo lower alkyl, or aryl, optionally substituted by hydroxy, $(C_1-C_6)$ lower alkyl, $(C_1-C_6)$ lower alkoxy, halogen, cyano, $—SO_2[(C_1-C_6)$ lower alkyl], or $—S[(C_1-C_6)$ lower alkyl];

R is selected, independently, from any of the following groups:

(g)

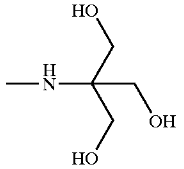

(h)

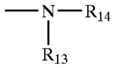

(i)

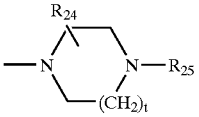

(j)

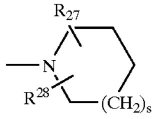

(k)

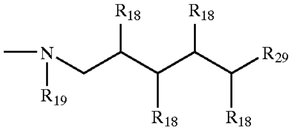

(l)

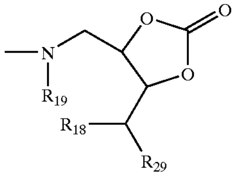

(m)

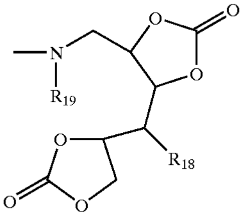

(n)

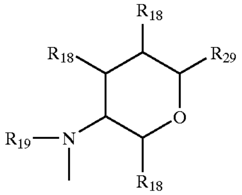

(o)

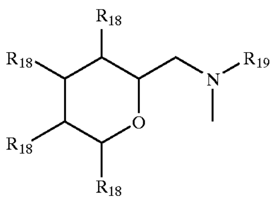 wherein:

wherein:

$R_{13}$ is selected from hydrogen, $(C_1-C_6)$ lower alkyl, $(C_7-C_{12})$ aryl lower alkyl wherein the aryl moiety is optionally substituted with lower alkoxy, or any of the following groups:

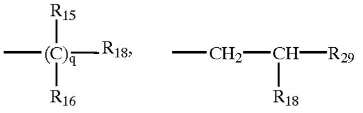 or 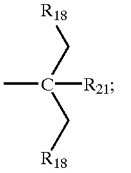

$R_{14}$ is selected from any of the following groups:

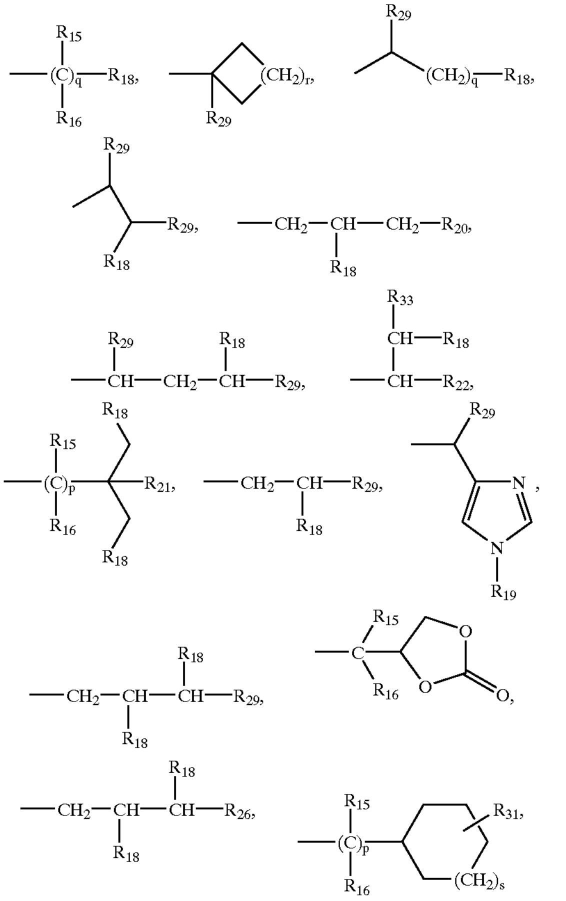

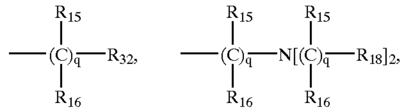 or

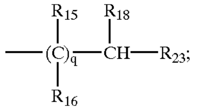

$R_{15}$ and $R_{16}$ are, independently, chosen from the group of hydrogen, $(C_1-C_6)$ lower alkyl or $(C_7-C_{12})$ aryl lower alkyl;

$R_{17}$ is hydrogen, or $(C_1-C_6)$ lower alkyl;

$R_{18}$ is hydroxy, lower alkoxy, or OP wherein P is a hydroxy protecting group, defined as a group providing temporary protection against undesirable reactions during synthetic procedures and to be selectively removable. Common hydroxy protecting groups include, but are not limited to, tert-butyldimethylsilyl, tert-butyldiphenylsilyl, acetyl, trifluoroacetyl, benzyl, benzoyl, methoxymethyl, methylthiomethyl, and others well known in the art (such as those set forth in c.f. Greene et al., *Protective Groups in Organic Syntheses*, 3rd Edn., John Wiley & Sons, New York (1999), the text of which is incorporated herein by reference);

$R_{19}$ is selected from the group of hydrogen, $(C_1–C_6)$ lower alkyl or $(C_7–C_{12})$ aryl lower alkyl;

$R_{20}$ is selected from the group of —N[lower alkyl]$_2$, or —N[aryl lower alkyl]$_2$;

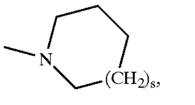

or

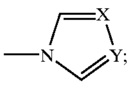

$R_{21}$ is hydrogen, $(C_1–C_6)$ lower alkyl, or $R_{29}$;

$R_{22}$ is selected from the group of $(C_1–C_6)$ lower alkyl, —$COR_{18}$, —CONH[lower alkyl], —CON[lower alkyl]$_2$;

$R_{23}$ is aryl, optionally substituted by one to three substituents chosen from hydroxy, $(C_1–C_6)$ lower alkoxy, aryloxy lower alkyl, or halogen;

$R_{24}$ represents one to four substituents chosen, independently, from the group consisting of hydrogen or $(C_1–C_6)$ lower alkyl;

$R_{25}$ is selected the group consisting of

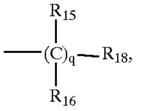

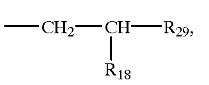

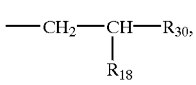

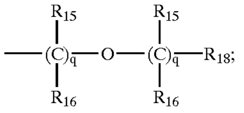

$R_{26}$ is $(C_1–C_6)$ lower alkyl, or aryl $(C_1–C_6)$ lower alkyl;

$R_{27}$ and $R_{28}$ taken together represent one to four substituents chosen, independently, from the group consisting of $R_{18}$, $R_{29}$, $(C_1–C_6)$ lower alkyl , $[(C_1–C_6)$ lower alkyl$]_2$, —CONH[lower alkyl], —CON[lower alkyl]$_2$, $R_{32}$, or

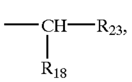

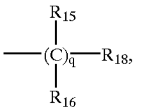

with the proviso that at least one substituent is not $(C_1–C_6)$ lower alkyl, —$[(C_1–C_6)$ lower alkyl$]_2$, —CONH[lower alkyl] or —CON[lower alkyl]$_2$; and with further proviso that $R_{27}$ and $R_{28}$ can be joined together to form a 5 or 6 membered saturated ring optionally substituted by one or more substituents selected from $R_{18}$ or $R_{29}$;

$R_{29}$ is selected from the group of hydroxy lower alkyl, lower alkoxy lower alkyl, or lower alkyl OP wherein P is a hydroxy protecting group, defined as a group providing temporary protection against undesirable reactions during synthetic procedures and to be selectively removable. Common hydroxy protecting groups include, but are not limited to, tert-butyldimethylsilyl, tert-butyldiphenylsilyl, acetyl, trifluoroacetyl, benzyl, benzoyl, methoxymethyl, methylthiomethyl, and others well known in the art (c.f. Greene et al., *Protective Groups in Organic Syntheses*, 3rd Edn., John Wiley & Sons, New York (1999);

$R_{30}$ is $(C_1–C_6)$ lower alkyl, or $(C_7–C_{12})$ aryl lower alkyl;

$R_{31}$ represents one to four substituents chosen from the group of $R_{18}$ or $R_{29}$;

$R_{32}$ is

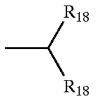

or

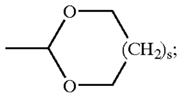

$R_{33}$ is hydrogen or $(C_1–C_6)$ lower alkyl;

X and Y are either CH, or N;

p is an integer from 0 to 1;

q is an integer from 2 to 4;

r is an integer from 0 to 3;

s in integer from 0 to 2 t is an integer from 1 to 2;

and the pharmaceutically acceptable salts, or pro-drug forms thereof.

One group of compounds of this invention comprise those of the formula (II):

(II)

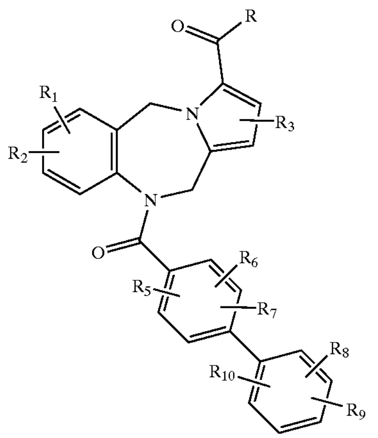

wherein R, $R_1$, $R_2$, $R_3$, $R_5$, $R_6$, $R_7$, $R_8$, $R_9$, $R_{10}$ are as defined above, or a pharmaceutically acceptable salt form thereof.

One preferred group of compounds of this invention are those of the formula:

(I)

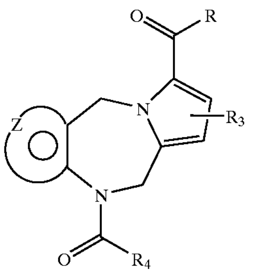

wherein:

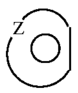

is selected from the moieties:

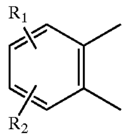 or 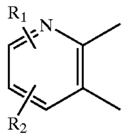 ;

$R_1$ and $R_2$ are, independently, selected from hydrogen, $(C_1–C_6)$lower alkyl, halogen, cyano, trifluoromethyl, hydroxy, amino, $(C_1–C_6)$ lower alkylamino, $(C_1–C_6)$ lower alkoxy, —$OCF_3$, $(C_1–C_6)$ lower alkoxycarbonyl, —NHCO[$(C_1–C_6)$lower alkyl], carboxy, —$CONH_2$, —CONH[$(C_1–C_6)$ lower alkyl] or —CON[$(C_1–C_6)$ lower alkyl$]_2$;

$R_3$ is a substituent selected from hydrogen, $(C_1–C_6)$ lower alkyl, $(C_1–C_6)$ lower alkoxy, hydroxy, amino, $(C_1–C_6)$ lower alkylamino, —CO lower alkyl $(C_1–C_6)$, or halogen;

$R_4$ consists of the moiety B—C; wherein:

B is selected from the group consisting of:

(a)

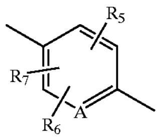 or (b)

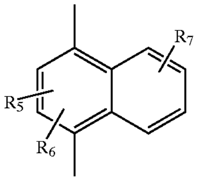

and C is selected from the group consisting of:

(c)

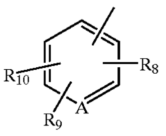

(d)

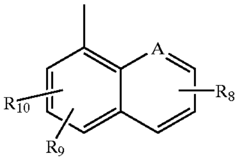

-continued (e)

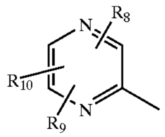

(f)

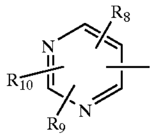 or (g)

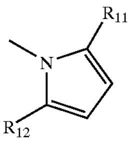

wherein:

A is CH or N;

$R_5$, $R_6$, $R_7$, $R_8$, $R_9$, $R_{10}$ are, independently, selected from hydrogen, $(C_1–C_6)$ lower alkyl, $(C_1–C_6)$ lower alkoxy, hydroxy $(C_1–C_6)$ lower alkyl, alkoxy $(C_1–C_6)$ lower alkyl, acyloxy $(C_1–C_6)$ lower alkyl, $(C_1–C_6)$ lower alkylcarbonyl, $(C_3–C_6)$ lower alkenyl, $(C_3–C_6)$ lower alkynyl, $(C_3–C_8)$ cycloalkyl, formyl, cycloalkylcarbonyl, carboxy, lower alkoxycarbonyl, cycloalkyloxycarbonyl, aryl alkyloxycarbonyl, carbamoyl, —O—$CH_2$—CH═$CH_2$, halogen, halo lower alkyl, trifluoromethyl, —$OCF_3$, —S[$(C_1–C_6)$ lower alkyl], —OC(O)N[$(C_1–C_6)$ lower alkyl$]_2$, —CONH[$(C_1–C_6)$ lower alkyl], —CON[$(C_1–C_6)$ lower alkyl$]_2$, $(C_1–C_6)$ lower alkylamino, di-[$(C_1–C_6)$ lower alkyl]amino, $(C_1–C_6)$ lower alkyl di-[$(C_1–C_6)$ lower alkyl]amino, hydroxy, cyano, trifluoromethylthio, nitro, amino, $(C_1–C_6)$ lower alkylsulfonyl, aminosulfonyl, $(C_1–C_6)$ lower alkylaminosulfonyl,

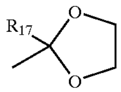, phenyl or naphthyl;

$R_{11}$ and $R_{12}$ are, independently, selected from the group of hydrogen, $(C_1–C_6)$ lower alkyl, $(C_3–C_6)$ lower alkenyl, $(C_1–C_6)$ lower alkynyl, cyclo lower alkyl, or aryl, optionally substituted by hydroxy, $(C_1–C_6)$ lower alkyl, $(C_1–C_6)$ lower alkoxy, halogen, cyano, —$SO_2$[$(C_1–C_6)$ lower alkyl], or —S[$(C_1–C_6)$ lower alkyl];

R is selected, independently, from the groups:

(g)

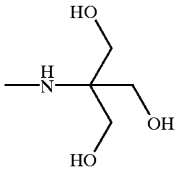

-continued (h)

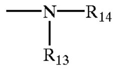

(i)

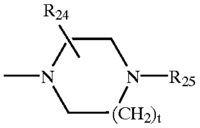

(k)

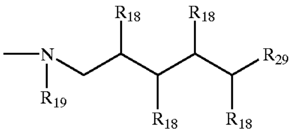

or (m)

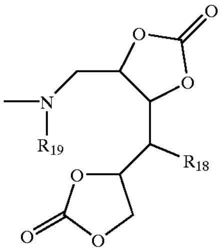

;

$R_{13}$ is selected from hydrogen, ($C_1$–$C_6$) lower alkyl, ($C_7$–$C_{12}$) aryl lower alkyl wherein the aryl moiety is optionally substituted with lower alkoxy, or any of the following groups:

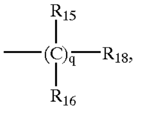

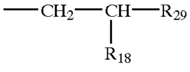

or

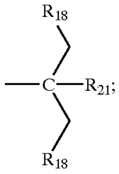

$R_{14}$ is selected from the groups:

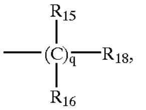

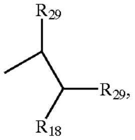

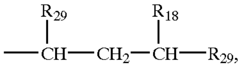

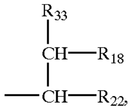

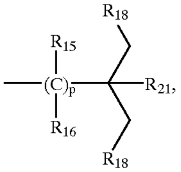

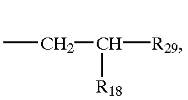

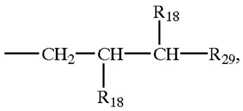

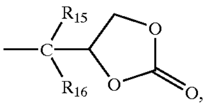

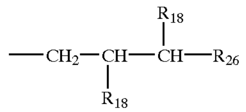

or

-continued

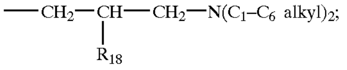

$R_{15}$ and $R_{16}$ are, independently, chosen from the group of hydrogen, ($C_1$–$C_6$) lower alkyl or ($C_7$–$C_{12}$) aryl lower alkyl;

$R_{18}$ is hydroxy, lower alkoxy, or OP wherein P is a hydroxy protecting group, defined as a group providing temporary protection against undesirable reactions during synthetic procedures and to be selectively removable. Common hydroxy protecting groups include, but are not limited to, tert-butyldimethylsilyl, tert-butyldiphenylsilyl, acetyl, trifluoroacetyl, benzyl, benzoyl, methoxymethyl, methylthiomethyl, and others well known in the art (such as those set forth in c.f. Greene et al., *Protective Groups in Organic Syntheses*, 3rd Edn., John Wiley & Sons, New York (1999), the text of which is incorporated herein by reference);

$R_{19}$ is selected from the group of hydrogen, ($C_1$–$C_6$) lower alkyl or ($C_7$–$C_{12}$) aryl lower alkyl;

$R_{21}$ is hydrogen, ($C_1$–$C_6$) lower alkyl, or $R_{29}$;

$R_{25}$ is selected from the groups:

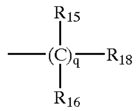

or

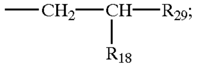

$R_{26}$ is ($C_1$–$C_6$) lower alkyl, or aryl ($C_1$–$C_6$) lower alkyl;

$R_{29}$ is selected from the group of hydroxy lower alkyl, lower alkoxy lower alkyl, or lower alkyl OP wherein P is a hydroxy protecting group, defined as a group providing temporary protection against undesirable reactions during synthetic procedures and to be selectively removable. Common hydroxy protecting groups include, but are not limited to, tert-butyldimethylsilyl, tert-butyldiphenylsilyl, acetyl, trifluoroacetyl, benzyl, benzoyl, methoxymethyl, methylthiomethyl, and others well known in the art (c.f. Greene et al., *Protective Groups in Organic Syntheses*, 3rd Edn., John Wiley & Sons, New York (1999);

p is an integer from 0 to 1;

q is an integer from 2 to 4;

t is an integer from 1 to 2;

or a pharmaceutically acceptable salt or pro-drug form thereof.

A further preferred subgroup of the compounds described above are those of the formula:

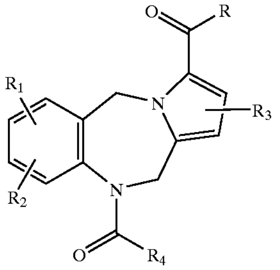

$R_1$ and $R_2$ are, independently, selected from hydrogen, ($C_1$–$C_6$)lower alkyl, halogen, cyano, trifluoromethyl, hydroxy, amino, $(C_1-C_6)$ lower alkylamino, $(C_1-C_6)$ lower alkoxy, $—OCF_3$, $(C_1-C_6)$ lower alkoxycarbonyl, $—NHCO[(C_1-C_6)$lower alkyl], carboxy, $—CONH_2$, $—CONH[(C_1-C_6)$ lower alkyl] or $—CON[(C_1-C_6)$ lower $alkyl]_2$;

$R_3$ is a substituent selected from hydrogen, $(C_1-C_6)$ lower alkyl, $(C_1-C_6)$ lower alkoxy, hydroxy, amino, $(C_1-C_6)$ lower alkylamino, —CO lower alkyl $(C_1-C_6)$, or halogen;

$R_4$ consists of the moiety B—C; wherein:

B is selected from the group consisting of:

(a)

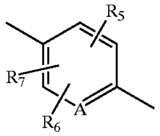

or (b)

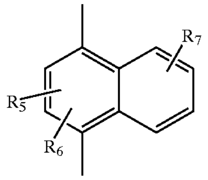

and C is selected from the group consisting of:

(c)

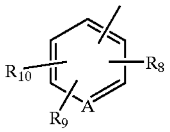

(d)

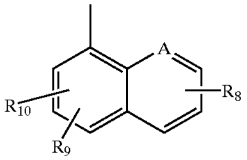

(e)

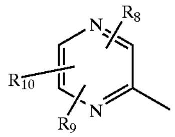

(f)

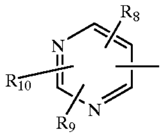

or (g)

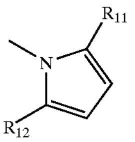

wherein:

A is CH or N;

$R_5$, $R_6$, $R_7$, $R_8$, $R_9$, $R_{10}$ are, independently, selected from hydrogen, $(C_1-C_6)$ lower alkyl, $(C_1-C_6)$ lower alkoxy, hydroxy $(C_1-C_6)$ lower alkyl, alkoxy $(C_1-C_6)$ lower alkyl, acyloxy $(C_1-C_6)$ lower alkyl, $(C_1-C_6)$ lower alkylcarbonyl, $(C_3-C_6)$ lower alkenyl, $(C_3-C_6)$ lower alkynyl, $(C_3-C_8)$ cycloalkyl, formyl, cycloalkylcarbonyl, carboxy, lower alkoxycarbonyl, cycloalkyloxycarbonyl, aryl alkyloxycarbonyl, carbamoyl, $—O—CH_2—CH{=}CH_2$, halogen, halo lower alkyl, trifluoromethyl, $—OCF_3$, $—S[(C_1-C_6)$ lower alkyl], $—OC(O)N[(C_1-C_6)$ lower $alkyl]_2$, $—CONH[(C_1-C_6)$ lower alkyl], $—CON[(C_1-C_6)$ lower $alkyl]_2$, $(C_1-C_6)$ lower alkylamino, di-$[(C_1-C_6)$ lower alkyl]amino, $(C_1-C_6)$ lower alkyl di-$[(C_1-C_6)$ lower alkyl]amino, hydroxy, cyano,trifluoromethylthio, nitro, amino, $(C_1-C_6)$ lower alkylsulfonyl, aminosulfonyl, $(C_1-C_6)$ lower alkylaminosulfonyl,

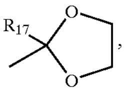

, phenyl or naphthyl;

$R_{11}$ and $R_{12}$ are, independently, selected from the group ofhydrogen, $(C_1-C_6)$ lower alkyl, $(C_3-C_6)$ lower alkenyl, $(C_1-C_6)$ lower alkynyl, cyclo lower alkyl, or aryl, optionally substituted by hydroxy, $(C_1-C_6)$ lower alkyl, $(C_1-C_6)$ lower alkoxy, halogen, cyano, $—SO_2[(C_1-C_6)$ lower alkyl], or $—S[(C_1-C_6)$ lower alkyl];

R is selected, independently, from the groups:

(g)

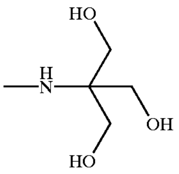

(h)

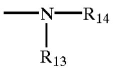

(i)

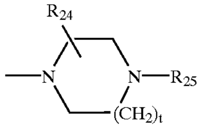

(k)

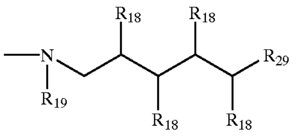

or (m)

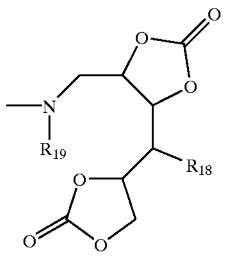

;

$R_{13}$ is selected from hydrogen, $(C_1-C_6)$ lower alkyl, $(C_7-C_{12})$ aryl lower alkyl wherein the aryl moiety is optionally substituted with lower alkoxy, or any of the following groups:

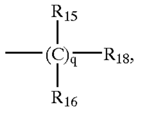
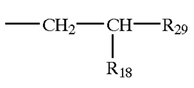
or
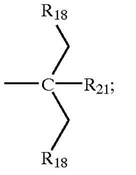

$R_{14}$ is selected from the groups:

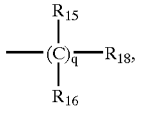
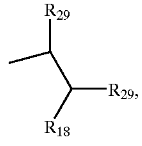
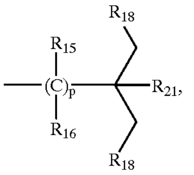
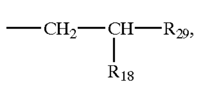
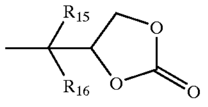
or
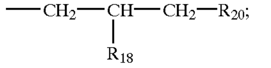

$R_{15}$ and $R_{16}$ are, independently, chosen from the group of hydrogen, $(C_1-C_6)$ lower alkyl or $(C_7-C_{12})$ aryl lower alkyl;

$R_{18}$ is hydroxy, lower alkoxy, or OP wherein P is a hydroxy protecting group, defined as a group providing temporary protection against undesirable reactions during synthetic procedures and to be selectively removable. Common hydroxy protecting groups include, but are not limited to, tert-butyldimethylsilyl, tert-butyldiphenylsilyl, acetyl, trifluoroacetyl, benzyl, benzoyl, methoxymethyl, methylthiomethyl, and others well known in the art (such as those set forth in c.f. Greene et al., *Protective Groups in Organic Syntheses*, 3rd Edn., John Wiley & Sons, New York (1999), the text of which is incorporated herein by reference);

$R_{19}$ is selected from the group of hydrogen, $(C_1-C_6)$ lower alkyl or $(C_7-C_{12})$ aryl lower alkyl;

$R_{21}$ is hydrogen, $(C_1-C_6)$ lower alkyl, or $R_{29}$;

$R_{25}$ is selected from the groups:

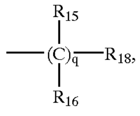
or
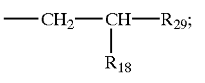

$R_{26}$ is $(C_1-C_6)$ lower alkyl, or aryl $(C_1-C_6)$ lower alkyl;

$R_{29}$ is selected from the group of hydroxy lower alkyl, lower alkoxy lower alkyl, or lower alkyl OP wherein P is a hydroxy protecting group, defined as a group providing temporary protection against undesirable reactions during synthetic procedures and to be selectively removable. Common hydroxy protecting groups include, but are not limited to, tert-butyldimethylsilyl, tert-butyldiphenylsilyl, acetyl, trifluoroacetyl, benzyl, benzoyl, methoxymethyl, methylthiomethyl, and others well known in the art (c.f. Greene et al., *Protective Groups in Organic Syntheses*, 3rd Edn., John Wiley & Sons, New York (1999);

p is an integer from 0 to 1;

q is an integer from 2 to 4;

t is an integer from 1 to 2;

or a pharmaceutically acceptable salt or pro-drug form thereof.

Within each of the groups described herein is a further subset of compounds wherein $R_3$ is hydrogen.

In another additional subset within each group herein is one in which R is the moiety:

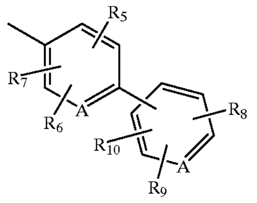

wherein A, $R_5$, $R_6$, $R_7$, $R_8$, $R_9$, and $R_{10}$ are as defined above. Within these groups are a further preferred group wherein R is the moiety:

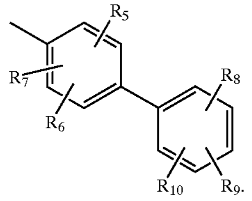

As used herein the term "lower" in relation to alkoxy or alkyl is understood to refer to those groups having from 1 to 6 carbon atoms. Halogen refers to fluorine, chlorine, bromine or iodine.

It is understood by those practicing the art that some of the compounds of this invention depending on the definition of $R_1$, $R_2$, $R_3$, $R_4$, $R_5$, $R_6$, $R_7$, $R_8$, $R_9$, $R_{10}$, $R_{11}$, and $R_{12}$, may contain one or more asymmetric centers and may thus give rise to enantiomers and diastereomers. The present invention includes all stereoisomers including individual diastereomers and resolved, enantiomerically pure R and S stereoisomers; as well as racemates, and all other mixtures of the R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, E-Z isomers, endo-exo isomers, and mixtures thereof which possess the indicated activity. Such isomers may be obtained in pure form by standard separation procedures known to those skilled in the art. It is understood also by those practicing the art that some of the compounds of this invention depending on the definition of $R_5$, $R_6$, $R_8$, $R_9$, $R_{10}$, $R_{11}$, and $R_{12}$ may be chiral due to hindered rotation, and give rise to atropisomers which can be resolved and obtained in pure form by standard procedures known to those skilled in the art. Also included in the present invention are all polymorphs and hydrates of the compounds of the present invention.

DETAILED DESCRIPTION OF THE INVENTION

The present invention comprises the compounds described above, as well as pharmaceutical compositions comprising one or more compounds of this invention in combination or association with one or more pharmaceutically acceptable carriers or excipients. In particular, the present invention provides a pharmaceutical composition which comprises a pharmaceutically or therapeutically effective amount of one or more compounds of this invention in a pharmaceutically acceptable carrier or excipient.

This invention also comprises methods for treating, inhibiting or preventing conditions in a mammal, preferably a human, which are remedied or alleviated by oxytocin antagonist activity including, but not limited to, treatment, inhibition or prevention of preterm labor, dysmenorrhea and suppressing labor prior to caesarian delivery whenever desirable in a mammal, preferably in a human. The methods comprise administering to a mammal in need thereof a therapeutically effective but non-toxic amount of one or more of the compounds of this invention.

The present invention also comprises combinations of the compounds of the present invention with one or more agents useful in the treatment of disorders such as preterm labor, dysmenorrhea, and stopping labor prior to caesarian delivery. More specifically, the compounds of the present invention may be effectively administered in combination with effective amounts of other tocolytic agents used in the treatment, inhibition or prevention of preterm labor, dysmenorrhea or suppressing labor prior to caesarean delivery including β-adrenergic agonists, calcium channel blockers, prostaglandin synthesis inhibitors, other oxytocin antagonists (e.g. atosiban), magnesium sulfate, ethanol, and other agents useful in the treatment of said disorders. The present invention is to be understood as embracing all simultaneous or alternating treatments of any combination of the compounds of the present invention with other tocolytic agents with any pharmaceutical composition useful for the treatment of preterm labor, dysmenorrhea, and suppressing labor prior to caesarean delivery in mammals.

The compositions are preferably adapted for intravenous (both bolus and infusion) and oral administration. However, they may be adapted for other modes of administration including subcutaneous, intraperitoneal, or intramuscular administration to a human or a farm animal in need of a tocolytic agent.

The compounds of the present invention can be used in the form of salts derived from non toxic pharmaceutically acceptable acids or bases. These salts include, but are not limited to, the following: salts with inorganic acids such as hydrochloric acid, hydrobromic acid, sulfuric acid, nitric acid, phosphoric acid and, as the case may be, such organic acids as acetic acid, oxalic acid, citric acid, tartaric acid, succinic acid, maleic acic, benzoic acid, benzene sulfonic acid, fumaric acid, malic acid, methane sulfonic acid, pamoic acid, and para-toluensulfonic acid. Other salts include salts with alkali metals or alkaline earth metals, such as sodium, potassium, calcium or magnesium, or with organic bases including quaternary ammonium salts. The compounds can also be used in the form of esters, carbamates and other conventional prodrug forms, which in general, will be functional derivatives of the compounds of this invention which are readily converted to the active moiety in vivo. This is meant to include the treatment of the various conditions described hereinbefore with a compound of this invention or with a compound which is not specifically disclosed but which converts to a compound of this invention in vivo upon administration. Also included are metabolites of the compounds of the present invention defined as active species produced upon introduction of these compounds into a biological system.

When the compounds of this invention are employed for the above utilities, they may be combined with one or more pharmaceutically acceptable excipients or carriers, for example, solvents, diluents and the like, and may be administered orally in such forms as tablets, capsules (including time release and sustained release formulations), pills, dispersible powders, granules, or suspensions containing, for example, from 0.05 to 5% of suspending agent, syrups containing, for example, from about 10 to 50% of sugar, and elixirs and the like, or parenterally in the form of sterile injectable solutions, suspensions or emulsions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredients employed may vary depending on the particular compound or salt employed, the mode of administration, age, weight, sex and medical condition of the patient, and the severity of the condition being treated. An ordinarily skilled physician, veterinarian or clinician can readily determine and prescribe the effective amount of the agent required to prevent, counter or arrest the progress of the condition. However, in general, satisfactory results are obtained when the compounds of the invention are administered at a daily dose of from about 0.5 to about 500 mg/Kg of mammal body weight, preferably given in divided doses two to four times a day, or in a sustained release form. For most large mammals the total daily dosage is from about 0.5 to 100 mg, preferably from 0.5 to 80 mg/Kg. Dosage forms suitable for internal use comprise from about 0.05 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, glycerol, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example vitamin E, ascorbic acid, BHT and BHA.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under conditions of manufacture and storage and must be preserved against the contaminating action of microorganisms such as bacteria and fungi. The carrier can be a solvent or dispersion medium containing, for example, water, ethanol (e.g. glycerol, propylene glycol, and liquid polyethylene glycol), suitable mixtures thereof, and vegetable oil.

Furthermore, active compounds of the present invention can be administered intranasally using vehicles suitable for intranasal delivery, or transdermally using transdermal skin patches known to those ordinarily skilled in the art. When using a transdermal delivery system, the dosage administration will be continuous rather than in a single or divided daily doses. The compounds of the present invention can also be administered in the form of liposome delivery system wherein the liposomal lipid bilayers are formed from a variety of phospholipids.

Compounds of the present invention may also be delivered by the use of carriers such as monoclonal antibodies to which the active compounds are coupled. The compounds of the present invention may also be coupled to soluble polymers as drug carriers or to biodegradable polymers useful in achieving controlled release of the active agent.

Also according to the present invention there are provided processes for producing the compounds of the present invention.

PROCESS OF THE INVENTION

The compounds of the present invention may be prepared according to one of the general processes outlined below.

The compounds of general formula (I) wherein $R_4$ consists of the moiety B—C, where B is selected from the group (a) or (b) and C is selected from the group of (c), (d), (e) and (f) defined hereinbefore, can be conveniently prepared as shown in Scheme I.

Scheme I

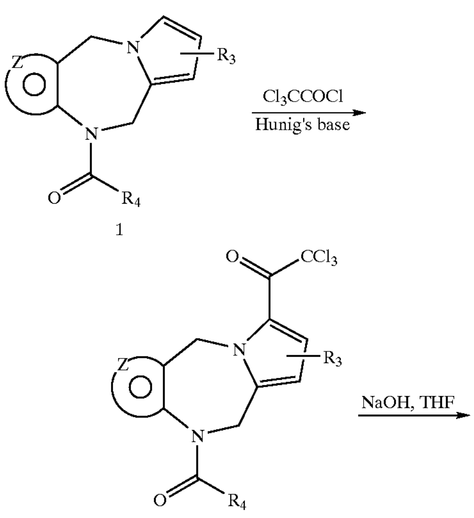

1

2

-continued

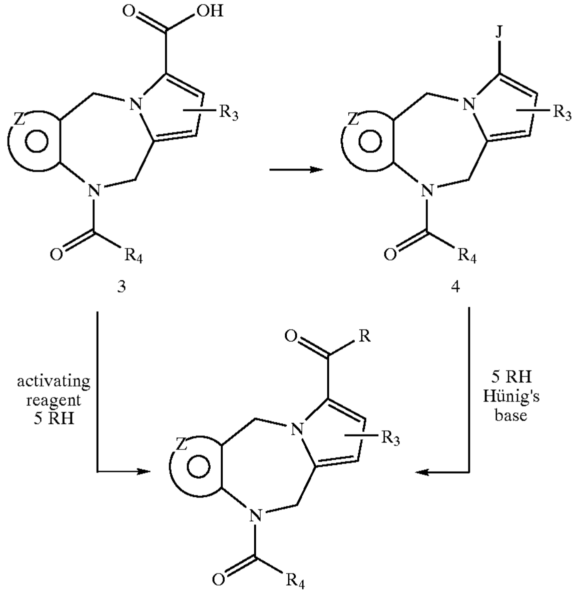

3

4

(I)

According to the above preferred process, a tricyclic azepine of formula (1) wherein

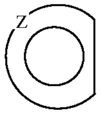

, $R_3$ and $R_4$ are defined hereinbefore, is reacted with perhaloalkanoyl halide preferably trichloroacetyl chloride, in the presence of an organic base such as N,N-diisopropylethyl amine (Hünig's base), in an aprotic organic solvent such as dichloromethane, at temperatures ranging from −10° C. to ambient to provide the desired trichloroacetyl intermediate of formula (2). Subsequent hydrolysis of (2) with aqueous base such as sodium hydroxide in an organic solvent such as tetrahydrofuran or acetone at temperatures ranging from −10° C. to ambient, yields the intermediate acid of formula (3). The required activation of the carboxylic acid (3) for the subsequent coupling with a primary or secondary amine of formula (5) can be accomplished in several ways. Thus, (3) can be converted to an acid halide preferable a chloride or bromide of formula (4, J═COCl or COBr) by reaction with thionyl chloride(bromide) or oxalyl chloride(bromide) or similar reagents known in the art, either neat or in the presence of an inorganic base such as potassium carbonate, or in the presence of an organic base such as pyridine, 4-(dimethylamino)pyridine, or a tertiary amine such as triethylamine, in an aprotic solvent such as dichloromethane, N,N-dimethylformamide or tetrahydrofuran, at temperatures ranging from −5° C. to 50° C. to yield the intermediate acylated derivative (4). Subsequent coupling of the acid chloride(bromide) (4, J═COCl or COBr) with an appropriately substituted primary or secondary amine of formula (5) in the presence of a stoichiometric amount of Hunig's base, in an aprotic solvent such as dichloromethane, N,N-dimethylformamide or tetrahydrofura, at temperatures ranging from ambient to the reflux temperature of the solvent provides the desired compounds of formula (I) wherein

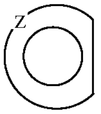
,

R, $R_3$ and $R_4$ are as defined hereinbefore.

Alternatively, the acylating species can be a mixed anhydride of the corresponding carboxylic acid, such as that prepared by treating said acid of formula (3) with 2,4,6-trichlorobenzoyl chloride, in an aprotic organic solvent such as dichloromethane, according to the procedure of Inanaga et al., *Bull. Chem. Soc. Jpn.* 52, 1989 (1979). Treatment of said mixed anhydride of formula (4) with an appropriately substituted primary or secondary amine of formula (5) in an aprotic solvent such as dichloromethane, at temperatures ranging from ambient to the reflux temperature of the solvent provides the desired compounds of formula (I) wherein

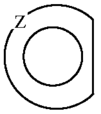
,

R, $R_3$ and $R_4$ are as defined hereinbefore.

Alternatively, amidation of the carboxylic acids of formula (3) can be effectively carried out by treatment of said acid with triphosgene, in an aprotic solvent such as dichloromethane, followed by reaction of the activated intermediate with an appropriately substituted primary or secondary amine of formula (5), in the presence of an organic base such as Hünig's base, at temperatures ranging from −10° C. to ambient.

Another preferred process for the preparation of the compounds of the present invention of formula (I) wherein

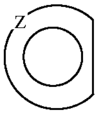
,

R, $R_3$ and $R_4$ are as defined hereinbefore, consists of treating the acid of formula (3) with an activating reagent such as N,N-dicyclohexylcarbodiimide or 1-ethyl-3-(3-dimethylamino-propyl) carbodiimide hydrochloride, in the presence of 1-hydroxybenzotriazole, followed by reaction of the activated intermediate with an appropriately substituted primary or secondary amine of formula (5), preferably in the presence of an organic base such as Hunig's base and a catalytic amount of 4-(dimethylamino)pyridine, in an aprotic solvent such as dichloromethane, N,N-dimethylformamide or tetrahydrofuran, at temperatures ranging from −10° C. to ambient.

In another preferred process, said acid (3) can be activated by treatment with other activating agents such as N,N'-carbonyldiimidazole, in an aprotic solvent such as dichloromethane or tetrahydrofuran, at temperatures ranging from −10° C. to the reflux temperature of the solvent. Subsequent reaction of the intermediate activated imidazolide with an appropriately substituted primary or secondary amine of formula (5) provides the desired compounds of formula (I), wherein

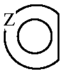
,

R, $R_3$ and $R_4$ are as defined hereinbefore.

Alternatively, the coupling of the appropriately substituted primary or secondary amine of formula (5) with said acid of formula (3) can be effectively carried out by using hydroxybenzotriazole tetramethyluronium hexafluorophosphate as the coupling reagent, in the presence of an organic base such as Hünig's base, and in a solvent such as N,N-dimethylformamide, at temperatures ranging from −10° C. to ambient to provide in good isolated yield and purity the desired compounds of formula (I) wherein

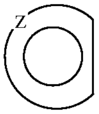
,

R, $R_3$ and $R_4$ are as defined hereinbefore.

Related coupling reagents such as diphenylphosphoryl azide, diethyl cyano phosphonate, benzotriazol-1-yl-oxy-tris-(dimethylamino) phosphonium hexafluorophosphate and all other reagents known in the literature that have been used in the formation of amide bonds in peptide synthesis can also be used for the preparation of compounds of formula (I) wherein

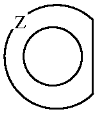
,

R, $R_3$ and $R_4$ are as defined hereinbefore.

As an alternative, reaction of the intermediate 3-trihalomethylketone of formula (2) directly with an appropriately substituted primary or secondary amine of formula (5) also provides the desired compounds of formula (I) wherein

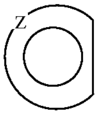
,

R, $R_3$ and $R_4$ are as defined hereinbefore.

The method of choice for the preparation of compounds of formula (I) from the intermediate carboxylic acid (3) is ultimately chosen on the basis of its compatibility with the R, $R_3$ and $R_4$ groups, and its reactivity with the tricyclic diazepine of formula (1).

Another preferred process for the preparation of (I) of Scheme I is shown in Scheme II. A tricyclic diazepine of formula (1) is reacted with diphosgene in an aprotic solvent such as dichloromethane, preferably in the presence of an organic base such as triethylamine, followed by reaction of the resulting acylated intermediate with an appropriately substituted primary or secondary amine of formula (5), to provide the desired compounds of formula (I) wherein

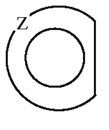

,

R, $R_3$ and $R_4$ are as defined hereinbefore.

Scheme II

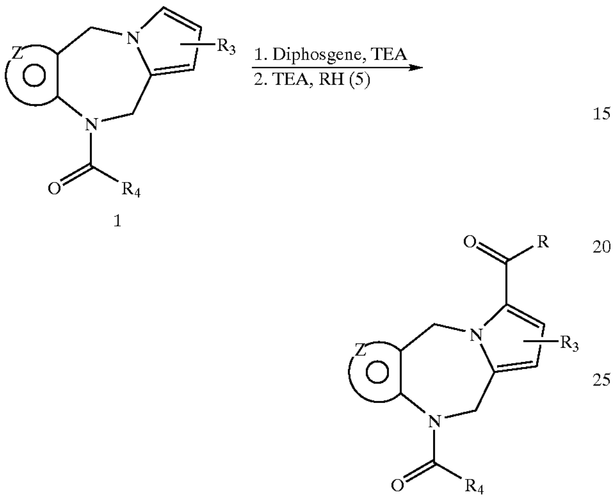

1

(I)

The tricyclic diazepines of formula (1) of Scheme I wherein $R_4$ is chosen on the basis of its compatibility with the reaction scheme, can be conveniently prepared as shown in Scheme III.

Scheme III

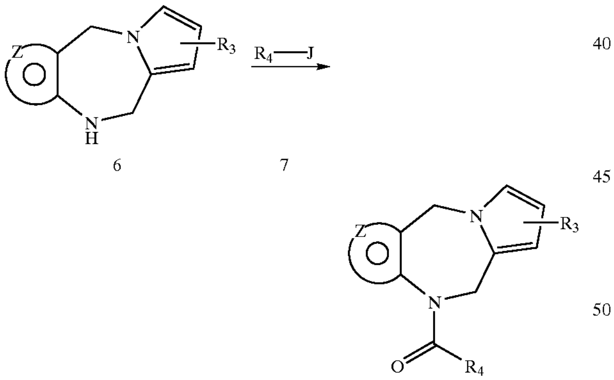

6

7

1

Thus, a tricyclic diazepine of formula (6) is treated with an appropriately substituted acylating agent such as an aroyl halide, preferably an appropriately substituted acyl chloride or bromide of formula (7, J=COCl or COBr) wherein $R_4$ is ultimately chosen on the basis of its compatibility with the present reaction scheme, in the presence of an inorganic base such as potassium carbonate, or in the presence of an organic base such as pyridine, 4-(dimethylamino)pyridine, or a tertiary amine such as triethylamine or N,N-diisopropylethyl amine, in an aprotic solvent such as dichloromethane, N,N-dimethylformamide or tetrahydrofuran, at temperatures ranging from −5° C. to 50° C. to provide intermediates of general formula (1) wherein $R_4$ is defined hereinbefore.

Alternatively, the acylating species of formula (7) can be a mixed anhydride of the corresponding carboxylic acid, such as that prepared by treating said acid with 2,4,6-trichlorobenzoyl chloride, in an aprotic organic solvent such as dichloromethane, according to the procedure of Inanaga et al., *Bull. Chem. Soc. Jpn.*, 52, 1989 (1979).

Treatment of said mixed anhydride of general formula (7) with a tricyclic diazepine of formula (6) in a solvent such as dichloromethane, and in the presence of an organic base such as 4-(dimethylamino)pyridine, at temperatures ranging from 0° C. to the reflux temperature of the solvent, yields the intermediate acylated derivative (1) of Scheme III.

The acylating intermediate of formula (7) is ultimately chosen on the basis of its compatibility with the $R_4$ groups, and its reactivity with the tricyclic diazepine of formula (6).

The desired intermediates of formula (7) of Scheme III wherein $R_4$ consists of the moiety B—C wherein B is (a) and C is (c) can be conveniently prepared by a process shown in Scheme IV. Thus, an appropriately substituted aryl (heteroaryl) iodide (bromide, chloride or trifluoromethane sulfonate) of formula (8, wherein P is a carboxylic acid protecting group, preferably P=alkyl or benzyl, M=I, Br, Cl, OTf) wherein A, $R_5$, $R_6$ and $R_7$ are defined hereinbefore, is reacted with an aryl(heteroaryl) tri(alkyl)tin(IV) derivative of formula (9, W=Sn(trialkyl)$_3$, preferably Sn(n-Bu)$_3$) wherein A, $R_8$, $R_9$ and $R_{10}$ are defined hereinbefore, in the presence of a Pd(0) catalyst, in the presence or absence of inorganic salts (e.g. LiCl), to provide the intermediate ester (10). Subsequent unmasking of the carboxylic acid by hydrolysis, hydrogenolysis or similar methods known in the art, followed by activation of the intermediate acid (11) provides the desired compounds of formula (19) wherein A, $R_5$, $R_6$, $R_7$, $R_8$, $R_9$ and $R_{10}$ are hereinbefore defined, suitable for coupling with the tricyclic diazepine of formula (6).

Scheme IV

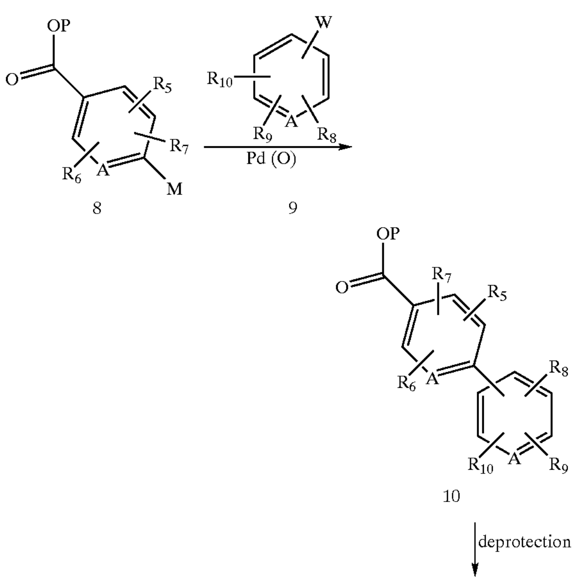

8

9

10

-continued

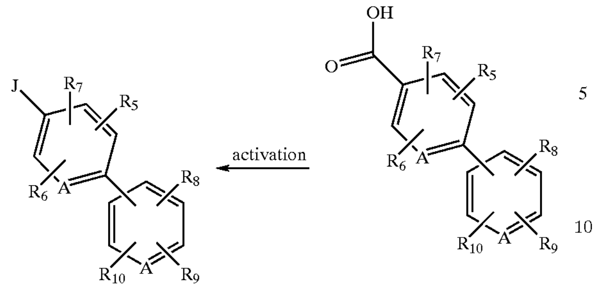

19 11

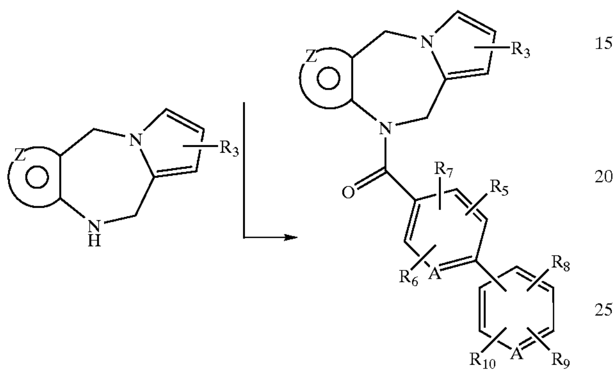

6 (1)

The desired intermediates of formula (7) of Scheme III wherein $R_4$ consists of the moiety B—C where B is (a) and C is (d), (e) or B is (b) and C is either (c), (d), (e) or (f) can be prepared by a process analogous to that exemplified in Scheme IV by replacing intermediates of formula (8 and 9) with appropriately substituted naphthyl, quinolyl, pyrimidinyl or pyrazinyl intermediates.

Alternatively, the desired intermediates of formula (10) of Scheme IV wherein $R_4$ consists of the moiety B—C where B is (a) and C is (c) can be prepared by Suzuki coupling from the iodide(bromide, chloride, trifluoromethanesulfonate) (8, M═I, Br, Cl or OTf) and an appropriately substituted aryl(heteroaryl) boron derivative of formula (9, preferably W═$B(OH)_2$) in the presence of a palladium catalyst such as palladium(II) acetate or tetrakis(triphenylphosphine) palladium(0), and an organic base such as triethylamine or an inorganic base such as sodium(potassium or cesium) carbonate with or without added tetrabutylammonium bromide(iodide), in a mixture of solvents such as toluene-ethanol-water, acetone-water, water or water-acetonitrile at temperatures ranging from ambient to the reflux temperature of the solvent (Suzuki, *Pure & Appl. Chem.* 66, 213–222 (1994); Badone et al., *J. Org. Chem.* 62, 7170–7173 (1997); Wolfe et al., *J. Am. Chem. Soc.* 121, 9559 (1999); Shen, *Tetr. Letters* 38, 5575 (1997)). The exact conditions for the Suzuki coupling of the halide and the boronic acid intermediates are chosen on the basis of the nature of the substrate and the substituents. Alternatively, the coupling of (8, M═I or Br) with (9, A═N) can be carried out by using a dialkylborane, preferably a diethylpyridoborane in the presence of an inorganic base such as potassium hydroxide and tetrabutylammonium bromide(iodide) in an aprotic solvent such as tetrahydrofuran, according to the method of Ishikura et al., *Synthesis* 936–938 (1984). The desired intermediates of formula (10) of Scheme IV can be similarly prepared from the bromide (8, M═Br) and the boronic acid (9) in a solvent such as dioxane in the presence of potassium phosphate and a Pd(0) catalyst.

Alternatively, a cross coupling reaction of an iodide (bromide, or trifluoromethane sulfonate) of formula (9, W═Br, I, OTf) with a bis(pinacolato)diboron [boronic acid, or trialkyltin(IV)] derivative of formula (8, M═

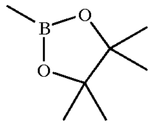, $B(OH)_2$, or $SnBu_3$) yields the desired intermediate of formula (10) which is converted to (I) in the manner of Scheme IV.

The desired intermediates of formula (10) of Scheme IV wherein $R_4$ consists of the moiety B—C wherein B is (a) and C is (d), (e) or (f), or B is (b) and C is either (c), (d), (e) or (f) can be prepared in analogous fashion by replacing intermediates of formulas (8 and 9) with appropriately substituted naphthyl, quinolyl, pyrimidinyl or pyrazinyl intermediates.

The required appropriately substituted aryl(heteroaryl) halides of formula (8, M═Br or I) of Scheme IV are either available commercially, or are known in the art or can be readily accessed in quantitative yields and high purity by diazotization of the corresponding substituted anilines (8, P═H, alkyl or benzyl, M═$NH_2$) followed by reaction of the intermediate diazonium salt with iodine and potassium iodide in aqueous acidic medium essentially according to the procedures of Street et al,. *J. Med. Chem.* 36, 1529 (1993) and Coffen et al., *J. Org. Chem.* 49, 296 (1984) or with copper(I) bromide, respectively (March, *Advanced Organic Chemistry*, $3^{rd}$ Edn., p.647–648, John Wiley & Sons, New York (1985)).

Alternatively, the desired intermediates of formula (11, A═CH) of Scheme IV wherein $R_4$ consists of the moiety B—C wherein B is (a, A═CH) and C is (c, A═CH) can be conveniently prepared as shown in Scheme V by cross-coupling reaction of an appropriately substituted pinacolato borane of formula (13, A═CH) wherein $R_8$, $R_9$ and $R_{10}$ are hereinbefore defined, with an aryl triflate of formula (14, Y═OTf) or an aryl halide (14, Y═Br, I) wherein $R_5$, $R_6$ and $R_7$ are defined hereinbefore, according to the general procedures of lshiyama et al., *Tetr. Lett.* 38, 3447–3450 (1997) and Giroux et al. *Tetr. Lett.* 38, 3841–3844 (1997), followed by basic or acidic hydrolysis of the intermediate nitrile of formula (15) (cf. March, *Advanced Organic Chemistry*, $3^{rd}$ Edn., John Wiley & Sons, New York, p. 788 (1985)).

Scheme V

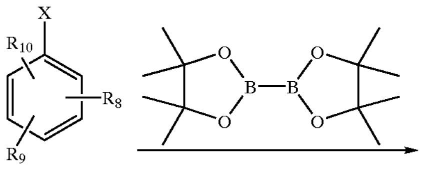

12 16

-continued

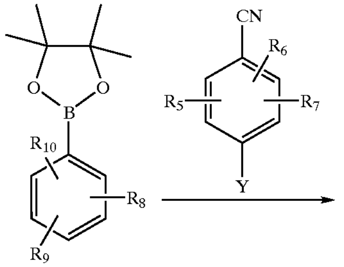

13 14

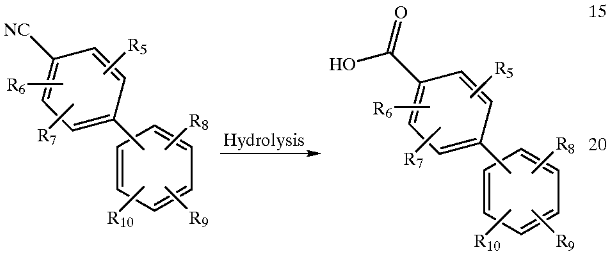

15 11

Alternatively, reaction of an iodide (bromide, or trifluoromethanesulfonate) of formula (12, X═Br, I, or Tf) with a bis(pinacolato)diboron [boronic acid or trialkyl tin (IV)] derivative of formula (14, Y═

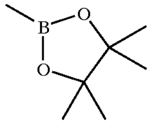

, $B(OH)_2$, or $SnBu_3$) yields the desired intermediate of formula (15) which is converted to (6) in the manner of Scheme V.

The desired intermediates of formula (11) of Scheme IV can be prepared in analogous fashion by replacing intermediates of formulas (13 and 14) with appropriately substituted naphthyl intermediates.

The desired phenyl boronic esters of formula (13) of Scheme V can be conveniently prepared by the palladium-catalyzed cross-coupling reaction of the pinacol ester of diboronic acid (16) with an appropriately substituted aryl halide preferably a bromide or iodide (12, X═Br, I) or aryl triflate (12, X═OTf) according to the described procedures of Ishiyama et al., *J. Org. Chem.* 60, 7508–7510 (1995) and Giroux et al., *Tetr. Lett.* 38, 3841–3844 (1997).

The desired compounds of formula (1) of Scheme IV wherein $R_4$ consists of the moiety B—C wherein B is (a) and C is (c) can be alternatively prepared by a process shown in Scheme VI.

Scheme VI

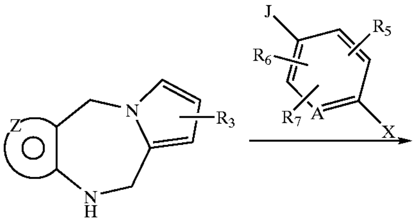

6 17

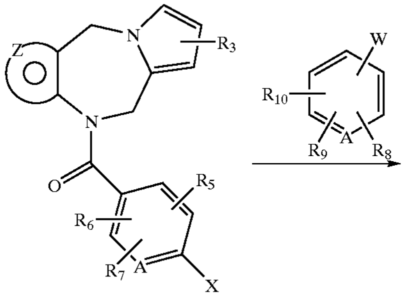

18 9

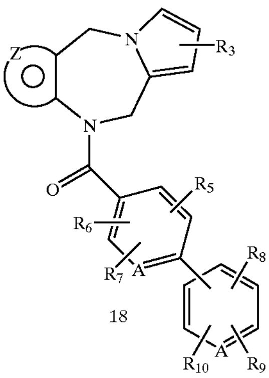

18

(1)

Thus, a tricyclic diazepine of formula (6) is treated with an appropriately substituted acylating agent such as a halo aroyl(heteroaroyl)halide, preferably an iodo(bromo) aroyl (heteroaroyl) chloride(bromide) of formula (17, J═COCl or COBr; X═I, Br) wherein $R_5$, $R_6$ and $R_7$ are hereinbefore defined using any of the procedures hereinbefore described, to provide the acylated intermediate of general formula (18) of Scheme VI.

Alternatively, the acylating species of formula (17) can be a mixed anhydride of the corresponding carboxylic acid. Treatment of said mixed anhydride of general formula (17) with a tricyclic diazepine of formula (6) according to the procedure described hereinbefore yields the intermediate acylated derivative (18).

The acylating intermediate of formula (17) is ultimately chosen on the basis of its compatibility with A and the $R_5$, $R_6$ and $R_7$ groups, and its reactivity with the tricyclic diazepine of formula (6).

A Stille coupling reaction of (18, X═I) with an appropriately substituted organotin reagent such as a trialkyltin (IV) derivative, preferably a tri-n-butyltin(IV) derivative of formula (9, W═$SnBu_3$) where A, $R_8$, $R_9$ and $R_{10}$ are hereinbefore defined, in the presence of a catalyst such as tetrakis (triphenylphosphine) palladium (0), in an aprotic organic solvent such as toluene and N,N-dimethylformamide, at temperatures ranging from ambient to 150° C. (cf. Farina et al., *J. Org. Chem*, 59, 5905 (1994) and references cited therein) affords the desired compounds of formula (1) wherein

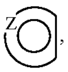

A, $R_3$, $R_5$, $R_6$, $R_7$, R, $R_9$ and $R_{10}$ are as defined hereinbefore.

Alternatively, reaction of a compound of formula (18, X=Cl, Br or 1) with an appropriately substituted aryl (heteroaryl) boronic acid of formula (9, W=$B(OH)_2$) wherein A, $R_5$, $R_6$, $R_7$, $R_8$, $R_9$ and $R_{10}$ are hereinbefore defined, in a mixture of solvents such as toluene-ethanol-water, and in the presence of a Pd(0) catalys, and a base such as sodium carbonate, at temperatures ranging from ambient to the reflux temperature of the solvent, yields the desired compounds of formula (1) wherein

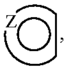

A, $R_3$, $R_5$, $R_6$, $R_7$, $R_8$, $R_9$ and $R_{10}$ are as defined hereinbefore.

The preferred substituted aroyl(heteroaroyl) chlorides (bromides) of formula (17) of Scheme VI(X=I, Br; J=COCl or COBr) wherein A, $R_5$, $R_6$ and $R_7$ are as defined hereinbefore, are either available commercially, or are known in the art, or can be readily prepared by procedures analogous to those in the literature for the known compounds.

The intermediates of formula (9, W=$Sn(alkyl)_3$, alkyl=n-butyl) of Scheme VI are either commercially available, or can be conveniently prepared as shown in Scheme VII from the corresponding bromo starting materials of formula (20) wherein A, $R_8$, $R_9$, and $R_{10}$ are hereinbefore defined, by first reacting them with n-butyl lithium followed by reaction of the intermediate lithiated species with a trialkyl (preferably trimethyl or tri-n-butyl)tin(IV) chloride to give the desired stannane of formula (9, alkyl=n-butyl) wherein $R_8$, $R_9$, and $R_{10}$ are as defined hereinbefore.

Scheme VII

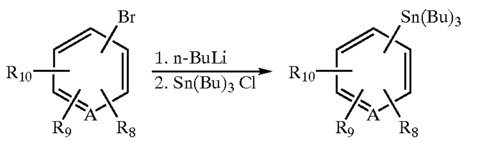

20 9

The preferred substituted aryl(heteroaryl) boronic acids of formula (9, W=$B(OH)_2$) are either available commercially, or are known in the art, or can be readily prepared by procedures analogous to those in the literature for the known compounds.

The desired compounds of formula (1) of Scheme VI wherein $R_4$ consists of the moiety B—C wherein B is (a) and C is (d), (e) or (f), or B is (b) and C is either (c), (d), (e) or (f) can be prepared in analogous fashion by replacing intermediates of formulas (17 and 9) with appropriately substituted naphthyl, quinolyl, pyrimidinyl or pyrazinyl intermediates.

Alternatively, as shown in Scheme VIII, the appropriately substituted aroyl(heteroaroyl) halides, preferably aroyl (heteroaroyl) chlorides of formula (21, J=COCl) where A, $R_5$, $R_6$ and $R_7$ are hereinbefore defined, are reacted with a tricyclic diazepine of formula (6) to provide the intermediate bromides of formula (22). Subsequent reaction of (22) with an hexa alkyl-di-tin (preferably hexa-n-butyl-di-tin(IV)) in the presence of a Pd(0) catalyst such as tetrakis(triphenylphosphine)palladium(0) and lithium chloride, provides the stannane intermediate of formula (23). Further reaction of the tri-n-butyl tin(IV) derivative (23) with the appropriately substituted aryl(heteroaryl) halide of formula (24, M=Br, I) wherein A, $R_8$, $R_9$, and $R_{10}$ are hereinbefore defined, in the presence of a Pd(0) catalyst such as tetrakis (triphenylphosphine) palladium(0), yields the desired compounds of formula (1) wherein $R_4$ consists of the moiety B—C wherein B is (a) and C is (c), and

A, $R_5$, $R_6$, $R_7$, $R_8$, $R_9$ and $R_{10}$ are defined hereinbefore.

Scheme VIII

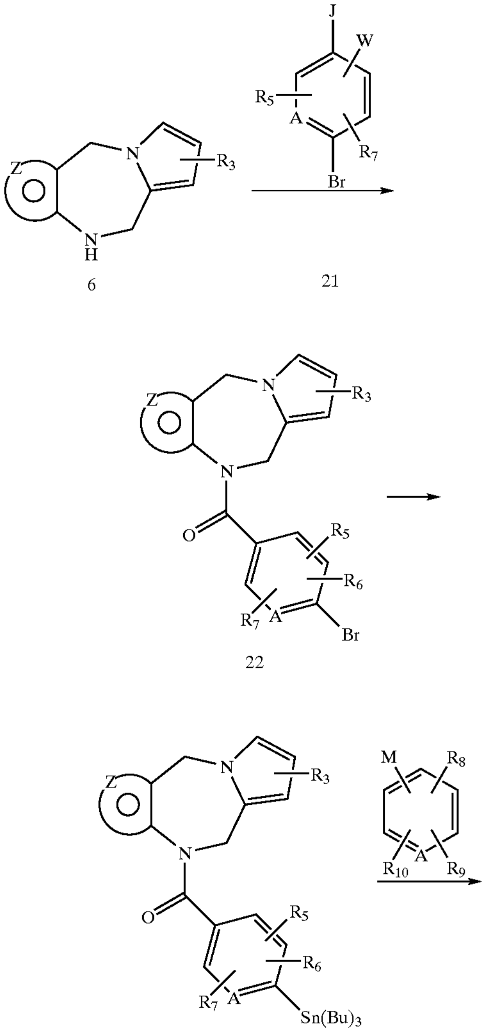

6 21 22 23 24

-continued

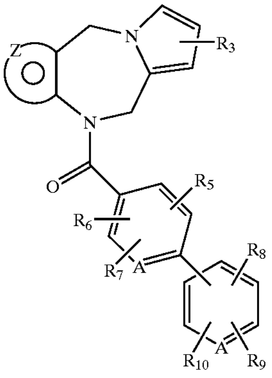

(1)

The desired compounds of formula (1) of Scheme VIII wherein $R_4$ consists of the moiety B—C wherein B is (a) or (b), and C is (d), (e) or (f) can be prepared in analogous fashion by replacing intermediates of formulas (21 and 24) with appropriately substituted naphthyl, quinolyl, pyrimidinyl or pyrazinyl intermediates.

Alternatively, the desired compounds of formula (1) of Scheme VIII wherein $R_4$ consists of the moiety B—C wherein B is (a, A=CH), and C is (c, A=CH) can be prepared as shown in Scheme IX.

Scheme IX

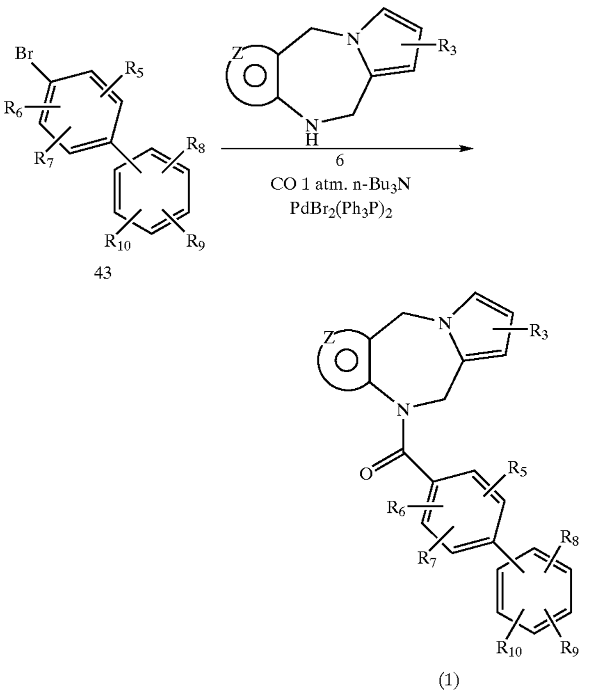

43

6

(1)

Thus, an appropriately substituted biphenyl of formula (43) wherein $R_5$, $R_6$, $R_7$, $R_8$, $R_9$ and $R_{10}$ are defined hereinbefore, is treated with carbon monoxide in the presence of a tricyclic diazepine of formula (6), a palladium(0) catalyst preferably $PdBr_2(Ph_3P)_2$, and a tertiary amine preferably n-tributylamin, in a solvent such as anisole or dioxane at temperatures ranging from ambient to the reflux temperature of the solvent (cf. Schoenberg et al., *J. Org. Chem.* 39, 3327 (1974)), to provide the desired compounds of formula (1) wherein A is CH, and

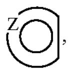

$R_3$, $R_5$, $R_6$, $R_7$, $R_8$, $R_9$ and $R_{10}$ are defined hereinbefore.

In analogous fashion one can prepare compounds of formula (1) of Scheme IX wherein $R_4$ consists of the moiety B—C wherein B is (b) and C is (c, A=CH) or (d, A=CH) provided that the intermediates of formula (43) are replaced by the appropriately substituted phenyl or naphthyl intermediates.

A preferred process for the preparation of the compounds of formula (1) of Scheme I wherein

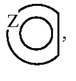

A, $R_3$, $R_5$, $R_6$ and $R_7$ are defined hereinbefore, and $R_4$ consists of the moiety B—C wherein B is (a) and C is (g) defined hereinbefore, is shown in Scheme X.

Scheme X

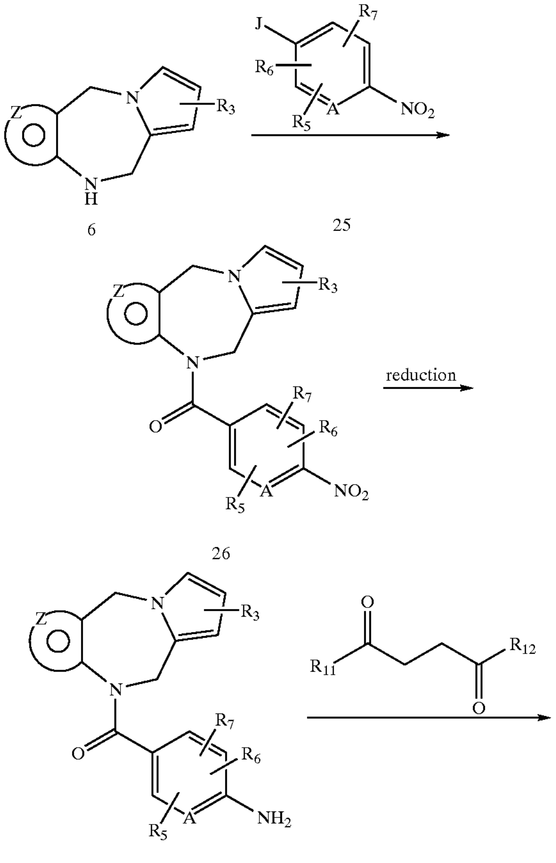

6 25

26

27 28

-continued

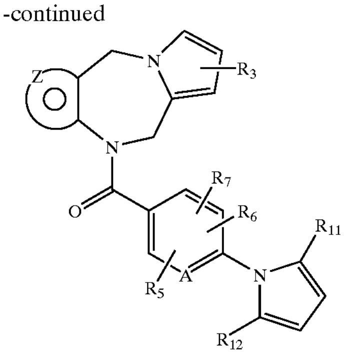

(1)

Thus, an appropriately substituted aroyl(heteroaroyl) halide preferably an aroyl(heteroaroyl) chloride, of formula (25, J=COCl) is reacted with a tricyclic diazepine of formula (6), in the presence of a base such as pyridine, or a tertiary amine such as triethylamine or N,N-diisopropylethylamine, in an aprotic organic solvent such as dichloromethane or tetrahydrofuran, at temperatures from −40° C. to 50° C. to provide the acylated intermediate of formula (26). Alternatively, the acylating species can be a mixed anhydride under the reaction conditions described hereinbefore. Subsequent reduction of (26) is preferably effected under conditions of catalytic reduction (i.e. hydrogen, Pd on charcoal), transfer hydrogenation (i.e. hydrazine/ethanol/Pd on charcoal) or under chemical reduction conditions (i.e. with tin(II)chloride dihydrate in a protic organic solvent such as ethanol, or zinc in acetic acid) or related reduction conditions known in the art, to yield the desired aniline of formula (27). The exact conditions for the conversion of the nitro to amino group are chosen on the basis of compatibility with the preservation of other functional groups in the molecule. Condensation of (27) with a 1,4-diketone of formula (28) in an aprotic organic solvent such as benzene or toluene in the presence of acetic acid or a catalytic amount of paratoluenesulfonic acid with concomitant removal of water at temperatures ranging from ambient to reflux temperature of the solvent according to the general procedure of Bruekelman et al., *J. Chem. Soc. Perkin Trans. I*, 2801–2807 (1984), provides the desired compounds of formula (I) wherein $R_4$ consists of the moiety B—C wherein B is (a) and C is (g), and

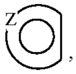,

A, $R_3$, $R_5$, $R_6$, $R_7$, $R_{11}$ and $R_{12}$ are defined hereinbefore.

The desired compounds of formula (1) of Scheme X wherein $R_4$ consists of the moiety B—C wherein B is (b) and C is (g) can be prepared in analogous fashion by replacing the intermediate of formula (25) with an appropriately substituted naphthyl.

Alternatively, the desired compounds of formula (1) of Scheme X can be prepared as shown in Scheme XI.

Scheme XI

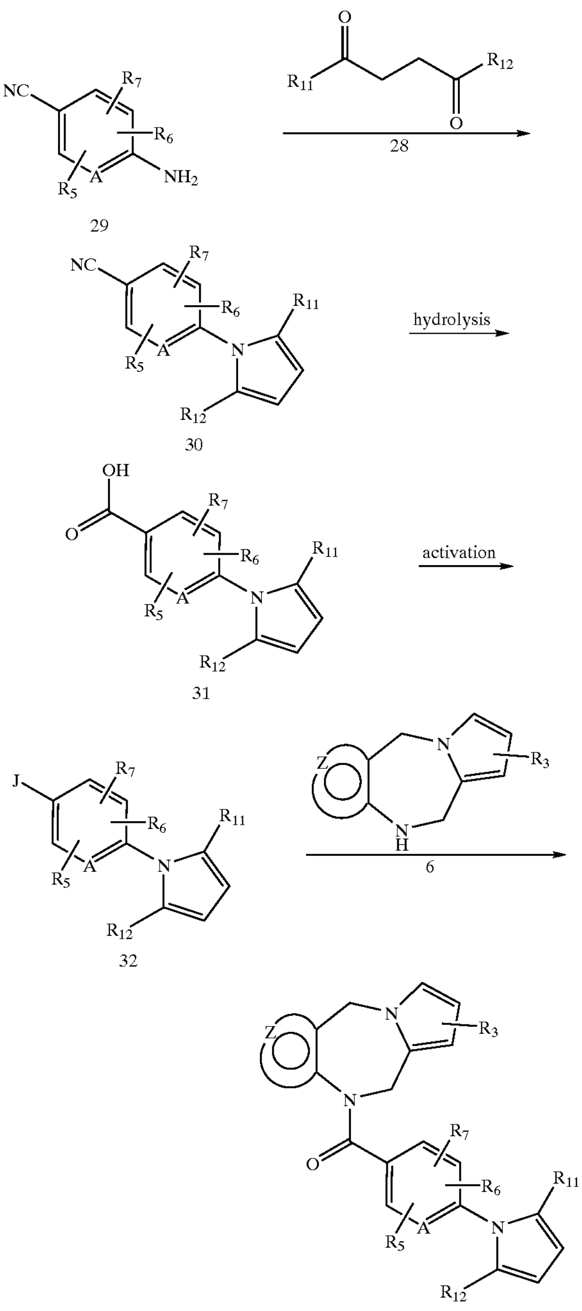

(1)

According to this process an aryl(heteroaryl) nitrile of formula (29) is condensed with a 1,4-diketone of formula (28), in an aprotic organic solvent such as benzene or toluene, in the presence of acetic acid or a catalytic amount of paratoluenesulfonic acid with concomitant removal of water, at temperatures ranging from ambient to reflux temperature of the solvent according to the general procedure of Bruekelman et al., *J. Chem. Soc. Perkin Trans. I*, 2801–2807 (1984), to yield the intermediate pyrrole of formula (30). Subsequent hydrolysis of the nitrile (30) to the carboxylic acid of formula (31) is efficiently accomplished by treatment of (30) with aqueous base (cf. March, *Advanced Organic Chemistry*, $3^{rd}$ Edn., John Wiley & Sons, New York, p. 788

(1985)). Subsequent conversion of the acid (31) into an acylating species, preferably an acid chloride(bromide) of formula (32, J=COCl or COBr) or a mixed anhydride is accomplished by procedures analogous to those described hereinbefore. The acylating agent (32) is used to acylate a tricyclic diazepine of formula (6) to provide the desired compounds of formula (1) wherein

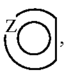

A and $R_3$ are defined hereinbefore, and $R_4$ consists of the moiety B—C wherein B is (a) and C is the moiety (g) defined hereinbefore.

The compounds of formula (1) of Scheme XI wherein $R_4$ consists of the moiety B—C wherein B is (b) and C is (g) defined hereinbefore, can be prepared in analogous fashion by replacing the intermediates of formula (29) with an appropriately substituted naphthyl.

A preferred process for the preparation of the desired compounds of general formula (I) of Scheme I wherein $R_4$ consists of the moiety B—C, where B is selected from the group (a) and C is selected from the group (g) defined hereinbefore is shown in Scheme XII.

Scheme XII

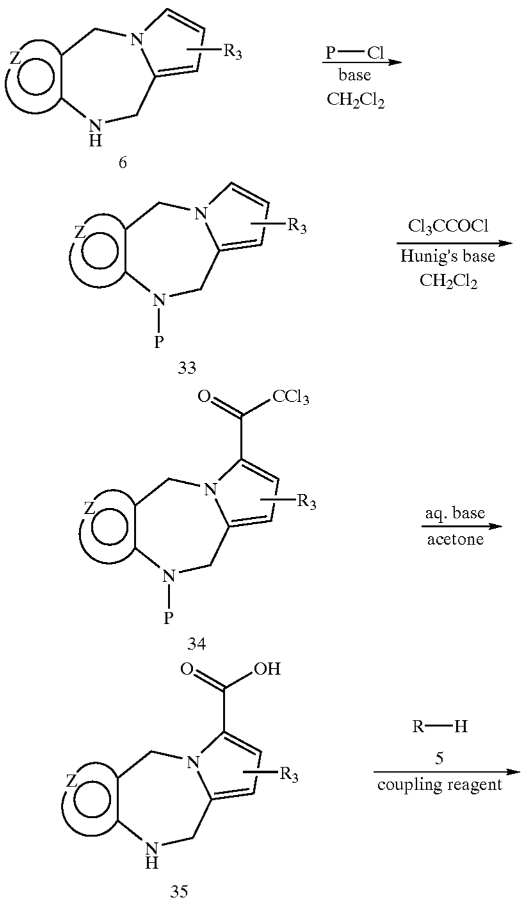

-continued

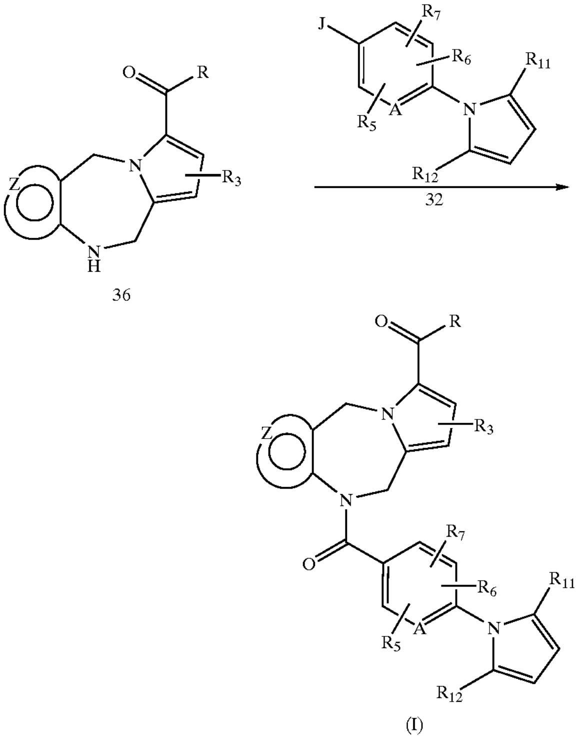

Thus, a tricyclic diazepine of formula (33) wherein

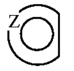

and $R_3$ are defined hereinbefore, carrying a protecting group such as a fluorenylalkoxycarbonyl group, preferably a fluorenylmethyloxycarbonyl (P=Fmoc) group, or an alkoxycarbonyl protecting group preferably a tert-butyloxycarbonyl (P=Boc) group is reacted with a perhaloalkanoyl halide preferably trichloroacetyl chloride, in the presence of an organic base such as N,N-diisopropylethyl amine (Hunig's base) or a tertiary amine such as triethylamine, optionally in the presence of catalytic amounts of 4-(dimethylamin)pyridine, in an aprotic organic solvent such as dichloromethane, at temperatures ranging from −10° C. to ambient to provide the desired trichloroacetyl intermediate of formula (34). Subsequent hydrolysis of the trichloroacetyl group with aqueous base such as sodium hydroxide, in an organic solvent such as acetone, at temperatures ranging from −10° C. to ambient, is accompanied by simultaneous removal of the protecting group and yields the intermediate acid of formula (35). The required amidation of the carboxylic acid (35) can be effectively accomplished by treating (35) with an activating reagent such as N,N-dicyclohexyl carbodiimide or 1-ethyl-3-(3-dimethylamino-propyl)carbodiimide hydrochloride in the presence of 1-hydroxybenzotriazole, followed by reaction of the activated intermediate with an appropriately substituted primary or secondary amine of formula (5) preferably in the presence of Hünig's base or a catalytic amount of 4-(dimethylamino)pyridine in an aprotic solvent such as dichloromethane, N,N-dimethylformamide or tetrahydrofuran, at temperatures ranging from −10° C. to ambient.

Other coupling reagents known in the literature that have been used in the formation of amide bonds in peptide synthesis can also be used for the preparation of compounds of formula (36) wherein

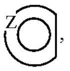

R and $R_3$ are as defined hereinbefore. The method of choice for the preparation of compounds of formula (36) from the intermediate carboxylic acid (35) is ultimately chosen on the basis of its compatibility with the

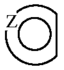

and $R_3$ groups, and its reactivity with the tricyclic diazepine of formula (6).

Subsequent reaction of a tricyclic diazepine amide (36) with an acylating agent of formula (32) of Scheme XI provides the desired compounds of formula (I) wherein

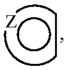

A and $R_3$ are defined hereinbefore, $R_4$ consists of the moiety B—C wherein B is (a) and C is the moiety (g) defined hereinbefore.

The preferred compounds of formula (I) of Scheme I wherein $R_4$ consists of the moiety B—C wherein B is (b) and C is the moiety (g) defined hereinbefore, can be prepared in analogous fashion by replacing the intermediate of formula (32) of Scheme XII with an appropriately substituted naphthyl intermediate.

Preferred processes for the preparation of compounds of formula (I) of Scheme I wherein $R_4$ consists of the moiety B—C wherein B is (a) or (b) and C is (d), (e) or (f) and

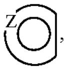

A, R, $R_3$, $R_5$, $R_6$, $R_7$, $R_8$, $R_9$, and $R_{10}$ are defined hereinbefore, also utilize acylation of the amide intermediate (36) of Scheme XII with an acylating agent of formula (19) of Scheme IV.

An alternate preferred process for the preparation of the compounds of formula (I) of Scheme I wherein $R_4$ consists of the moiety B—C wherein B is (a) and C is (g) defined hereinbefore, is shown in Scheme XIII.

Scheme XIII

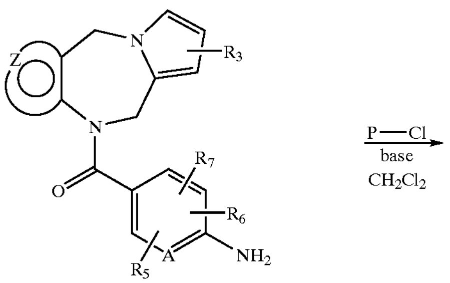

27

-continued

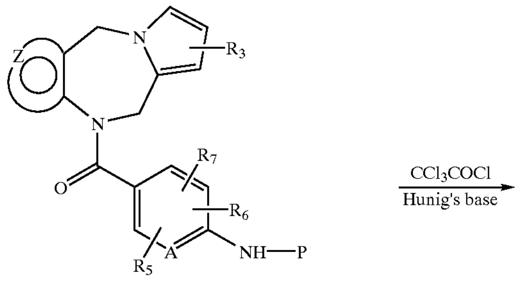

37

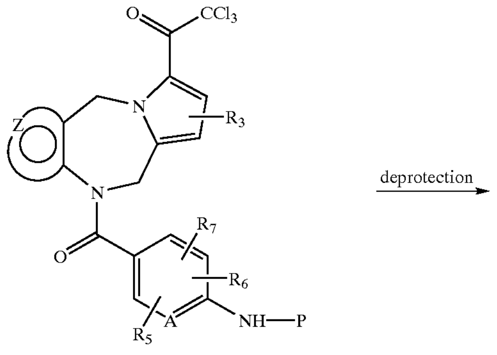

38

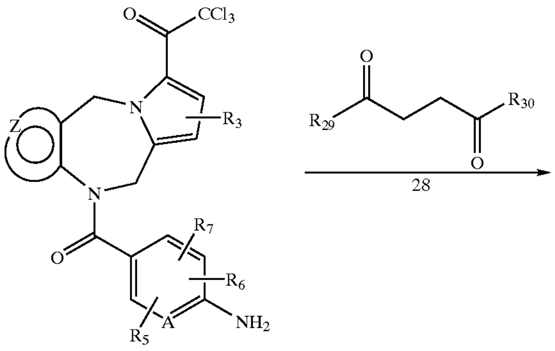

44

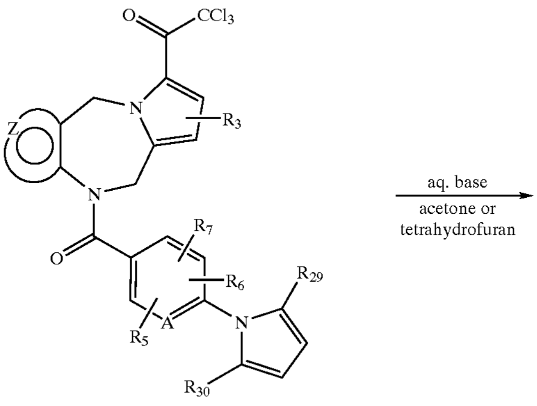

45

-continued

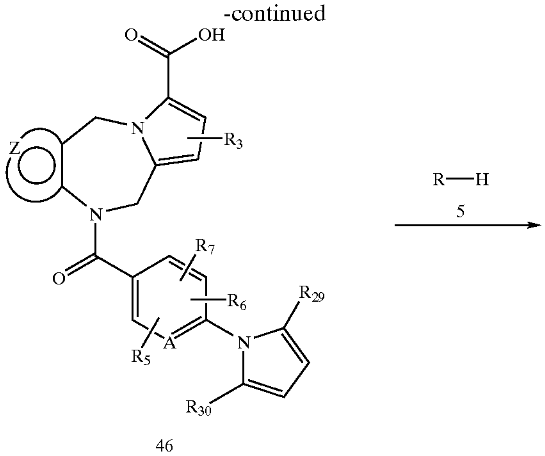

46

(I)

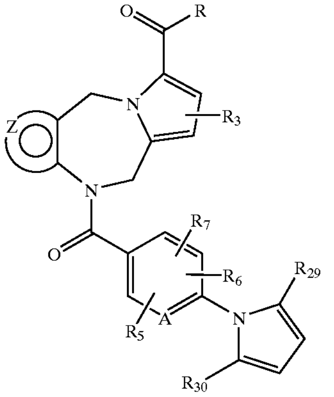

According to the above process a substituted tricyclic diazepine of formula (37) wherein

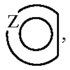

A, $R_3$, $R_5$, $R_6$ and $R_7$ are defined hereinbefore, carrying a protecting group such as a fluorenylalkoxycarbonyl group, preferably a fluorenylmethyloxycarbonyl (P═Fmoc) group is reacted with a perhaloalkanoyl halide preferably trichloroacetyl chloride, in the presence of an organic base such as N,N-diisopropylethyl amine (Hunig's base) or a tertiary amine such as triethylamine, in an aprotic organic solvent such as dichloromethane, at temperatures ranging from −10° C. to ambient, to provide the desired trichloroacetyl intermediate of formula (38). Subsequent deprotection of (38) is carried out by treatment with a solution of an organic base preferably piperidine, in an organic solvent such as N,N-dimethylformamide at ambient temperature to provide the desired aniline (44). Condensation of (44) with a 1,4-diketone of formula (28) either neat or in an aprotic organic solvent such as benzene or toluene, in the presence of a catalytic amount of a carboxylic acid preferably para-toluenesulfonic acid or acetic acid, with concomitant removal of water, at temperatures ranging from ambient to 100° C. or to the reflux temperature of the solvent according to the general procedure of Bruekelman et al., *J. Chem. Soc. Perkin Trans. I*,2801–2807 (1984) provides the desired intermediate of formula (45). Subsequent hydrolysis of the trichloroacetyl group with aqueous base such as sodium hydroxide, in an organic solvent such as acetone or tetrahydrofuran, at temperatures ranging from −10° C. to the reflux temperature of the solvent, yields the intermediate carboxylic acid of formula (46). Subsequent amidation provides the desired compounds of formula (I) wherein $R_4$ consists of the moiety B—C wherein B is (a) and C is (g), and

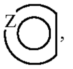

A, $R_3$, $R_5$, $R_6$, $R_7$, $R_{11}$ and $R_{12}$ are defined hereinbefore,

The required amidation of (46) can be effectively accomplished by treating said carboxylic acid with an activating reagent such as N,N-dicyclohexylcarbodiimide or 1-ethyl-3-(3-dimethylamino-propyl) carbodiimide hydrochloride in the presence of 1-hydroxybenzotriazole, followed by reaction of the activated intermediate with an appropriately substituted primary or secondary amine of formula (5) preferably in the presence of Hünig's base or a catalytic amount of 4-(dimethylamino)pyridine in an aprotic solvent such as dichloromethane, N,N-dimethylformamide or tetrahydrofuran, at temperatures ranging from −10° C. to ambient. Other coupling reagents known in the literature that have been used in the formation of amide bonds in peptide synthesis can also be used for the preparation of compounds of formula (I) wherein $R_4$ consists of the moiety B—C wherein B is (a) and C is (g), and

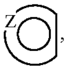

A, $R_3$, $R_5$, $R_6$, $R_7$, $R_{11}$ and $R_{12}$ are defined hereinbefore. The method of choice for the preparation of compounds of formula (I) from the intermediate carboxylic acid (465) is ultimately chosen on the basis of its compatibility with the

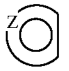

and $R_3$ groups, and its reactivity with the tricyclic diazepine of formula (6).

The desired compounds of formula (I) of Scheme XIII wherein $R_4$ consists of the moiety B—C wherein B is (b) and C is (g) can be prepared in analogous fashion by replacing the intermediate of formula (27) with an appropriately substituted naphthyl intermediate.

Alternatively, the intermediate acids of formula (35) of Scheme XII wherein

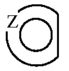

and $R_3$ are defined hereinbefore, can be obtained by reacting a tricyclic diazepine of formula (6) with an excess of an acylating agent preferably trifluoroacetic anhydride or trichloroacetyl chloride, in the presence of an inorganic base such as potassium carbonate or an organic base such as N,N-diisopropylethylamin, in an aprotic solvent such as N,N-dimethylformamide, followed by basic hydrolysis of the intermediate bis-trifluoroacetyl (trichloroacetyl) intermediate of formula (39, X═F or Cl) preferably with aqueous sodium hydroxide, in a protic organic solvent such as ethanol, at temperatures ranging from ambient to the reflux temperature of the solvent as exemplified in Scheme XIV.

Scheme XIV

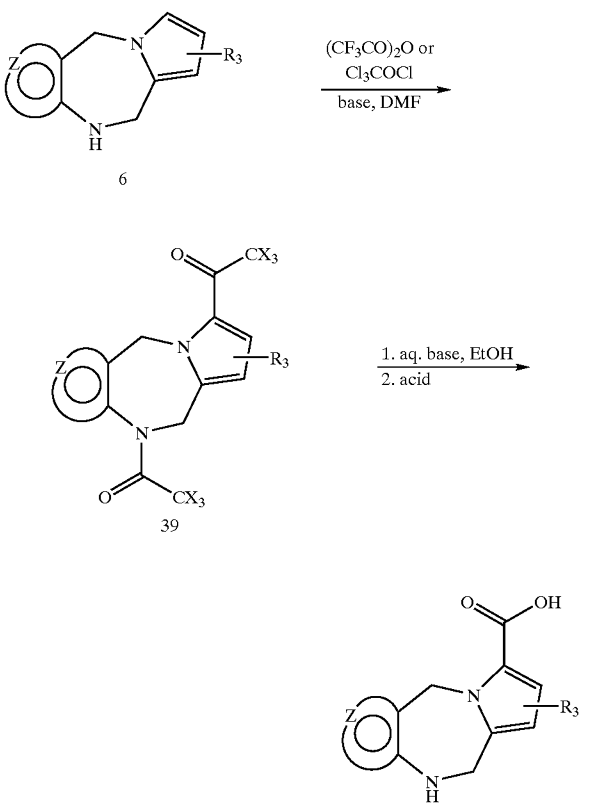

6
39
35

Preferred processes for the preparation of compounds of formula (I) of Scheme I wherein $R_4$ consists of the moiety B—C wherein B is (a) or (b) and C is (d), (e) or (f) and

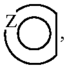,

A, R, $R_3$, $R_5$, $R_6$, $R_7$, $R_8$, $R_9$, and $R_{10}$ are defined hereinbefore, also utilize acylation of the amide intermediate (36) of Scheme XII with an acylating agent of formula (17) of Scheme IV, as shown in Scheme XV.

Scheme XV

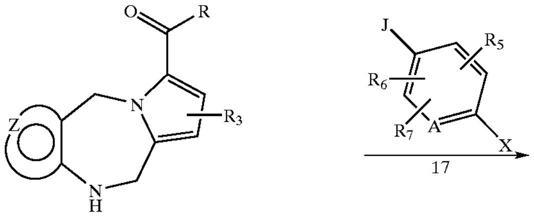
36
17

-continued

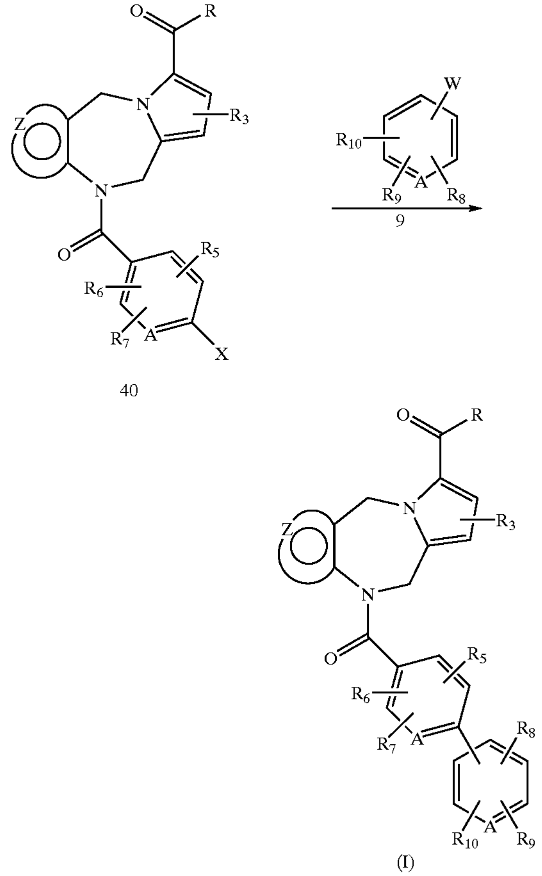
40
9
(I)

Alternatively, the preferred compounds of formula (I) of Scheme I wherein $R_4$ consists of the moiety B—C wherein B is (a) and C is (c) and

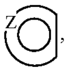,

A, R, $R_3$, $R_5$, $R_6$, $R_7$, $R_8$, $R_9$, and $R_{10}$ are defined hereinbefore, can be prepared by acylation of the amide intermediate (36) of Scheme XII with an acylating agent of formula (21) of Scheme VIII, as shown in Scheme XVI.

Scheme XVI

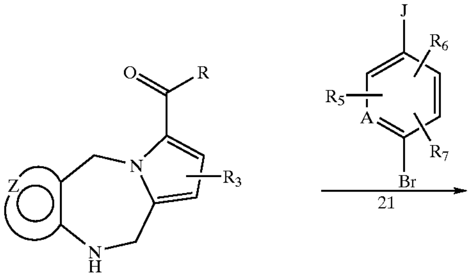
36
21

-continued

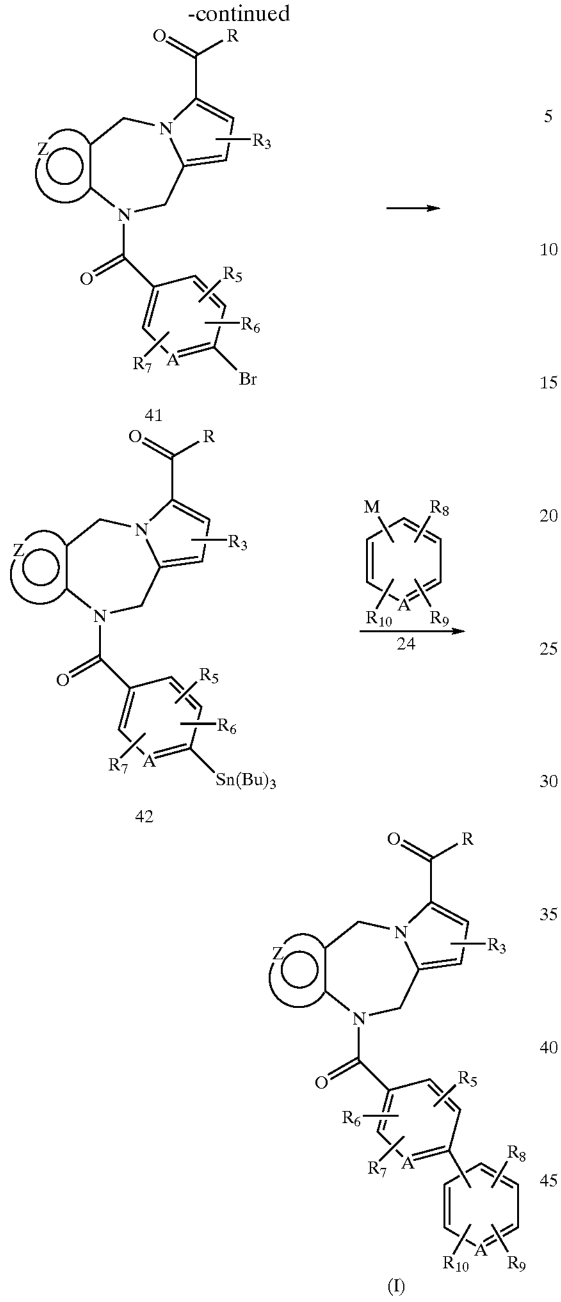

41

42

(I)

Alternatively, the preferred compounds of formula (I) of Scheme (I) wherein $R_4$ consists of the moiety B—C wherein B is (a) and C is (c) and

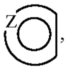,

A, R, $R_3$, $R_5$, $R_6$, $R_7$, $R_8$, $R_9$, and $R_{10}$ are defined hereinbefore, can be prepared by acylation of the amide intermediate (36) of Scheme XII with an acylating agent of formula (19) of Scheme IV, wherein J is hereinbefore defined, as shown in Scheme XVII.

Scheme XVII

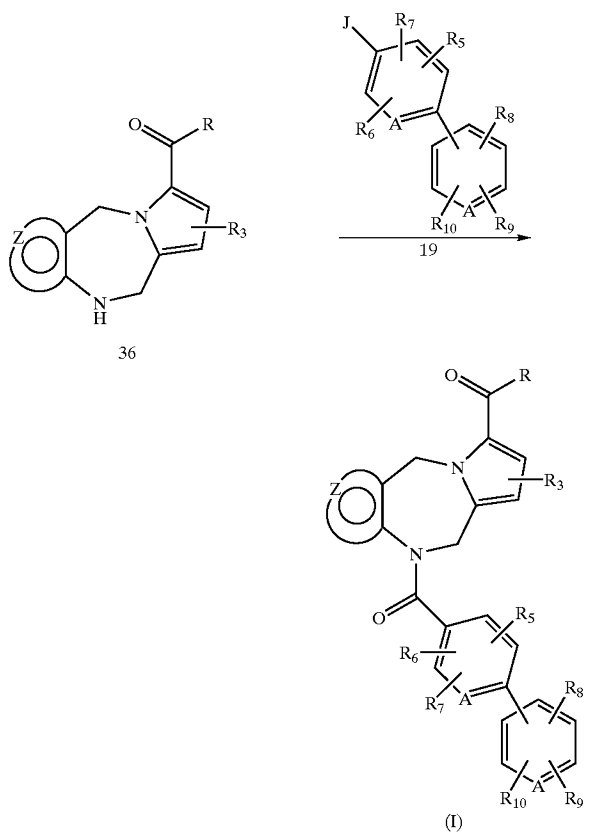

36

(I)

A preferred process for the preparation of compounds of formula (6) of Scheme III wherein

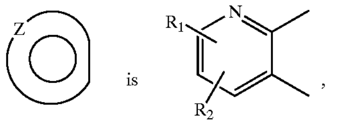

and $R_4$ consists of the moiety B—C wherein B is (a) or (b) and C is (d), (e) or (f), $R_3$ is hydrogen, and A, R, $R_5$, $R_6$, $R_7$, $R_8$, $R_9$, and $R_{10}$ are defined hereinbefore, is shown in Scheme XVIII.

Scheme XVIII

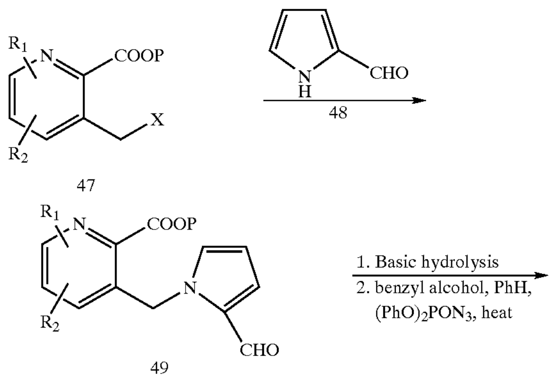

47

49

-continued

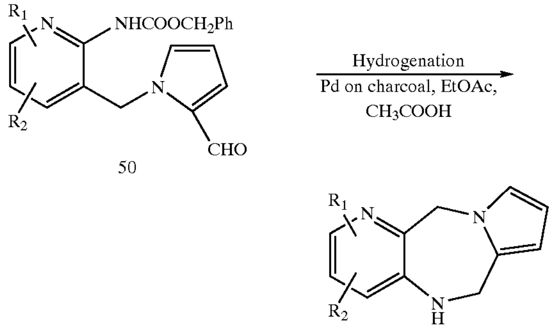

50

6

Thus, an appropriately substituted chloro(bromo) methylpyridine of formula (47, wherein X=Cl or Br, and P is a carboxylic acid protecting group, preferably P=alkyl), is condensed with a pyrrolo carboxaldehyde of formula (48, $R_3$=hydrogen) in the presence of an inorganic base, preferably sodium hydride, in an aprotic organic solvent, preferably N,N-dimethylformamide, at temperatures ranging from −10° C. to ambient, to yield the pyrrole derivative of formula (49, $R_3$=H). Subsequent basic hydrolysis of the ester (49) followed by Curtius rearrangement of the intermediate according to the general procedure of Kamikawa et al., *Biorg. Med. Chem.* 4, 1317 (1996) provides the benzylcarbamate of formula (50, $R_3$=H). Hydrogenation of (50) in an aprotic organic solvent such as ethyl acetate, in the presence of palladium-on-charcoal and a trace amount of an organic acid provides the tricyclic pyridodiazepine of formula (6, $R_3$=H) of Scheme III.

The subject compounds of the present invention were tested for biological activity according to the following procedures.

Vasopressin Binding in Chinese Hamster Ovary Cell Membranes Expressing Human Vasopressin V1a Subtype Receptors Receptor Source Chinese hamster ovary cells (CHO cells) stably transfected with the human vasopressin $V_{1a}$ subtype receptors were either obtained from BioSignal Inc., 1744 rue Williams, Montreal, Quebec, Canada or obtained from M. Thibonnier, Case Western Reserve University School of Medicine, Cleveland, Ohio.

A. Passaging and Amplification of Cells

CHO cells transfected with the human vasopressin $V_{1a}$ subtype receptors obtained from M. Thibonnier (pZeoSV vector) are allowed to grow to confluency (approx. >90%) in T-150 flasks under sterile conditions, in a cell culture medium of F-12 Nutrient Mixture (HAM) with L-glutamine (Gibco Cat. #11765-054) containing 15 mM HEPES (Gibco Cat. #15630-080), 1% antibiotic/antimycotic (add 5 mL 100×, Gibco Cat. #15240-062 per 500 mL F-12), 250 μg/mL Zeocin (add 1.25 mL of 100 mg/mL Invitrogen R-250-01 per 500 mL F-12) and 10% Fetal Bovine Serum (Qualified, heat inactivated, Gibco Cat. #16140-063). The medium is removed by aspiration and the cells are washed with 10 mL of Hank's Balanced Salt solution (Gibco Cat. #14175-095). The salt solution is removed by aspiration and the cells are trypsinized with 5 mL of trypsin-EDTA (0.05% trypsin, 0.53 mM EDTA-4Na, Gibco Cat. #25300-070) for 1 min. The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh cell culture medium (e.g., into 25 mL per T-150 flask), and mixed gently. The cells are incubated at 37° C. in 5% $CO_2$. The medium is changed at 3 to 4 days interval (or as appropriate). The cells grow to confluency (approx. >75%–95%) within 7–8 days. All steps are done under sterile conditions.

B. Membrane Preparation

The cells are washed twice gently with Hank's Balanced Salt solution (e.g,. use 10 mL per T-150 flask). The excess is removed and the cells are bathed for 15–30 min. in an enzyme-free Cell Dissociation Buffer (e.g. use 8 mL Hank's Based, Gibco Cat. #13150-016 per T-150 flask) until the cells are loosened. The contents are transferred to centrifuge tubes (50 mL) kept in an ice bath. All subsequent steps are done at 4° C. The tubes are centrifuged at 300×g for 15 min (1380 rpm on SORVAL, Model RT6000D, using the rotor for 50 mL tubes). The supernatant is discarded and the cells suspended in homogenizing buffer(10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with Polytron at setting 6 for 10 sec. The homogenate is transferred into a Potter-Elvjehm homogenizer and homogenized with 3 strokes. The homogenate is centrifuged at 1500×g for 10 min at 4° C. (3100 rpm using SORVAL, model RT6000D, using the rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernantant is discarded and the pellet suspended in 3 to 4 mL of Tris buffer (50 mM TRIS—HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay

In wells of a 96-well format microtiter plate, is added 90, 110 or 130 μL (to make up a final volume of 200 μL) of assay buffer containing 50 mM of Tris-HCl (pH 7.4), BSA (heat inactivated, protease-free), 0.1% of 5 mM $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 pL of unlabeled Manning ligand (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. 20 μL of 50% DMSO is added for Manning and other peptide ligands and the assay buffer volume is adjusted accordingly. To each well is added 50 μL of frozen membrane suspension thawed immediately prior to use and diluted in the assay buffer to the required concentration (equivalent to 25 to 50 μg of protein/well as needed). 20 μL of 8 nM [$^3$H]Manning ligand in the assay buffer, prepared just before use, is added, and incubated at room temperature for 60 min. shaking the plate on a mechanical shaker for the first 15 min. The incubation is stopped by rapid filtration of the the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Vasopressin Binding in Chinese Hamster Ovary Cell Membranes Expressing Human Vasopressin $V_2$ Subtype Receptors Receptor Source Chinese Hamster Ovary (CHO) cells stably transfected with the human $V_2$ subtype receptors were obtained from M. Thibonnier, Case Western Reserve University School of Medicine, Cleveland, Ohio.

A. Passaging and Amplification of Cells

CHO cells transfected with the human vasopressin $V_2$ subtype receptors obtained from M. Thibonnier (pZeoSV vector) are allowed to grow to confluency (approx. >90%) in T-150 flasks under sterile conditions, in a cell culture medium ofF-12 Nutrient Mixture (HAM) with L-glutamine (Gibco Cat. #11765-054) containing 15 mM HEPES (Gibco Cat. #15630-080), 1% antibiotic/antimycotic (add 5 mL 100×, Gibco Cat. #15240-062 per 500 mL F-12), 250 μg/mL Zeocin (add 1.25 mL of 100 mg/mL Invitrogen R-250-01 per 500 mL F-1 2) and 10% Fetal Bovine Serum (Qualified, heat inactivated, Gibco Cat. #16140-063). The medium is removed by aspiration and the cells washed with 10 mL of Hank's Balanced Salt solution (Gibco Cat. #14175-095). The salt solution is removed by aspiration and the cells trypsinized with 5 mL of trypsin-EDTA (0.05% trypsin, 0.53 mM EDTA-4Na, Gibco Cat. #25300-070) for 1 min. The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh Cell Culture medium (e.g. into 25 mL per T-150 flask), and mixed gently. The cells are incubated at 37° C. in 5% $CO_2$. The medium is changed at 3 to 4 day interval (or as appropriate). The cells grow to confluency (approx. >75%–95%) within 7–8 days. All steps are done under sterile conditions.

B. Membrane Preparation

The cells are washed twice gently with Hank's Balanced Salt solution (e.g. use 10 mL per T-150 flask). The excess solution is removed and the cells bathed for 15–30 min. in an enzyme-free Cell Dissociation Buffer (e.g. use 8 mL Hank's Based, Gibco Cat. # 13150-016 per T-150 flask) until cells are loosened. The contents are transferred to centrifuge tubes (50 mL) kept in ice bath. All subsequent steps are done at 4° C. The tubes are centrifuged at 300×g for 15 min (1380 rpm on SORVAL, Model RT6000D, using the rotor for 50 mL tubes). The supernatant is discarded and the cells suspended in homogenizing buffer (10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with Polytron at setting 6 for 10 sec. The homogenate is transferred into a Potter-Elvjehm homogenizer and homogenized with 3 strokes. The homogenate is centrifuged at 1500×g for 60 min at 4° C. (3100 rpm using SORVAL, model RT6000D, using the rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernantant is discarded and the pellet suspended in 3 to 4 mL of Tris buffer (50 mM TRIS—HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70. ° C.

C. Radioligand Binding Assay

In wells of a 96-well format microtiter plate, is added 90, 110 or 130 μL (to make up a final volume of 200 μL) of assay buffer containing 50 mM of Tris-HCl (pH 7.4), BSA (heat inactivated, protease-free), 5 mM of 0.1% $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 μL of unlabeled arginine vasopressin (AVP) (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. For vasopressin and other peptide ligands 20 μL of 50% DMSO is added and the assay buffer volume is adjusted accordingly.

To each well is added 50 μL of frozen membrane suspension thawed immediately prior to use and diluted in assay buffer to the required concentration (equivalent to 25 to 50 μg of protein/well as needed). 20 μL of 8 nM [$^3$H]arginine vasopressin ligand in the assay buffer, prepared just before use is added and incubated at room temperature for 60 min. shaking the plate on a mechanical shaker for the first 15 min. The incubation is stopped by rapid filtration of the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Oxytocin Binding in Chinese Hamster Ovary Cell Membranes Expressing Human Oxytocin Receptors Receptor Source Chinese Hamster Ovary (CHO) cells stably transfected with the human oxytocin receptor (cf. Tanizawa et al., U.S. Pat. No. 5,466,584 (1995) to Rohto Pharmaceutical Co. Ltd., Osaka, Japan) were obtained from M. Thibonnier, Case Western Reserve University School of Medicine, Cleveland, Ohio.

A. Passaging and Amplification of Cells

CHO cells transfected with the human oxytocin receptors obtained from M. Thibonnier (pcDNA3.1 vector) are allowed to grow to confluency (approx. >90%) in T-150 flasks under sterile conditions, in a cell culture medium of F-12 Nutrient Mixture (HAM) with L-glutamine (Gibco Cat. #11765-054) containing 15 mM HEPES (Gibco Cat. #15630-080), 1% antibiotic/antimycotic (add 5 mL 100×, Gibco Cat. #15240-062 per 500 mL F-12), 400 μg/mL of Geneticin (add 4 mL of 50 mg/mL per 500 mL F-12) and 10% Fetal Bovine Serum (Qualified, heat inactivated, Gibco Cat. #16140-063). The medium is removed by aspiration and the cells are washed with 10 mL of Hank's Balanced Salt solution (Gibco Cat. #14175-095). The salt solution is removed by aspiration and the cells trypsinized with 5 mL of trypsin-EDTA (0.05% trypsin, 0.53 mM EDTA-4Na, Gibco Cat. #25300-070) for 1 min. The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh Cell Culture medium (e.g. into 25 mL per T-150 flask), and mixed gently. The cells are incubated at 37° C. in 5% $CO_2$. The medium is changed at 3 to 4 days interval (or as appropriate). The cells grow to confluency (approx. >75%–95%) within 7–8 days. All steps are done under sterile conditions.

B. Membrane Preparation

The cells are washed twice gently with Hank's Balanced Salt solution (e.g., use 10 mL per T-1 50 flask). The excess solution is removed and the cells bathed for 15–30 min. in an enzyme-free Cell Dissociation Buffer (e.g., use 8 mL Hank's Based, Gibco Cat. #13150-016 per T-150 flask) until cells are loosened. The contents are transferred to centrifuge tubes (50 mL size) kept in ice bath. All subsequent steps are done at 4° C. The tubes are centrifuged at 300×g for 15 min (1380 rpm on SORVAL, Model RT6000D, using rotor for 50 mL tubes). The supernatant is discarded and the cells suspended in homogenizing buffer (10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with a Polytron at setting 6 for 10 sec. The homogenate is transferred into a Potter-Elvjehm homogenizer and homogenized with 3 strokes. The homogenate is centrifuged at 1500×g for 10 min at 4° C. (3100 rpm using SORVAL, model RT6000D, using rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernantant is discarded and the pellet suspended in 3 to 4 mL of Tris buffer (50 mM TRIS—HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay

In wells of a 96-well format microtiter plate, is added 90, 110 or 130 μL (to make up a final volume of 200 μL) of assay buffer containing 50 mM of Tris-HCl (pH 7.4), BSA (heat inactivated, protease-free), 5 mM of 0.1% $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 μL of unlabeled oxytocin (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. For oxytocin and other peptide ligands, 20 μL of 50% DMSO is added and the assay buffer volume is adjusted accordingly.

To each well is added 50 μL of frozen membrane suspension thawed immediately prior to use and diluted in assay buffer to the required concentration (equivalent to 25 to 50 μg of protein/well as needed). 20 μL of 8 nM [$^3$H]oxytocin in the assay buffer, prepared just before use is added and incubated at room temperature for 60 min. shaking the plate on a mechanical shaker for the first 15 min. The incubation is stopped by rapid filtration of the plate contents followed by washing with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Binding data is either reported as percent inhibition at a certain concentration or if an $IC_{50}$ was calculated, as a nanomolar concentration. The results of these tests on representative compounds of this invention are shown in Table I.

TABLE 1

Binding to membranes of Chinese Hamster Ovary (CHO) cell line stably transfected with human vasopressin $V_{1a}$ receptor subtype, human vasopressin $V_2$ receptor subtype and human oxytocin receptor

| Example | OT % inhibition @ 100 nM ($IC_{50}$, nM)* | $V_{1a}$ % inhibition @ 100 nM ($IC_{50}$, nM)* | $V_2$ % inhibition @ 100 nM ($IC_{50}$, nM)* |
|---|---|---|---|
| 1 | (1.37) | (1388) | (610) |
| 2 | (3.09) | (789.63) | (633.32) |
| 3 | (6.53) | 7 | 13 |
| 4 | (3.43) | (1431) | (617) |
| 5 | (35.80) | (2722) | (1192) |
| 6 | (25.06) | (2413) | (1388) |
| 7 | (30.7) | −2 | 16 |
| 8 | (7.55) | (1970) | (769) |
| 9 | (26.67) | (2007) | (1229) |
| 10 | (5.31) | (1802) | (2221) |
| 11 | (3.66) | (1368) | (356) |
| 12 | (4.27) | (1615) | (763) |
| 13 | (9.16) | (1205) | (990) |
| 14 | (1.9) | (143.89) | (205.43) |
| 15 | 101 | 59 | 74 |
| 16 | 101 | 68 | 51 |
| 17 | (1.03) | (227) | (144) |
| 18 | 36 | 0 | −5 |
| 19 | 27 | 1 | 3 |
| 20 | (1.09) | (3104) | (226.81) |
| 21 | (1.73) | (376) | (311) |
| 22 | (1.47) | (227) | (1140) |
| 23 | (4.09) | (1080) | (451) |
| 25 | 20 | 5 | 21 |
| 26 | (55.8) | (139.6) | (11.3) |
| 36 | (7.95) | (1513) | (2073) |
| 37 | 53 | 6 | 7 |
| 39 | (3.0) | (759.) | (383.1) |
| 40 | 93 | 13 | 25 |
| 41 | 71 | 12 | 35 |
| 42 | 89 | 49 | 27 |
| 43 | 75 | 1 | 27 |
| 44 | 83 | 17 | 13 |
| 45 | 87 | 57 | 9 |
| 46 | 97 | 53 | 14 |
| 47 | 55 | 12 | 16 |
| 48 | 79 | 7 | 11 |
| 49 | 81 | 1 | 21 |
| 50 | 83 | 52 | 16 |
| 52 | 36 | 7 | 3 |

*Binding in Chinese Hamster Ovary cell membranes expressing human vasopressin $V_{1a}$ and $V_2$ subtype receptors and human oxytocin receptors The following examples are presented to illustrate rather than limit the scope of this invention.

EXAMPLE 1

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid bis-(2-hydroxy-ethyl)-amide Step A. 4-Bromo-3-methylbenzoic acid methyl ester To a suspension of 4-bromo-3-methylbenzoic acid (10.0 g, 46.5 mmol) in methanol (125 mL) was added concentrated sulfuric acid (1 mL). The reaction was heated at reflux overnight with a homogeneous solution obtained after several minutes of heating. After cooling, the methanol was removed in vacuo and the residue was dissolved in dichloromethane and washed with saturated aqueous sodium bicarbonate. The organic phase was dried over anhydrous sodium sulfate, filtered and concentrated in vacuo to give 10.2 g of title compound as a brown solid, m.p. 41–43° C.

$^1$H NMR (DMSO-$d_6$, 400 MHz): δ 2.39 (s, 3H), 3.85 (s, 3H), 7.64–7.72 (m, 2H), 7.88–7.89 (m, 1H).

MS [EI, m/z]: 228 $[M]^+$.

Anal. Calcd. for $C_9H_9BrO_2$: C 47.19, H 3.90. Found: C 47.22, H 3.80.

Step B. 2-Methyl-2'-trifluoromethyl-[1,1'-biphenyl]-4-carboxylic acid methyl ester A mixture of 4-bromo-3-methylbenzoic acid methyl ester of Step A (2.0 g, 8.7 mmol), 2-trifluoromethyl-phenyl boronic acid (1.65 g, 8.7 mmol) and sodium carbonate (4.1 g, 38.7 mmol) in toluene:ethanol:water (50 mL:25 mL: 25 mL) was purged with nitrogen for 1 hour. After addition of the tetrakis(triphenylphosphine) palladium(0) catalyst (0.50 g, 0.43 mmol, the reaction was heated at 100° C. overnight. The cooled reaction mixture was filtered through Celite and the cake washed with ethyl acetate. The organic layer was washed with water, dried over anhydrous sodium sulfate, filtered and concentrated in vacuo to give a brown oil. Purification by flash chromatography with a solvent gradient of 25% to 50% dichloromethane in hexane provided 2.0 g of the title compound as a colorless oil.

$^1$H NMR (DMSO-$d_6$, 400 MHz): δ 2.03 (s, 3H), 3.88 (s, 3H), 7.26 (d, 1H), 7.34 (d, 1H), 7.66 (t, 1H), 7.75 (t, 1H), 7.81–7.83 (m, 1H), 7.86–7.88 (m, 1H), 7.90–7.91 (m, 1H).

MS [(+)ESI, m/z]: 312 $[M+NH_4]^+$.

Anal. Calcd. for $C_{16}H_{13}F_3O_2$: C 65.31, H 4.45. Found: C 64.92, H 4.54.

Step C. 2-Methyl-2'-trifluoromethyl-[1,1'-biphenyl]-4-carboxylic acid

To a solution of 2-methyl-2'-trifluoromethyl-[1,1'-biphenyl]-4-carboxylic acid methyl ester of Step B (1.9 g, 6.5 mmol) in tetrahydrofuran (30 mL) was added 1 N sodium hydroxide (13 mL, 13 mmol). The reaction mixture was heated at reflux overnight, then cooled and acidified with 2 N hydrochloric acid. The aqueous layer was extracted with ethyl acetate and the combined extracts were dried over anhydrous sodium sulfate, filtered and concentrated in vacuo to give 1.65 g of the title compound as a white solid, m.p. 171–174° C.

NMR (DMSO-$d_6$, 400 MHz): δ 2.02 (s, 3H), 7.23 (d, 1H), 7.34 (d, 1H), 7.65 (t, 1H), 7.75 (t, 1H), 7.79–7.81 (m, 1H), 7.86–7.89 (m, 2H), 13.00 (broad s, 1H).

MS [(−) ESI, m/z]: 279 $[M-H]^-$.

Anal. Calcd. for $C_{15}H_{11}F_3O_2$: C 64.29, H 3.96. Found: C 64.26, H 3.80.

Step D. (10,11-Dihydro-5H-pyrrolo[2,1-c][1,4]benzodiazepin-10-yl)-[(2-methyl-2'-trifluoromethyl-[1,1'-biphenyl]-4-yl]methanone A suspension of 2-methyl-2'-trifluoromethyl-[1,1'-biphenyl]-4-carboxylic acid of Step C (0.50 g, 1.78 mmol) in thionyl chloride (3 mL) was heated at reflux for 90 minutes. After cooling, the thionyl chloride was removed in vacuo and the residue dissolved in toluene. The solution was concentrated in vacuo to yield the crude acid chloride as a brown oil. The acid chloride was dissolved in dichloromethane (5 mL) and slowly added to a solution of 10,11-dihydro-5H-pyrrolo[2,1-c][1,4]benzodiazepine (0.49 g, 2.66 mmol) and N,N-diisopropylethyl amine (0.68 mL, 3.90 mmol) in dichloromethane (15 mL). After stirring for 2 hours, the reaction was quenched with water. The organic layer was sequentially washed with 1 N hydrochloric acid, 1 N sodium hydroxide and brine, dried over anhydrous sodium sulfate, filtered and concentrated in vacuo to give a yellow foam. Purification by flash chromatography using a solvent gradient of 15 to 25% ethyl acetate in hexane gave a white foam which was crystallized by sonication from ethanol/hexane to provide the title compound (0.55 g) as a white solid, m.p. 127–130° C.

$^1$H NMR (DMSO-$d_6$, 400 MHz): δ 1.86 (s, 3H), 4.80–5.40 (br, 4H), 5.93–5.98 (m, 2H), 6.85 (t, 1H), 6.91–6.96 (m, 2H), 7.03–7.05 (m, 1H), 7.10–7.14 (m, 1H), 7.19–7.24 (m, 2H), 7.29 (s, 1H), 7.47–7.49 (m, 1H), 7.61 (t, 1H), 7.70 (t, 1H), 7.81 (d, 1H).

MS [EI, m/z]: 446 $[M]^+$.

Anal. Calcd. for $C_{27}H_{21}F_3N_2O$: C 72.64, H 4.74, N 6.27. Found: C 72.48, H 4.57, N 6.16.

Step E. 2,2,2-Trichloro-1-(10-{[2-methyl-2'-trifluoromethyl-[1,1'-biphenyl]-4-yl]carbonyl}-10,11-dihydro-5H-pyrrolo[2,1-c][1,4]benzodiazepin-3-yl) ethanone To a solution of (10,11-dihydro-5H-pyrrolo[2,1-c][1,4]benzodiazepin-10-yl)-[(2-methyl-2'-trifluoromethyl-[1,1'-biphenyl]-4-yl]methanone of Step D (1.87 g, 4.19 mmol) in dichloromethane (20 mL) was added N,N-diisopropylethylamine (1.46 mL, 8.38 mmol) followed by the slow addition of trichloroacetyl chloride (1.45 mL, 13.0 mmol). The reaction mixture was stirred overnight at room temperature, and then quenched with water. The organic phase was washed with 0.1 N hydrochloric acid followed by water, then dried over anhydrous sodium sulfate, filtered and concentrated in vacuo to give a green oil. Purification by flash chromatography on silica gel using a solvent system of 20% ethyl acetate in hexane provided 2.2 g of title product as a pale, yellow foam.

$^1$H NMR (DMSO-$d_6$, 400 MHz): δ 1.84 (s, 3H), 5.25 (br, 2H), 5.97 (br, 2H), 6.37 (d, 1H), 6.89–6.92 (m, 2H), 7.02–7.04 (m, 1H), 7.06–7.10 (m, 1H), 7.15–7.22 (m, 2H), 7.28 (s, 1H), 7.41–7.46 (m, 2H), 7.58 (t, 1H), 7.67 (t, 1H), 7.79 (d, 1H).

MS [(+)APCI, m/z]: 591 $[M+H]^+$.

Anal. Calcd. for $C_{29}H_{20}Cl_3F_3N_2O_2$+0.20 $C_4H_8O_2$+0.80$H_2O$: C 57.37, H 3.75, N 4.49.

Found: C 57.06, H 3.39, N 4.50.

Step F. 10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid To a solution of 2,2,2-trichloro-1-(10-{[2-methyl-2'-trifluoromethyl-[1,1'-biphenyl]-4-yl]carbonyl}-10,11-dihydro-5H-pyrrolo[2,1-c][1,4]benzodiazepin-3-yl) ethanone of Step E (2.3 g, 3.9 mmol) in acetone (20 mL) was added 2.5 N sodium hydroxide (3.1 mL, 7.8 mmol). After stirring overnight, the reaction mixture was acidified with 2 N hydrochloric acid (4.3 mL, 8.6 mmol) and then concentrated in vacuo. The residue was partitioned between ethyl acetate and water. The organic layer was dried over anhydrous sodium sulfate, filtered and concentrated in vacuo to give a brown solid. Trituration with diethyl ether/hexane provided the title compound (1.32 g) as a white solid, m.p. 233–235° C.

$^1$H NMR (DMSO-$d_6$, 400 MHz): δ 1.84 (s, 3H), 5.17 (br, 2H), 5.94 (br, 2H), 6.10–6.11 (m, 1H), 6.76 (d, 1H), 6.85–6.91 (m, 2H), 7.00–7.06 (m, 2H), 7.12–7.16 (m, 1H), 7.21 (d, 1H), 7.25 (s, 1H), 7.32–7.34 (m, 1H), 7.59 (t, 1H), 7.68 (t, 1H), 7.79 (d, 1H), 12.33 (br, 1H).

MS [(+)ESI, m/z]: 491 $[M+H]^+$.

Anal. Calcd. for $C_{28}H_{21}F_3N_2O_3$: C 68.57, H 4.32, N 5.71. Found: C 68.39, H 4.25, N 5.64.

Step G. 10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic Acid bis-(2-hydroxy-ethyl)-amide To a solution of 10-[(2-methyl-2'-trifluoromethyl-[1,1'-biphenyl]-4-yl)carbonyl]-10,11-dihydro-5H-pyrrolo[2,1-c][1,4]benzodiazepine-3-carboxylic acid of Step F (0.50 g, 1.02 mmol) and diethanolamine (0.13 g, 1.24 mmol) in N,N-dimethylformamide (4 mL) was added 1-hydroxybenzotriazole (0.15 g, 1.11 mmol) and 1-[3-(dimethylamino)propyl]-3-ethyl carbodiimide hydrochloride (0.22 g, 1.15 mmol) followed by N,N-diisopropylethyl amine (0.27 mL, 1.55 mmol). The reaction mixture was stirred overnight, then diluted with ethyl acetate and washed with water and saturated aqueous sodium bicarbonate. The organic phase was then dried over anhydrous sodium sulfate, filtered and concentrated in vacuo to give an orange oil. Purification by flash chromatography on silica gel using a solvent system of 5% methanol in chloroform provided the title compound (0.46 g) as a white foam.

$^1H$ NMR (DMSO-$d_6$, 400 MHz): δ 1.83 (s, 3H), 3.55 (br, 8H), 4.82 (t, 2H), 5.15 (br, 2H), 5.33 (s, 2H), 6.02 (d, 1H), 6.29 (d, 1H), 6.85–6.90 (m, 2H), 6.99–7.06 (m, 2H), 7.13 (t, 1H), 7.21 (d, 1H), 7.25 (s, 1H), 7.35–7.37 (m, 1H), 7.58 (t, 1H), 7.68 (t, 1H), 7.79 (d, 1H).

MS [(+)ESI, m/z]: 578 $[M+H]^+$.

Anal. Calcd. for $C_{32}H_{30}F_3N_3O_4$+0.60$H_2O$: C 65.32, H 5.34, N 7.14. Found: C 64.92, H 5.44, N 7.07.

EXAMPLE 2

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid (2,3-dihydroxy-propyl)-methyl-amide To a solution of 10-[(2-methyl-2'-trifluoromethyl-[1,1'-biphenyl]-4-yl)carbonyl]-10,11-dihydro-5H-pyrrolo[2,1-c][1,4]benzodiazepine-3-carboxylic acid of Example 1, Step F (1.2 g, 2.44 mmol) and 3-methylamino-1,2-propanediol (0.32 g, 3.04 mmol) in N,N-dimethyl formamide (10 mL) was added 1-hydroxybenzotriazole (0.36 g, 2.66 mmol) and 1-[3-(dimethylamino)propyl]-3-ethylcarbodiimide hydrochloride (0.52 g, 2.71 mmol) followed by N,N-diisopropylethyl amine (0.64 mL, 3.67 mmol). The reaction mixture was stirred overnight, diluted with ethyl acetate and washed with water and saturated aqueous sodium bicarbonate. The organic phase was then dried over anhydrous sodium sulfate, filtered and concentrated in vacuo to give a brown foam. Purification by flash chromatography using a solvent system of 5% methanol in chloroform gave a white foam, which was crystallized from ethyl acetate to provide 1.15 g of title product as a white solid, m.p. 169–172° C.

$^1H$ NMR (DMSO-$d_6$, 400 MHz): δ 1.83 (s, 3H), 3.08 (br, 3H), 3.34 (br, 2H), 3.51 (br, 2H), 3.78 (br, 1H), 4.61 (br, 1H), 4.89 (br, 1H), 5.15 (br, 2H), 5.38 (br, 2H), 6.02–6.03 (m, 1H), 6.32 (d, 1H), 6.86–6.91 (m, 2H), 6.99–7.07 (m, 2H), 7.14 (t, 1H), 7.21 (d, 1H), 7.25 (s, 1H), 7.37–7.39 (m, 1H), 7.58 (t, 1H), 7.68 (t, 1H), 7.79 (d, 1H).

MS [(+)APCI, m/z]: 578 $[M+H]^+$.

Anal. Calcd. for $C_{32}H_{30}F_3N_3O_4$: C 66.54, H 5.24, N 7.27. Found: C 66.14, H 5.25, N 7.04.

EXAMPLE 3

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid (2-hydroxy-1,1-bis-hydroxymethyl-ethyl)-amide To a solution of 10-[(2-methyl-2'-trifluoromethyl-[1,1'-biphenyl]-4-yl)carbonyl]-10,11-dihydro-5H-pyrrolo[2,1-c][1,4]benzodiazepine-3-carboxylic acid of Example 1, Step F (0.50 g, 1.02 mmol) and 2-amino-2-hydroxymethyl-1,3-propanediol (0.15 g, 1.24 mmol) in N,N-dimethylformamide (5 mL) was added 1-hydroxybenzotriazole (0.15 g, 1.11 mmol) and 1-[3-(dimethylamino)propyl]-3-ethylcarbodiimide hydrochloride (0.22 g, 1.15 mmol) followed by N,N-diisopropylethyl amine (0.27 mL, 1.55 mmol). The reaction mixture was stirred overnight, diluted with ethyl acetate and washed with water and saturated aqueous sodium bicarbonate. The organic phase was then dried over anhydrous sodium sulfate, filtered and concentrated in vacuo to give a brown oil. Purification by flash chromatography using a solvent system of 5% methanol in chloroform provided the title product, which was redissolved in dichloromethane and evaporated to dryness in vacuo to a white foam (0.19 g).

$^1H$ NMR (DMSO-$d_6$, 400 MHz): δ 1.84 (s, 3H), 3.67 (d, 6H), 4.76 (t, 3H), 5.15 (br, 2H), 5.82 (br, 2H), 6.05 (d, 1H), 6.58 (d, 1H), 6.82–6.84 (m, 1H), 6.89–6.91 (m, 2H), 6.98–7.03 (m, 2H), 7.10–7.14 (m, 1H), 7.21 (d, 1H), 7.24 (s, 1H), 7.33–7.35 (m, 1H), 7.59 (t, 1H), 7.68 (t, 1H), 7.80 (d, 1H).

MS [(+)APCI, m/z]: 594 $[M+H]^+$.

Anal. Calcd. for $C_{32}H_{30}F_3N_3O_5$+0.14 $CH_2Cl_2$+0.25$H_2O$: C 63.28, H 5.09, N 6.89.

Found: C 62.94, H 5.22, N 6.71.

EXAMPLE 4

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid methyl-((2S,3R,4R,5R)-2,3,4,5,6-pentahydroxy-hexyl)-amide To a solution of 10-[(2-methyl-2'-trifluoromethyl-[1.1°-biphenyl]-4-yl)carbonyl]-10,11-dihydro-5H-pyrrolo[2,1-c][1,4]benzodiazepine-3-carboxylic acid of Example 1, Step F (1.0 g, 2.04 mmol), and N-methyl-D-glucamine (0.48 g, 2.46 mmol) in N,N-dimethylformamide (8 mL) was added 1-hydroxybenzotriazole (0.30 g, 2.22 mmol) and 1-[3-(dimethylamino)propyl]-3-ethylcarbodiimide hydrochloride (0.43 g, 2.24 mmol) followed by N,N-diisopropylethyl amine (0.55 mL, 3.09 mmol). The reaction mixture was stirred overnight, diluted with ethyl acetate and washed with water and saturated aqueous sodium bicarbonate. The organic phase was then dried over anhydrous sodium sulfate, filtered and concentrated in vacuo to give a yellow foam. Purification by flash chromatography on silica gel using a solvent system of 10% methanol in chloroform provided 1.08 g of title compound as a white foam.

$^1H$ NMR (DMSO-$d_6$, 400 MHz): δ 1.84 (s, 3H), 3.06 (br, 3H), 3.35–3.57 (m, 7H), 3.92 (br, 1H), 4.31–4.39 (m, 3H), 4.49–4.50 (m, 1H), 4.89 (d, 1H), 5.15 (br, 2H), 5.38 (s, 2H), 6.02 (br, 1H), 6.34 (br, 1H), 6.85–6.91 (m, 2H), 6.99–7.06 (m, 2H), 7.14 (t, 1H), 7.21 (d, 1H), 7.25 (s, 1H), 7.39–7.41 (m, 1H), 7.58 (t, 1H), 7.68 (t, 1H), 7.79 (d, 1H).

MS [(+)APCI, m/z]: 668 $[M+H]^+$.

Anal. Calcd. for $C_{35}H_{36}F_3N_3O_7$+0.38 $C_4H_8O_2$: C 62.56, H 5.61, N 5.99. Found: C 61.22, H 5.57, N 5.80.

EXAMPLE 5

(2S)-3-{4-[(10-{[2-Methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}propane-1,2-diol Step A. 4-[[10,11-Dihydro-10-[[2-methyl-2'-trifluoromethyl-[1,1'-biphenyl]-4-yl]carbonyl]-5H-pyrrolo[2,1-c][1,4]benzodiazepin-3-yl]carbonyl]-1-piperazine carboxylic acid, tert-butyl ester 10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid of Example 1, Step F (1.0 g, 2.04 mmol), 1-(tert-butoxycarbonyl)piperazine (0.46 g, 2.47 mmol) and 1-hydroxybenzotriazole monohydrate (0.30 g, 2.22 mmol) were dissolved in N,N-dimethylformamide (8 mL). 1-[3-(dimethylamino)propyl]-3-ethyl carbodiimide hydrochloride (0.43 g, 2.24 mmol) was then added followed by N,N-diisopropylethyl amine (0.55 mL, 3.09 mmol). The reaction mixture was stirred overnight, diluted with ethyl acetate and washed with water and saturated aqueous sodium bicarbonate. The organic phase was then dried over anhydrous sodium sulfate, filtered and concentrated in vacuo to give a brown oil. Purification by flash chromatography using a solvent gradient from 30% to 50% ethyl acetate in hexane provided the desired title compound, which was redissolved in dichloromethane and evaporated to dryness in vacuo to a white foam (1.1 g).

$^{1}$H NMR (DMSO-$d_6$, 400 MHz): δ 1.41 (s, 9H), 1.83 (s, 3H), 3.38 (br, 4H), 3.59–3.61 (m, 4H), 5.15 (br, 2H), 5.41 (s, 2H), 6.07 (d, 1H), 6.28 (d, 1H), 6.85–6.90 (m, 2H), 6.99–7.06 (m, 2H), 7.12–7.16 (m, 1H), 7.21 (d, 1H), 7.25 (s, 1H), 7.40–7.42 (m, 1H), 7.58 (t, 1H), 7.67 (t, 1H), 7.79 (d, 1H).

MS [(+)APCI, m/z]: 659 $[M+H]^+$.

Anal. Calcd. for $C_{37}H_{37}F_3N_4O_4$+0.09 $CH_2Cl_2$+0.18 $C_4H_8O_2$: C 66.56, H 5.71, N 8.21.

Found: C 66.27, H 5.40, N 8.00.

Step B. 10,11-Dihydro-10-[[2-methyl-2'-trifluoromethyl-[1,1'-biphenyl]-4-yl]carbonyl]-3-(1-piperazinylcarbonyl)-5H-pyrrolo[2,1-c][1,4]benzodiazepine hydrochloride salt The 4-[[10,11-dihydro-10-[[2-methyl-2'-trifluoromethyl [1,1'-biphenyl]-4-yl]carbonyl]-5H-pyrrolo[2,1-c][1,4] benzodiazepin-3-yl]carbonyl]-1-piperazine carboxylic acid, tert-butyl ester of Step A (0.85 g, 1.29 mmol) was added in one portion to stirred ethyl acetate (10 mL) saturated with hydrogen chloride gas at 0° C. The reaction mixture was stirred for 90 minutes under nitrogen. A precipitate formed after several minutes. The reaction was then warmed to room temperature and diluted with diethyl ether. The precipitated product was collected by filtration and dried under high vacuum to provide 0.65 g of the title compound hydrochloride salt as an off-white foam.

$^{1}$H NMR (DMSO-$d_6$, 400 MHz): δ 1.84 (s, 3H), 3.16 (br, 4H), 3.83–3.85 (m, 4H), 5.15 (br, 2H), 5.43 (s, 2H), 6.09 (d, 1H), 6.38 (d, 1H), 6.87–6.91 (m, 2H), 6.99–7.01 (m, 1H), 7.06 (t, 1H), 7.13–7.17 (m, 1H), 7.21 (d, 1H), 7.26 (s, 1H), 7.44–7.46 (m, 1H), 7.59 (t, 1H), 7.68 (t, 1H), 7.79 (d, 1H), 9.28 (br, 2H).

MS [(+)APCI, m/z]: 559 $[M+H]^+$.

Anal. Calcd. for $C_{32}H_{29}F_3N_4O_2$+1.0 HCl+1.00$H_2O$+0.06 $C_4H_{10}O$: C 62.70, H 5.32, N 9.07. Found: C 62.42, H 5.22, N 8.94.

Step C. (2S)-3-{4-[(10-{[2-methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}propane-1,2-diol To a solution of 10,11-dihydro-10-[[2-methyl-2'-trifluoromethyl-[1,1'-biphenyl]-4-yl]carbonyl]-3-(1-piperazinylcarbonyl)-5H-pyrrolo[2,1-c][1,4]benzodiazepine hydrochloride salt of Step B (0.50 g, 0.84 mmol) and N,N-diisopropylethyl amine (0.16 mL, 0.92 mmol) in methanol (5 mL) was added (R )-(+)-glycidol (0.10 mL, 1.50 mmol). The reaction mixture was heated to 60° C. for 4 hours then cooled and concentrated in vacuo. The residue was partitioned between dichloromethane and water. The organic layer was dried over anhydrous sodium sulfate, filtered and concentrated in vacuo to give a white foam. Purification by flash chromatography on silica gel using a solvent system of 5% methanol in chloroform provided the title product, which was redissolved in dichloromethane and evaporated to dryness in vacuo to a white foam (0.38 g).

$^{1}$H NMR (DMSO-$d_6$, 400 MHz): δ 1.83 (s, 3H), 2.24–2.29 (m, 1H), 2.39–2.46 (m, 5H), 3.31–3.36 (m, 2H), 3.60–3.65 (m, 5H), 4.43 (d, 1H), 4.50 (br, 1H), 5.15 (br, 2H), 5.40 (s, 2H), 6.06 (d, 1H), 6.23 (d, 1H), 6.84–6.90 (m, 2H), 6.99–7.06 (m, 2H), 7.12–7.16 (m, 1H), 7.21 (d, 1H), 7.25 (s, 1H), 7.37–7.40 (m, 1H), 7.58 (t, 1H), 7.68 (t, 1H), 7.79 (d, 1H).

MS [(+)APCI, m/z]: 633 $[M+H]^+$.

Anal. Calcd. for $C_{35}H_{35}F_3N_4O_4$+0.50$H_2O$+0.15 $CH_2Cl_2$: C 64.51, H 5.59, N 8.56.

Found: C 64.20, H 5.21, N 8.41.

EXAMPLE 6

(2R)-3-{4-[(10-{[2-Methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}propane-1,2-diol To a solution of 10,11-dihydro-10-[[2-methyl-2'-trifluoromethyl-[1,1'-biphenyl]-4-yl]carbonyl]-3-(1-piperazinylcarbonyl)-5H-pyrrolo[2,1-c][1,4]benzodiazepine hydrochloride salt of Example 5, Step B (0.50 g, 0.84 mmol) and N,N-diisopropylethyl amine (0.16 mL, 0.92 mmol) in methanol (5 mL) was added (S)-(−)-glycidol (0.10 mL, 1.51 mmol). The reaction mixture was heated to 60° C. for 4 hours then cooled and concentrated in vacuo. The residue was partitioned between dichloromethane and water. The organic layer was dried over anhydrous sodium sulfate, filtered and concentrated in vacuo to give a white foam. Purification by flash chromatography on silica gel using a solvent system of 5% methanol in chloroform provided the title product, which was redissolved in dichloromethane and evaporated to dryness in vacuo to a white foam (0.36 g).

$^{1}$H NMR (DMSO-$d_6$, 400 MHz): δ 1.83 (s, 3H), 2.24–2.29 (m, 1H), 2.39–2.46 (m, 5H), 3.32–3.35 (m, 2H), 3.60–3.65 (m, 5H), 4.43 (d, 1H), 4.50 (br, 1H), 5.15 (br, 2H), 5.40 (s, 2H), 6.06 (d, 1H), 6.23 (d, 1H), 6.85–6.90 (m, 2H), 6.99–7.06 (m, 2H), 7.12–7.16 (m, 1H), 7.21 (d, 1H), 7.25 (s, 1H), 7.38–7.40 (m, 1H), 7.58 (t, 1H), 7.68 (t, 1H), 7.79 (d, 1H).

MS [(+)APCI, m/z]: 633 $[M+H]^+$.

Anal. Calcd. for $C_{35}H_{35}F_3N_4O_4$+0.20 $CHCl_3$+0.10 $CH_2Cl_2$: C 63.75, H 5.37, N 8.42.

Found: C 63.03, H 4.93, N 8.29.

EXAMPLE 7

Methyl 2-{4-[(10-{[2-methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}ethyl ether To a solution of 10-[(2-methyl-2'-trifluoromethyl-[1,1'-biphenyl]-4-yl)carbonyl]-10,11-dihydro-5H-pyrrolo[2,1-c][1,4]benzodiazepine-3-carboxylic acid of Example 1, Step F (0.50 g, 1.02 mmol) and 1-methoxyethylpiperazine (0.18 mL, 1.25 mmol) in N,N-dimethylformamide (4 mL) was added 1-hydroxybenzotriazole (0.15 g, 1.11 mmol) and 1-[3-(dimethylamino)propyl]-3-ethyl carbodiimide hydrochloride (0.22 g, 1.15 mmol) followed by N,N-diisopropylethyl amine (0.27 mL, 1.55 mmol). The reaction mixture was stirred overnight, diluted with ethyl acetate and washed with water and saturated aqueous sodium bicarbonate. The organic phase was then dried over anhydrous sodium sulfate, filtered and concentrated in vacuo to give a yellow oil. Purification by flash chromatography using a solvent system of 5% methanol in chloroform gave a white foam which was crystallized from diethyl ether to provide 0.32 g of title product as a white solid, m.p. 140–144° C.

$^1H$ NMR (DMSO-$d_6$, 400 MHz): δ 1.83 (s, 3H), 2.40–2.47 (m, 4H), 2.50 (t, 2H), 3.22 (s, 3H), 3.44 (t, 2H), 3.58–3.63 (m, 4H), 5.15 (br, 2H), 5.40 (s, 2H), 6.06 (d, 1H), 6.23 (d, 1H), 6.86–6.90 (m, 2H), 6.98–7.04 (m, 2H), 7.12–7.16 (m, 1H), 7.21 (d, 1H), 7.25 (s, 1H), 7.37–7.40 (m, 1H), 7.58 (t, 1H), 7.68 (t, 1H), 7.79 (d, 1H).

MS [(+)APCI, m/z]: 617 $[M+H]^+$.

Anal. Calcd. for $C_{35}H_{35}F_3N_4O_3$: C 68.17, H 5.72, N 9.09. Found: C 68.09, H 5.73, N 8.93.

EXAMPLE 8

(2R)-1-Methoxy-3-{4-[(10-{[2-methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}propan-2-ol To a solution of 10,11-dihydro-10-[[2-methyl-2'-trifluoromethyl-[1,1'-biphenyl]-4-yl]carbonyl]-3-(1-piperazinylcarbonyl)-5H-pyrrolo[2,1-c][1,4]benzodiazepine hydrochloride salt of Example 5, Step B (0.50 g, 0.84 mmol) and N,N-diisopropylethyl amine (0.16 mL, 0.92 mmol) in methanol (5 mL) was added (R)-(−)-glycidyl methyl ether (0.11 mL, 1.22 mmol). The reaction mixture was heated to 60° C. overnight then cooled and concentrated in vacuo. The residue was partitioned between dichloromethane and water. The organic layer was dried over anhydrous sodium sulfate, filtered and concentrated in vacuo to give a white foam. Purification by flash chromatography on silica gel using a solvent system of 3% methanol in chloroform provided 0.40 g of title product as a white foam.

$^1H$ NMR (DMSO-$d_6$, 400 MHz): δ 1.83 (s, 3H), 2.25–2.38 (m, 2H), 2.45 (br, 4H), 3.21–3.25 (m, 4H), 3.27–3.29 (m, 1H), 3.61 (br, 4H), 3.73–3.77 (m, 1H), 4.57 (d, 1H), 5.15 (br, 2H), 5.40 (s, 2H), 6.05 (d, 1H), 6.22 (d, 1H), 6.84–6.90 (m, 2H), 6.99–7.06 (m, 2H), 7.12–7.16 (m, 1H), 7.21 (d, 1H), 7.25 (s, 1H), 7.37–7.39 (m, 1H), 7.58 (t, 1H), 7.68 (t, 1H), 7.79 (d, 1H).

MS [(+)APCI, m/z]: 647 $[M+H]^+$.

Anal. Calcd. for $C_{36}H_{37}F_3N_4O_4+0.50H_2O$: C 65.94, H 5.84, N 8.54. Found: C 65.69, H 5.50, N 8.34.

EXAMPLE 9

[3-({4-[(2S)-2-Hydroxy-3-methoxypropyl]-1-piperazinyl}carbonyl)-5H-pyrrolo[2,1-c][1,4]benzodiazepin-10(11H)-yl][2-methyl-2'-trifluoromethyl-[1,1'-biphenyl]-4-yl]methanone To a solution of 10,11-dihydro-10-[(2-methyl-2-trifluoromethyl-[1,1'-biphenyl]-4-yl)carbonyl]-3-(1-piperazinylcarbonyl)-5H-pyrrolo[2,1-c][1,4]benzodiazepine hydrochloride salt of Example 5, Step B (0.50 g, 0.84 mmol) and N,N-diisopropylethyl amine (0.16 mL, 0.92 mmol) in methanol (5 mL) was added (S)-(+)-glycidyl methyl ether (0.11 mL, 1.22 mmol). The reaction mixture was heated to 60° C. overnight then cooled and concentrated in vacuo. The residue was partitioned between dichloromethane and water. The organic layer was dried over anhydrous sodium sulfate, filtered and concentrated in vacuo to give a white foam. Purification by flash chromatography using a solvent system of 3% methanol in chloroform provided 0.40 g of title product as a white foam.

$^1H$ NMR (DMSO-$d_6$, 400 MHz): δ 1.83 (s, 3H), 2.28–2.35 (m, 2H), 2.45 (br, 4H), 3.21–3.25 (m, 4H), 3.28–3.30 (m, 1H), 3.61 (br, 4H), 3.74–3.76 (m, 1H), 4.59 (d, 1H), 5.15 (br, 2H), 5.40 (s, 2H), 6.06 (d, 1H), 6.23 (d, 1H), 6.84–6.90 (m, 2H), 6.98–7.06 (m, 2H), 7.12–7.16 (m, 1H), 7.21 (d, 1H), 7.25 (s, 1H), 7.37–7.39 (m, 1H), 7.58 (t, 1H), 7.68 (t, 1H), 7.79 (d, 1H).

MS [(+)APCI, m/z]: 647 $[M+H]^+$.

Anal. Calcd. for $C_{36}H_{37}F_3N_4O_4+1.00H_2O+0.14\ CHCl_3$: C 63.70, H 5.78, N 8.22.

Found: 63.66, H 5.38, N 8.10.

EXAMPLE 10

N-(2,3-Dimethoxypropyl)-N-methyl-10-{[2-methyl-2'-trifluoromethyl-[1,1'-biphenyl]-4-yl]carbonyl}-10,11-dihydro-5H-pyrrolo[2,1-c][1,4]benzodiazepine-3-carboxamide To a solution of 10-[(2-methyl-2'-trifluoromethyl-[1,1'-biphenyl]-4-yl)carbonyl]-10,11-dihydro-5H-pyrrolo[2,1-c][1,4]benzodiazepine-3-carboxylic acid (2,3-dihydroxypropyl)-methyl-amide of Example 2 (0.50 g, 0.87 mmol) in tetrahydrofuran (10 mL) was added sodium hydride (60% suspension in oil, 0.14 g, 3.5 mmol). After the gas evolution ceased, iodomethane (0.43 mL, 6.9 mmol) was added and the reaction mixture stirred overnight. Additional amounts of sodium hydride (60% suspension in oil, 0.14 g, 3.5 mmol) and iodomethane (0.43 mL, 6.9 mmol) were added. After 1 hour, the reaction was quenched with water and extracted with dichloromethane. The combined organic layers were dried over anhydrous sodium sulfate, filtered and concentrated in vacuo to give a yellow oil. Purification by flash chromatography using a solvent system of 75% ethyl acetate in hexane provided 0.46 g of title product as an off-white foam.

$^1H$ NMR (DMSO-$d_6$, 400 MHz): δ 1.83 (s, 3H), 3.08 (s, 3H), 3.24 (s, 3H), 3.31 (br, 2H), 3.33 (br, 3H), 3.51–3.66 (br, 3H), 5.15 (br, 2H), 5.36–5.44 (m, 2H), 6.04 (d, 1H), 6.31 (d, 1H), 6.86–6.91 (m, 2H), 6.99–7.07 (m, 2H), 7.13–7.17 (m, 1H), 7.21 (d, 1H), 7.25 (s, 1H), 7.35–7.37 (m, 1H), 7.58 (t, 1H), 7.68 (t, 1H), 7.79 (d, 1H).

MS [ESI, m/z]: 606 $[M+H]^+$.

Anal. Calcd. for $C_{34}H_{34}F_3N_3O_4+0.20H_2O+0.10\ C_4H_8O_2$: C 66.85, H 5.74, N 6.80.

Found: C 66.59, H 5.52, N 6.74.

EXAMPLE 11

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid methyl-[(2-oxo-[1,3]dioxolan-4-yl)methyl]-amide To a solution of 10-[(2-methyl-2'-trifluoromethyl-[1,1'-biphenyl]-4-yl)carbonyl]-10,11-dihydro-5H-pyrrolo[2,1-c][1,4]benzodiazepine-3-carboxylic acid (2,3-dihydroxypropyl)-methyl-amide of Example 2 (0.50 g, 0.87 mmol) in dichloromethane (17 mL) at 0° C. was added N,N-diisopropylethyl amine (0.30 mL, 1.72 mmol) followed by 1,1'-carbonyldiimidazole (0.14 g, 0.87 mmol). The reaction was allowed to warm to room temperature while stirring overnight then concentrated in vacuo to give a white solid. The residue was partitioned between dichloromethane and water. The organic layer was dried over anhydrous sodium sulfate, filtered and concentrated in vacuo to give a white foam. Purification by flash chromatography using a solvent system of 80% ethyl acetate in hexane provided the title product, which was redissolved in dichloromethane and evaporated to dryness in vacuo to a white foam (0.48 g).

$^1H$ NMR (DMSO-$d_6$, 400 MHz): 61.83 (s, 3H), 3.08 (s, 3H), 3.27–3.30 (m, 1H), 3.74–3.79 (m, 1H), 3.91–3.96 (m, 1H), 4.26–4.30 (m, 1H), 4.62 (t, 1H), 5.08–5.15 (m, 2H), 5.37–5.45 (m, 2H), 6.07 (d, 1H), 6.35 (d, 1H), 6.86–6.91 (m, 2H), 7.00–7.07 (m, 2H), 7.14 (t, 1H), 7.21 (d, 1H), 7.25 (s, 1H), 7.38–7.40 (m, 1H), 7.58 (t, 1H), 7.68 (t, 1H), 7.79 (d, 1H).

MS [(+)ESI, m/z]: 604 $[M+H]^+$.

Anal. Calcd. for $C_{33}H_{28}F_3N_3O_5$+0.08 $CH_2Cl_2$+0.07 $C_4H_8O_2$: C 64.99, H 4.70, N 6.82.

Found: C 64.38, H 4.62, N 6.71.

EXAMPLE 12

N-[((4S,5S)-5-{(R)-Hydroxy[(4R)-2-oxo-1,3-dioxolan-4-yl]methyl}-2-oxo-1,3-dioxolan-4-yl)methyl]-N-methyl-10-{[2-methyl-2'-(trifluoromethyl)[1,1'-biphenyl]-4-yl]carbonyl}-10,11-dihydro-5H-pyrrolo[2,1-c]benzodiazepine-3-carboxamide To a solution of 10-[(2-methyl-2'-trifluoromethyl-[1,1'-biphenyl]-4-yl)carbonyl]-10,11-dihydro-5H-pyrrolo[2,1-c][1,4]benzodiazepine-3-carboxylic acid methyl-((2S,3R,4R,5R)-2,3,4,5,6-pentahydroxy-hexyl)-amide of Example 4 (0.35 g, 0.52 mmol) in dichloromethane (10 mL) at 0° C. was added N,N-diisopropylethyl amine (0.37 mL, 2.12 mmol) followed by 1,1'-carbonyldiimidazole (0.17 g, 1.05 mmol). The reaction mixture was allowed to warm to room temperature while stirring and after 4 hours was concentrated in vacuo to give a white solid. The residue was partitioned between dichloromethane and water. The organic layer was dried over anhydrous sodium sulfate, filtered and concentrated in vacuo to give a white foam. Purification by flash chromatography on silica gel using a solvent system of 75% ethyl acetate in hexane provided title product, which was redissolved in dichloromethane and evaporated to dryness in vacuo to yield a white foam (0.26 g).

$^1$H NMR (DMSO-$d_6$, 400 MHz): δ 1.83 (s, 3H), 3.16 (s, 3H), 3.79–3.84 (m, 1H), 3.98–4.05 (m, 2H), 4.39–4.43 (m, 1H), 4.57 (t, 1H), 4.75 (br, 1H), 4.85–4.90 (m, 1H), 4.92–4.96 (m, 1H), 5.15 (br, 2H), 5.42 (q, 2H), 6.08 (d, 1H), 6.35 (d, 1H), 6.39 (d, 1H), 6.86–6.91 (m, 2H), 7.00–7.07 (m, 2H), 7.13–7.17 (m, 1H), 7.21 (d, 1H), 7.25 (s, 1H), 7.38–7.40 (m, 1H), 7.58 (t, 1H), 7.68 (t, 1H), 7.79 (d, 1H).

MS [(+)ESI, m/z]: 720 $[M+H]^+$.

Anal. Calcd. for $C_{37}H_{32}F_3N_3O_9$+0.28 $C_4H_8O_2$+0.08 $CH_2Cl_2$: C 61.08, H 4.62, N 5.59.

Found: C 60.63, H 4.56, N 5.40.

EXAMPLE 13

2-(Acetyloxy)-1-({methyl[(10-{[2-methyl-2'-trifluoromethyl-[1,1'-biphenyl]-4-yl]carbonyl}-10,11-dihydro-5H-pyrrolo[2,1-c][1,4]benzodiazepin-3-yl)carbonyl]amino}methyl)ethyl acetate To a solution of 10-[(2-methyl-2'-trifluoromethyl-[1,1'-biphenyl]-4-yl)carbonyl]-10,11-dihydro-5H-pyrrolo[2,1-c][1,4]benzodiazepine-3-carboxylic acid (2,3-dihydroxypropyl)-methyl-amide of Example 2 (0.53 g, 0.90 mmol) in dichloromethane (2 mL) was added triethylamine (0.40 mL, 2.87 mmol) and a catalytic amount of 4-(dimethylamino) pyridine (10 mg, 0.082 mmol). After addition of acetic anhydride (0.37 mL, 3.92 mmol), the reaction mixture was stirred for 1 hour and then concentrated in vacuo. The residue was partitioned between water and diethyl ether. The organic layer was washed with 5% aqueous sodium bicarbonate, dried over anhydrous sodium sulfate, filtered and concentrated in vacuo to provide 0.52 g of title product as a white foam.

$^1$H NMR (DMSO-$d_6$, 400 MHz): δ 1.83 (s, 3H), 1.99 (s, 3H), 2.03 (s, 3H), 3.09 (br, 3H), 3.65–3.75 (br m, 2H), 4.08–4.12 (m, 1H), 4.22–4.26 (m, 1H), 5.15 (br, 2H), 5.36–5.41 (m, 3H), 6.06 (d, 1H), 6.31 (d, 1H), 6.86–6.91 (m, 2H), 6.99–7.07 (m, 2H), 7.13–7.17 (m, 1H), 7.21 (d, 1H), 7.25 (s, 1H), 7.39–7.41 (m, 1H), 7.58 (t, 1H), 7.68 (t, 1H), 7.79 (d, 1H).

MS [(+)APCI, m/z]: 662 $[M+H]^+$.

Anal. Calcd. for $C_{36}H_{34}F_3N_3O_6$: C 65.35, H 5.18, N 6.35. Found: C 64.81, H 5.05, N 6.26.

EXAMPLE 14

10-[(2'-Methoxy-2-methyl-[1,1'-biphenyl]-4-yl)carbonyl]-10,11-dihydro-5H-pyrrolo[2,1-c][1,4]benzodiazepine-3-carboxylic acid (2,3-dihydroxy-propyl)-methyl-amide Step A. 2-Methyl-2'-methoxy-[1,1'-biphenyl]-4-carboxylic acid methyl ester A mixture of 3-methyl-4-bromobenzoic acid methyl ester (2.0 g, 8.7 mmol), 2-methoxyphenyl boronic acid (1.32 g, 8.7 mmol) and sodium carbonate (4.1 g, 38.7 mmol) in toluene:ethanol:water (50 mL:25 mL: 25 mL), was purged with nitrogen for 1 hour. After addition of the tetrakis (triphenylphosphine) palladium(0) catalyst (0.50 g, 0.43 mmol), the reaction mixture was heated at 100° C. overnight. After cooling, the reaction was filtered through Celite and the cake washed with ethyl acetate. The organic layer was washed with water, dried over anhydrous sodium sulfate, filtered and concentrated in vacuo to give a brown oil. Purification by flash chromatography with a solvent gradient from 20% to 50% dichloromethane in hexane gave 2.0 g of product as a colorless oil.

$^1$H NMR (DMSO-$d_6$, 400 MHz): δ 2.09 (s, 3H), 3.70 (s, 3H), 3.85 (s, 3H), 7.00–7.04 (m, 1H), 7.08–7.11 (m, 2H), 7.23 (d, 1H), 7.37–7.41 (m, 1H), 7.77–7.79 (m, 1H), 7.83–7.84 (m, 1H).

MS [(+)APCI, m/z]: 257 $[M+H]^+$.

Anal. Calcd. for $C_{16}H_{16}O_3$: C 74.98, H 6.29. Found: C 74.06, H 6.17.

Step B. 2-Methyl-2'-methoxy-[1,1'-biphenyl]-4-carboxylic acid

The 2-methyl-2'-methoxy-[1,1'-biphenyl]-4-carboxylic acid methyl ester of Step A (1.9 g, 7.4 mmol) was dissolved in tetrahydrofuran (30 mL) and 1 N sodium hydroxide (15 mL, 15 mmol) was added. The reaction mixture was heated at reflux overnight, then cooled and acidified with 2 N hydrochloric acid. The aqueous layer was extracted with ethyl acetate. The combined organic layers were dried over anhydrous sodium sulfate, filtered and concentrated in vacuo to give 1.6 g of product as a white solid, m.p. 160–162° C.

$^1$H NMR (DMSO-$d_6$, 400 MHz): δ 2.09 (s, 3H), 3.70 (s, 3H), 7.00–7.03 (m, 1H), 7.08–7.10 (m, 2H), 7.20 (d, 1H), 7.36–7.40 (m, 1H), 7.75–7.78 (m, 1H), 7.82 (s, 1H), 12.85 (br, 1H).

MS [(−) APCI, m/z]: 241 $[M-H]^-$.

Anal. Calcd. for $C_{15}H_{14}O_3$: C 74.36, H 5.82. Found: C 73.93, H 5.71.

Step C. (10,11-Dihydro-5H-pyrrolo[2,1-c][1,4]benzodiazepin-10-yl)-(2'-methoxy-2-methyl-[1,1'-biphenyl]-4-yl)-methanone The 2-methyl-2'-methoxy-[1,1'-biphenyl]-4-carboxylic acid of Step B (0.50 g, 2.06 mmol) was suspended in thionyl chloride (3 mL) and the mixture heated at reflux for 30 minutes. After cooling, the thionyl chloride was removed in vacuo. The residue was dissolved in toluene and concentrated in vacuo to give the crude acid chloride as a brown oil. The acid chloride was then dissolved in dichloromethane (5 mL) and slowly added to a solution of 10,11-dihydro-5H-pyrrolo[2,1-c][1,4]benzodiazepine (0.57 g, 3.10 mmol) and N,N-diisopropylethyl amine (0.79 mL, 4.53 mmol) in dichloromethane (15 mL). After stirring for 1 hour, the reaction was quenched with water. The organic layer was washed with 1 N hydrochloric acid, 1 N sodium hydroxide and brine, dried over anhydrous sodium sulfate, filtered and concentrated in vacuo to give a yellow foam. Purification by flash chromatography on silica gel using a solvent gradient of 15 to 25% ethyl acetate in hexane yielded a white foam which crystallized upon sonication with ethanol/hexane to give 0.42 g of the desired title product as a white solid, m.p. 133–135° C.

$^1$H NMR (DMSO-$d_6$, 400 MHz): δ 1.93 (s, 3H), 3.65 (s, 3H), 4.80–5.40 (br, 4H), 5.92–5.96 (m, 2H), 6.81–6.82 (m, 1H), 6.89–6.91 (m, 1H), 6.95–7.05 (m, 5H), 7.16–7.25 (m, 3H), 7.31–7.35 (m, 1H), 7.47–7.49 (m, 1H).

MS [(+)ESI, m/z]: 409 $[M+H]^+$.

Anal. Calcd. for $C_{27}H_{24}N_2O_2$: C 79.39, H 5.92, N 6.86. Found: C 79.16, H 5.87, N 6.90.

Step D. 2,2,2-Trichloro-1-{10-[(2'-methoxy-2-methyl-[1,1'-biphenyl]-4-yl)carbonyl]-10,11-dihydro-5H-pyrrolo[2,1-c][1,4]benzodiazepin-3-yl}ethanone To a solution of (10,11-dihydro-5H-pyrrolo[2,1-c][1,4]benzodiazepin-10-yl)-(2'-methoxy-2-methyl-[1,1'-biphenyl]-4-yl)-methanone of Step C (1.5 g, 3.67 mmol) in dichloromethane (20 mL) was added N,N-diisopropylethyl amine (1.28 mL, 7.35 mmol) followed by slow addition of trichloroacetyl chloride (1.23 mL, 11.0 mmol). The reaction mixture was stirred overnight at room temperature then quenched with water. The organic phase was washed with 0.1 N hydrochloric acid followed by water, then dried over anhydrous sodium sulfate, filtered and concentrated in vacuo to give a green oil. Purification by flash chromatography on silica gel using a solvent system of 20% ethyl acetate in hexane provided the title compound, which was redissolved in dichloromethane and evaporated to dryness in vacuo to a yellow foam (2.1 g).

$^1$H NMR (DMSO-$d_6$, 400 MHz): δ 1.94 (s, 3H), 3.65 (s, 3H), 5.25 (br, 2H), 5.97 (br, 2H), 6.36–6.37 (m, 1H), 6.90–6.92 (m, 1H), 6.96–7.06 (m, 5H), 7.15–7.23 (m, 2H), 7.26 (s, 1H), 7.32–7.36 (m, 1H), 7.44–7.47 (m, 2H).

MS [(+)APCI, m/z]: 553 $[M+H]^+$.

Anal. Calcd. for $C_{29}H_{23}C_{13}N_2O_3$+0.13 $C_4H_8O_2$+0.13 $CH_2Cl_2$:C 61.79, H 4.25, N 4.86.

Found: C 60.43, H 4.50, N 4.80.

Step E. 10-[(2'-Methoxy-2-methyl-[1,1'-biphenyl]-4-yl)carbonyl]-10,11-dihydro-5H-pyrrolo[2,1-c][1,4]benzodiazepine-3-carboxylic acid To a solution of 2,2,2-trichloro-1-{10-[(2'-methoxy-2-methyl-[1,1'-biphenyl]-4-yl)carbonyl]-10,11-dihydro-5H-pyrrolo[2,1-c][1,4]benzodiazepin-3-yl} ethanone of Step D (2.0 g, 3.6 mmol) in acetone (20 mL) was added 2.5 N sodium hydroxide (2.9 mL, 7.25 mmol). After stirring overnight, the reaction mixture was acidified with 2 N hydrochloric acid (4.0 mL, 8.0 mmol) then concentrated in vacuo. The residue was partitioned between ethyl acetate and water. The organic layer was dried over anhydrous sodium sulfate, filtered and concentrated in vacuo to give a brown solid. Trituration with diethyl ether-hexane provided 1.4 g of the desired product as a white solid, m.p. 174–184° C.

$^1$H NMR (DMSO-$d_6$, 400 MHz): δ 1.93 (s, 3H), 3.65 (s, 3H), 5.17 (br, 2H), 5.94 (br, 2H), 6.09–6.10 (m, 1H), 6.77 (d, 1H), 6.89–7.06 (m, 6H), 7.10–7.19 (m, 2H), 7.23 (s, 1H), 7.31–7.38 (m, 2H), 12.31 (br, 1H).

MS [(−)APCI, m/z]: 451 $[M-H]^-$.

Anal. Calcd. for $C_{28}H_{24}N_2O_4$+0.10 $C_4H_{10}O$: C 74.17, H 5.48, N 6.09. Found: C 73.63, H 5.68, N 5.94.

Step F. 10-[(2'-Methoxy-2-methyl-[1,1'-biphenyl]-4-yl)carbonyl]-10,11-dihydro-5H-pyrrolo[2,1-c][1,4]benzodiazepine-3-carboxylic acid (2,3-dihydroxy-propyl)-methyl-amide To a solution of 10-[(2'-methoxy-2-methyl-[1,1'-biphenyl]-4-yl)carbonyl]-10,11-dihydro-5H— pyrrolo[2,1-c][1,4]benzodiazepine-3-carboxylic acid of Step E (0.50 g, 1.10 mmol) and 3-methylamino-1,2-propanediol (0.14 mL, 1.33 mmol) in N,N-dimethylformamide (4 mL) was added 1-hydroxybenzotriazole monohydrate (0.16 g, 1.18 mmol) and 1-[3-(dimethylamino)propyl]-3-ethylcarbodiimide hydrochloride (0.23 g, 1.20 mmol) followed by N,N-diisopropylethyl amine (0.29 mL, 1.66 mmol). The reaction mixture was stirred overnight, diluted with ethyl acetate and washed with water and saturated aqueous sodium bicarbonate. The organic phase was then dried over anhydrous sodium sulfate, filtered and concentrated in vacuo to give a yellow oil. Purification by flash chromatography using a solvent system of 3% methanol in chloroform gave a white foam which was crystallized by trituration with diethyl ether-hexane to provide 0.11 g of title product as a white amorphous solid.

$^1$H NMR (DMSO-$d_6$, 400 MHz): δ 1.93 (s, 3H), 3.08 (br, 3H), 3.34 (br, 1H), 3.51 (br, 2H), 3.65 (s, 3H), 3.78 (br, 1H), 4.62 (t, 1H), 4.91 (br, 1H), 5.15 (br, 2H), 5.35–5.42 (br m, 2H), 6.02–6.03 (m, 1H), 6.33 (d, 1H), 6.89 (d, 1H), 6.94–7.00 (m, 4H), 7.04 (d, 1H), 7.11–7.20 (m, 3H), 7.23 (s, 1H), 7.31–7.35 (m, 1H), 7.40–7.42 (m, 1H).

MS [(+)APCI, m/z]: 540 $[M+H]^+$.

Anal. Calcd. for $C_{32}H_{33}N_3O_5$+0.40$H_2O$+0.09 $C_4H_{10}O$: C 70.22, H 6.32, N 7.59.

Found: C 70.04, H 6.26, N 7.41.

EXAMPLE 15

N-[(2S)-2,3-Dihydroxypropyl]-10-[(2'-methoxy-2-methyl-[1,1'-biphenyl]-4-yl)carbonyl]-N-methyl-10,11-dihydro-5H-pyrrolo[2,1-c][1,4]benzodiazepine-3-carboxamide The title compound was obtained from the 10-[(2'-methoxy-2-methyl-[1,1'-biphenyl]-4-yl)carbonyl]-10,11-dihydro-5H-pyrrolo[2,1-c][1,4]benzodiazepine-3-carboxylic acid (2,3-dihydroxy-propyl)-methyl-amide of Example 14 by chiral separation on a preparative Chiralpak OD HPLC column (4.6×250 mm) using a solvent system of 50% hexane in ethanol. The homogeneous material was redissolved in dichloromethane and evaporated to dryness in vacuo to yield a white foam (0.035 g, stereochemistry arbitrarily assigned).

$^1$H NMR (DMSO-$d_6$, 400 MHz): δ 1.93 (s, 3H), 3.08 (br, 3H), 3.34 (br, 1H), 3.51 (br, 2H), 3.65 (s, 3H), 3.78 (br, 1H), 4.60 (t, 1H), 4.89–4.90 (m, 1H), 5.15 (br, 2H), 5.35–5.42 (br m, 2H), 6.01–6.02 (m, 1H), 6.33 (d, 1H), 6.89 (d, 1H), 6.94–7.01 (m, 4H), 7.04 (d, 1H), 7.11–7.20 (m, 3H), 7.23 (s, 1H), 7.31–7.35 (m, 1H), 7.40–7.42 (m, 1H).

MS [ESI, m/z]: 540 $[M+H]^+$.

Anal. Calcd. for $C_{32}H_{33}N_3O_5$+0.50$H_2O$+0.17 $CH_2Cl_2$: C 68.62, H 6.15, N 7.46.

Found: C 68.51, H 6.28, N 7.37.

EXAMPLE 16

N-[(2R)-2,3-Dihydroxypropyl]-10-[(2'-methoxy-2-methyl-[1,1'-biphenyl]-4-yl)carbonyl]-N-methyl-10,11-dihydro-5H-pyrrolo[2,1-c][1,4]benzodiazepine-3-carboxamide The title compound was obtained from the 10-[(2'-methoxy-2-methyl-[1,1'-biphenyl]-4-yl)carbonyl]-10,11-dihydro-5H-pyrrolo[2,1-c][1,4]benzodiazepine-3-carboxylic acid (2,3-dihydroxy-propyl)-methyl-amide of Example 14 by chiral separation on a preparative Chiralpak OD HPLC column (4.6×250 mm) using a solvent system of 50% hexane in ethanol. The homogeneous material was redissolved in dichloromethane and evaporated to dryness in vacuo to provide a white foam (0.020 g, stereochemistry arbitrarily assigned).

$^1$H NMR (DMSO-$d_6$, 400 MHz): δ 1.93 (s, 3H), 3.08 (br, 3H), 3.34 (br, 1H), 3.51 (br, 2H), 3.65 (s, 3H), 3.78 (br, 1H), 4.60 (br, 1H), 4.90 (br, 1H), 5.15 (br, 2H), 5.35–5.42 (br m, 2H), 6.02 (br, 1H), 6.33 (d, 1H), 6.90 (d, 1H), 6.94–7.00 (m, 4H), 7.05 (d, 1H), 7.11–7.20 (m, 3H), 7.23 (s, 1H), 7.31–7.35 (m, 1H), 7.40–7.42 (m, 1H).

MS [(+)APCI, m/z]: 540 $[M+H]^+$.

Anal. Calcd. for $C_{32}H_{33}N_3O_5$+0.18 $CH_2Cl_2$: C 69.65, H 6.06, N 7.57. Found: C 69.51, H 6.07, N 7.27.

EXAMPLE 17

10-[(2'-Methoxy-2-methyl-[1,1'-biphenyl]-4-yl)carbonyl]-10,11-dihydro-5H-pyrrolo[2,1-c][1,4]benzodiazepine-3-carboxylic acid methyl-[(2S,3R,4R, 5R)-2,3,4,5,6-pentahydroxy-hexyl)-amide To a solution of 10-[(2'-methoxy-2-methyl-[1,1'-biphenyl]-4-yl)carbonyl]-10,11-dihydro-5H-pyrrolo[2,1-c][1,4]benzodiazepine-3-carboxylic acid of Example 14, Step E (0.70 g, 1.55 mmol), N-methyl-D-glucamine (0.36 g, 1.84 mmol) and 1-hydroxybenzotriazole monohydrate (0.23 g, 1.72 mmol) in N,N-dimethylformamide (6 mL) wad added 1-[3-(dimethylamino)propyl]-3-ethyl carbodiimide hydrochloride (0.33 g, 1.72 mmol) followed by N,N-diisopropylethyl amine (0.41 mL, 2.30 mmol). The reaction mixture was stirred overnight, then was diluted with ethyl acetate and washed with water and saturated aqueous sodium bicarbonate. The organic phase was then dried over anhydrous sodium sulfate, filtered and concentrated in vacuo to give a yellow foam. Purification by flash chromatography on silica gel using a solvent system of 10% methanol in chloroform provided the title compound, which was redissolved in dichloromethane and evaporated to dryness in vacuo to a pale, yellow foam (0.63 g).

$^1$H NMR (DMSO-$d_6$, 400 MHz): 61.93 (s, 3H), 3.06 (br, 3H), 3.33–3.57 (m, 7H), 3.65 (s, 3H), 3.92 (br, 1H), 4.32–4.41 (m, 3H), 4.50–4.51 (m, 1H), 4.91 (d, 1H), 5.15 (br, 2H), 5.35–5.41 (m, 2H), 6.01 (br, 1H), 6.35 (br, 1H), 6.90 (d, 1H), 6.94–7.00 (m, 4H), 7.04 (d, 1H), 7.11–7.20 (m, 2H), 7.23 (s, 1H), 7.31–7.35 (m, 1H), 7.42–7.44 (m, 1H).

MS [(+)APCI, m/z]: 630 $[M+H]^+$.

Anal. Calcd. for $C_{35}H_{39}N_3O_8$+0.42$H_2O$+0.11 $CHCl_3$+0.22 $CH_2Cl_2$: C 63.42, H 6.08, N 6.28. Found: C 61.35, H 5.64, N 5.95.

EXAMPLE 18

N-(2,3-Dihydroxypropyl)-7,8-dimethoxy-N-methyl-10-{[2-methyl-2'-trifluoromethyl-[1,1'-biphenyl]-4-yl]carbonyl}-10,11-dihydro-5H-pyrrolo[2,1-c][1,4]benzodiazepine-3-carboxamide Step A. 1-[(4,5-Dimethoxy-2-nitrophenyl)methyl]-1H-pyrrole-2-carboxaldehyde To a suspension of sodium hydride (0.724 g, 60% suspension in oil) in N,N-dimethylformamide (50 mL) was added pyrrole 2-carboxaldehyde (1.7 g, 18.1 mmol) and the reaction mixture was stirred for 30 minutes. It was then cooled to 0° C. and 4,5-dimethoxy-2-nitrobenzyl bromide (5.0 g, 1 equiv) was added dropwise over 20 minutes. After the addition, the reaction mixture was stirred at room temperature for 3 hours. It was then diluted with ethyl acetate (450 mL), washed with water, dried over anhydrous magnesium sulfate, filtered and evaporated to dryness. The crude product was triturated with water, filtered and washed with water. This material was dried over anhydrous potassium carbonate in vacuo to provide the title compound as a yellow crystalline solid (4.97 g), m.p. 109–112° C., which was used as such in the next step.

Step B. 7,8-Dimethoxy-10,11-dihydro-5H-pyrrolo[2,1-c][1,4]benzodiazepine

A mixture of the 1-[(4,5-dimethoxy-2-nitrophenyl)methyl]-1H-pyrrole-2-carboxaldehyde of Step A (4.97 g), acetic acid (0.5 mL), magnesium sulfate (0.5 g) and 10% palladium on charcoal (0.5 g) in ethyl acetate (50 mL) was hydrogenated overnight at atmospheric pressure. The reaction was then filtered through Celite and the solvent removed in vacuo to give the crude title compound as an amber foam (3.2 g) which was used in the next step without further purification.

Step C. 7,8-Dimethoxy-(10,11-dihydro-5H-pyrrolo[2,1-c][1,4]benzodiazepin-10-yl)-(4-bromo-3-methyl-phenyl)-methanone To a solution of 7,8-dimethoxy-10,11-dihydro-5H-pyrrolo[2,1-c][1,4]benzodiazepine of Step B (3.20 g) in dichloromethane (20 mL) was added 3-methyl-4-bromo benzoyl chloride (3.4 g, 1.1 equiv) and triethylamine (2.0 g, 1.5 equiv) and the mixture was stirred at room temperature overnight. The solvent was then removed in vacuo and the residue chromatographed on silica gel eluting with a solvent gradient from 5 to 50% ethyl acetate in petroleum ether to provide the title compounds as a yellow crystalline solid (3.5 g), m.p. 165–168° C.

$^1$H NMR ($CDCl_3$, 200 MHz): δ 2.30 (s, 3H), 3.55 (br, 3H), 3.85 (s, 3H), 5.1 (br, 4H), 6.05 (br, 1H), 6.1 (t, 1H), 6.3 (br, 1H), 6.65 (t, 1H), 6.8 (s, 2H), 7.3 (s, 2H).

MS [(+)ESI, m/z]: 442 $[M+H]^+$.

Step D. 7,8-Dimethoxy-[10,11-dihydro-5H-pyrrolo[2,1-c][1,4]benzodiazepin-10-yl][2-methyl-2'-trifluoromethyl-[1,1'-biphenyl]-4-yl]methanone The 7,8-dimethoxy-(10,11-dihydro-5H-pyrrolo[2,1-c][1,4]benzodiazepin-10-yl)-(4-bromo-3-methyl-phenyl)-methanone of Step C (1.0 g) was reacted with 2-trifluoromethylphenyl boronic acid (0.645 g, 1.5 equiv.), potassium phosphate (0.964 g, 2.0 equiv.) and a catalytic amount (0.050 g) of tetrakis(triphenylphosphine) palladium (0) in refluxing dioxane (10 mL) under nitrogen for 24 hours. The reaction was then cooled to room temperature and the solvent removed in vacuo. The residue was dissolved in dichloromethane and the solution was washed with water, dried over anhydrous magnesium sulfate, filtered and evaporated to dryness. The crude product so obtained was purified by chromatography on silica gel eluting with 5% ethyl acetate in dichloromethane to provide the title product as a white crystalline solid (1.0 g), m.p. 187–188° C.

$^1$H NMR (DMSO-$d_6$, 400 MHz): δ 1.85 (s, 3H), 3.40 (s, 3H), 3.70 (s, 3H), 5.20 (br, 4H), 5.92 (t, 1H), 5.96 (s, 1H), 6.56 (s, 1H), 6.77 (t, 1H), 6.90 (m, 1H), 7.05 (m, 2H), 7.20 (d, 1H), 7.30 (s, 1H), 7.58 (t, 1H), 7.68 (t, 1H), 7.80 (d, 1H).

MS [(+)APCI, m/z]: 507 $[M+H]^+$.

Anal. Calcd. for $C_{29}H_{25}F_3N_2O_3$: C 68.77, H 4.97, N 5.53. Found: C 68.85, H 5.05, N 5.43.

Step E. N-(2,3-Dihydroxypropyl)-7,8-dimethoxy-N-methyl-10-{[2-methyl-2'-trifluoromethyl-[1,1'-biphenyl]-4-yl]carbonyl}-10,11-dihydro-5H-pyrrolo[2,1-c][1,4]benzodiazepine-3-carboxamide A solution of 7,8-dimethoxy-[10,11-dihydro-5H-pyrrolo[2,1-c][1,4]benzodiazepin-10-yl][2-methyl-2'-trifluoromethyl-[1,1'-biphenyl]-4-yl]methanone of Step D (0.2 g, 0.39 mmol), diphosgene (1 equiv.) and triethylamine (1.5 equiv.) in dichloromethane (5 mL) was stirred at room temperature overnight. The solvent was removed in vacuo and the residue was dissolved in dichloromethane (5 mL). To the solution was added triethylamine (1.5 equiv.) and 3-methylamino-1,2-propanediol (1.5 equiv.) and the mixture was stirred at room temperature for 48 hours. The reaction mixture was then washed with water, dried over anhydrous magnesium sulfate, filtered and evaporated to dryness. The residue was first chromatographed on silica gel eluting with 2% methanol in dichloromethane and then chromatographed again with 2% methanol in ethyl acetate to provide the title compound (0.25 g) as a white solid, m.p. 184–186° C.

$^1$H NMR (DMSO-$d_6$, 400 MHz): δ 1.85 (s, 3H), 3.05 (s, 3H), 3.40 (s, 3H), 3.50 (br, 3H), 3.70 (s, 3H), 3.80 (br, 2H), 4.60 (t, 1H), 4.90 (s, 1H), 5.25 (dd, 4H), 6.00 (s, 1H), 6.30

(d, 1H), 6.50 (s, 1H), 6.90 (s, 2H), 7.05 (s, 1H), 7.20 (d, 1H), 7.30 (s, 1H), 7.60 (t, 1H), 7.70 (t, 1H), 7.80 (d, 1H).

MS [(+)APCI, m/z]: 638 $[M+H]^+$.

Anal. Calcd. for $C_{34}H_{34}F_3N_3O_6$ $+H_2O$: C 62.28, H 5.53, N 6.41. Found: C 62.43, H 5.64, N 6.39.

EXAMPLE 19

N,N-Bis(2-Hydroxyethyl)-7,8-dimethoxy-10-{[2-methyl-2'-trifluoromethyl-[1,1'-biphenyl]-4-yl]carbonyl}-10,11-dihydro-5H-pyrrolo[2,1-c][1,4]benzodiazepine-3-carboxamide A solution of N-(2,3-dihydroxypropyl)-7,8-dimethoxy-N-methyl-10-{[2-methyl-2'-trifluoromethyl-[1,1'-biphenyl]-4-yl]carbonyl}-10,11-dihydro-5H-pyrrolo[2,1-c][1,4]benzodiazepine-3-carboxamide of Example 18, Step D (0.31 mmol), diphosgene (1.1 equiv.) and triethylamine (1.5 equiv.) in dichloromethane (5 mL), was stirred at room temperature overnight. The solvent was removed in vacuo and the residue was dissolved in dichloromethane (5 mL). To the solution was added triethylamine (1.5 equiv.) and diethanolamine (1.5 equiv.) and the reaction was stirred overnight. The reaction mixture was then washed with water, dried over anhydrous magnesium sulfate, filtered and evaporated to dryness. The residue was first chromatographed on silica gel eluting with 2% methanol in dichloromethane and then rechromatographed with 2% methanol in ethyl acetate to provide the title compound (0.036 g) as a white solid, m.p. 130–132° C.

$^1H$ NMR (DMSO-$d_6$, 400 MHz): δ 1.85 (s, 3H), 3.40 (s, 3H), 3.60 (s, 8H), 3.70 (s, 3H), 4.80 (s, 2H), 5.00 (br, 2H), 5.20 (s, 2H), 6.00 (s, 1H), 6.25 (d, 1H), 6.45 (s, 1H), 6.90 (s, 1H), 6.95 (s, 1H), 7.05 (s, 1H), 7.20 (d, 1H), 7.30 (s, 1H), 7.60 (t, 1H), 7.70 (t, 1H), 7.80 (d, 1H).

MS [(+)APCI, m/z]: 638 $[M+H]^+$.

Anal. Calcd. for $C_{34}H_{34}F_3N_3O_6$+$H_2O$: C 62.28, H 5.53, N 6.41. Found: C 62.87, H 5.40, N 6.47.

EXAMPLE 20

10-{[6-Chloro-3-methoxy-2'-trifluoromethyl-[1,1'-biphenyl]-4-yl]carbonyl}-N-methyl-N-[(2S,3R,4R,5R)-2,3,4,5,6-pentahydroxyhexyl]-10,11-dihydro-5H-pyrrolo[2,1-c][1,4]benzodiazepine-3-carboxamide Step A. 4-Iodo-5-chloro-2-methoxy benzoic acid A stirred solution of 4-amino-5-chloro-2-methoxy benzoic acid (12.25 g , 60.8 mmol) in water (136 mL ) and concentrated sulfuric acid (34 mL) was cooled to 0° C. in a flask fitted with an overhead stirrer. A solution of sodium nitrite (4.62 g , 66.9 mmol) in water (26 mL) was added dropwise while keeping the internal temperature around 0° C. Potassium iodide (11.11 g, 66.9 mmol) and iodine (4.24 g, 33.5 mmol) were dissolved in water (130 mL) and added dropwise to the stirred reaction mixture. After 2 hours the reaction was extracted with ethyl acetate. The organic extracts were then washed with 10% sodium thiosulfate and brine, then dried over magnesium sulfate, filtered and evaporated to dryness to yield 11.32 g of the title compound, m.p. 150°–151° C. This material was used without further purification.

$^1H$ NMR (DMSO-$d_6$, 400 MHz): δ 13.03 (br, 1H), 7.70 (s, 1H), 7.63 (s, 1H), 3.82 (s, 3H).

MS [(−)-APCI, m/z]: 311 $[M-H]^-$.

Anal. Calcd. for $C_8H_6ClIO_3$: C 30.75, H 1.94. Found: C 31.28, H 1.78.

Step B. 2-Chloro-2'-trifluoromethyl-5-methoxy-[1,1'-biphenyl]-4-carboxylic acid.

To a stirred solution of 4-iodo-5-chloro-2-methoxy benzoic acid of Step A (3.12 g, 10 mmol) in N,N-dimethylformamide (100 mL) was added 2-trifluoromethylphenyl boronic acid (5.70 g, 30 mmol) and potassium carbonate (12.73 g, 92 mmol). This mixture was purged with nitrogen and then treated with a catalytic amount of tetrakis (triphenylphosphine) palladium(0) (0.58 g, 0.5 mmol). The reaction was heated to reflux overnight, cooled, acidified with 2N hydrochloric acid and extracted with ethyl acetate. The organic layer was washed with brine, dried over anhydrous magnesium sulfate, filtered, and evaporated to provide a nearly quantitative amount of the title acid which was used in the next step without further purification.

Step C. 10-{[6-Chloro-3-methoxy-2'-trifluoromethyl-[1,1'-biphenyl]-4-yl]carbonyl}-10,11-dihydro-5H-pyrrolo[2,1-c][1,4]benzodiazepine A stirred solution of the 2-chloro-2'-trifluoromethyl-5-methoxy-[1,1'-biphenyl]-4-carboxylic acid of Step B (3.46 g, 10.46 mmol) in tetrahydrofuran (20 mL) containing a catalytic amount of N,N-dimethylformamide was treated dropwise with thionyl chloride (1.36 g, 11.51 mmol). The reaction mixture was stirred for 2 hours, and then added dropwise to a solution of 10,11-dihydro-5H-pyrrolo[2,1-c][1,4]benzodiazepine (1.92 g 10.46 mmol) in tetrahydrofuran (20 mL) containing triethylamine (2.32 g, 23 mmol). The reaction mixture was stirred for 2 hours, diluted with dichloromethane and washed with saturated aqueous sodium bicarbonate and brine. The organic layer was dried over anhydrous magnesium sulfate, filtered, and evaporated to dryness. Trituration of the residue with acetone gave 3.14 g of the title compound. Recrystallization from acetone/hexane provided white crystals, m.p. 208–210° C.;

$^1H$ NMR (DMSO-$d_6$, 400 MHz) δ 3.46 (s, 3H), 5.16–5.20 (br, d, 3H), 5.89 (t, 1H), 5.97 (s, 1H), 6.70 (s, 1H), 6.80 (t, 1H), 7.80–7.00 (m, 10H).

MS [(+) ESI, m/z]: 497 $[M+H]^+$.

Anal. Calcd. for $C_{27}H_{20}ClF_3N_2O_2$+$0.5H_2O$: C 64.10, H 4.18, N 5.54. Found: C 64.40, H 3.97, N 5.54.

Step D. 10-{[6-Chloro-3-methoxy-2'-trifluoromethyl-[1,1'-biphenyl]-4-yl]carbonyl}-10,11-dihydro-5H-pyrrolo[2,1-c][1,4]benzodiazepine-3-carboxylic acid A solution of the 10-{[6-chloro-3-methoxy-2'-trifluoromethyl-[1,1'-biphenyl]-4-yl]carbonyl}-10,11-dihydro-5H-pyrrolo[2,1-c][1,4]benzodiazepine of Step C (2.29 g, 4.6 mmol) in dichloromethane (30 mL) was treated with N,N-diisopropylethyl amine (0.62 g, 4.84 mmol) and stirred for 10 minutes. Trichloroacetyl chloride (0.92 g, 5.07 mmol) was then added dropwise. The reaction mixture was stirred overnight, diluted with dichloromethane, washed with 0.1N hydrochloric acid, saturated aqueous sodium bicarbonate, and brine. The organic phase was dried over anhydrous magnesium sulfate, filtered, and evaporated to yield the crude trichloroketone intermediate which without further purification, was dissolved in acetone and treated with an excess of 1N sodium hydroxide. The mixture was stirred overnight, and then diluted with isopropyl acetate and acidified with 1N hydrochloric acid. The organic layer was washed with brine, dried over anhydrous magnesium sulfate, filtered, and evaporated to dryness. The solid residue was triturated with methanol to provide the title compound (1.23 g ) as a white solid, m.p. 220–222° C. (dec).

$^1H$ NMR (DMSO-$d_6$, 400 MHz) δ 3.40 (s, 3H), 6.12 (d, 1H), 6.68 (s, 1H), 6.72 (d, 1H), 6.94 (s, 2H), 7.07 (t, 1H), 7.25 (d, 2H), 7.62 (t, 2H), 7.70 (t, 1H), 7.78 (d, 1H), 12.31 (br, 1H).

MS [(+)APCI, m/z]: 541 $[M+H]^+$.

Anal. Calcd. for $C_{28}H_{20}ClF_3N_2O_4$+$0.25H_2O$: C 61.66, H 3.79, N 5.14. Found: C 61.47, H 3.64, N 5.06.

Step E. 10-{[6-Chloro-3-methoxy-2'-trifluoromethyl-[1,1'-biphenyl]-4-yl]carbonyl}-N-methyl-N-[(2S,3R,4R,5R)-2,3, 4,5,6-pentahydroxyhexyl]-10,11-dihydro-5H-pyrrolo[2,1-c][1,4]benzodiazepine-3-carboxamide To a stirred solution of the 10-{[6-chloro-3-methoxy-2'-trifluoromethyl-[1,1'-biphenyl]-4-yl]carbonyl-10,11-dihydro-5H-pyrrolo[2,1-c][1,4]benzodiazepine-3-carboxylic acid of Step D (0.250 g, 0.46 mmol) in N.N-dimethylformamide (2 mL) was added N-methyl-D-glucamine (0.109 mg, 0.55 mmol), 1-hydroxybenzotriazole (0.069 g, 0.51 mmol), 1-[3-(dimethylamino)propyl]-3-ethylcarbodiimide hydrochloride (0.087 g, 0.51 mmol), and N,N-diisopropylethyl amine (0.090 g, 0.69 mmol). After stirring overnight, the reaction mixture was taken up in chloroform, washed with saturated aqueous sodium bicarbonate and brine, dried over magnesium sulfate, filtered and evaporated. Purification of the residue by flash chromatography eluting with 10% methanol in chloroform provided the title compound (0.132 g ) as an off-white solid, 96.08% pure by analytical HPLC [Primesphere C-18 column (2.0× 150 mm); mobile phase: 45/55 acetonitrile/water containing 0.1% phosphoric acid].

$^1$H NMR (DMSO-$d_6$, 400 MHz) δ 3.05 (br, 3H), 4.33–4.38 (br m, 3H), 4.50 (s, 1H), 4.90 (s, 1H), 5.30 (s, 2H), 6.04 (s, 1H), 6.33 (s, 1H), 6.68 (s, 1H), 6.94–7.80 (m, 10H).

MS [(+)ESI, m/z]: 718 $[M+H]^+$.

Anal. Calcd for $C_{35}H_{35}ClF_3N_3O_8$: C 58.54, H 4.91, N 5.85. Found: C 58.29, H 4.48, N 5.42.

EXAMPLE 21

N-(2,3-Dihydroxypropyl)-10-{[2-methoxy-2'-trifluoromethyl-[1,1'-biphenyl]-4-yl]carbonyl}-N-methyl-10,11-dihydro-5H-pyrrolo[2,1-c][1,4]benzodiazepine-3-carboxamide Step A. Trifluoromethanesulfonic acid 4-formyl-2-methoxy-phenyl ester To a solution of vanillin (6.08 g, 40.0 mmol) and triethylamine (6.70 mL, 48.0 mmol) in dichloromethane (300 mL) was added dropwise a solution of trifluoromethanesulfonic anhydride (12.4 g, 44.0 mmol) in dichloromethane (100 mL) at 0° C. After stirring for 2 hours, the solution was concentrated, and the residue washed with water and extracted twice with ethyl acetate. Upon drying and concentrating, the residual dark oil was subjected to flash chromatography on silica gel eluting with 20% ethyl acetate in hexane providing the title product (8.91 g) as a light yellow oil, which was used in the next step without further purification.

Step B. 2-Methoxy-2'-trifluoromethyl-[1,1'-biphenyl]-4-carboxaldehyde

A stirred solution of trifluoromethanesulfonic acid 4-formyl-2-methoxy-phenyl ester of Step A (6.9 g, 22.1 mmol), 2-trifluoromethyl phenyl boronic acid (5.4 g, 28.6 mmol) and potassium phosphate (13.2 g, 62.2 mmol) in N,N-dimethylformamide (120 mL) was degassed with nitrogen, whereupon a catalytic amount (0.285 g) of [1,4-bis-(diphenylphosphine)butane]palladium (II) dichloride was added. The solution was heated to 120° C. for 5 hours, poured into water and extracted with ethyl acetate. The combined extracts were washed with water, dried over anhydrous magnesium sulfate and filtered through a plug of silica gel. Removal of the solvent provided the crude title compound (4.54 g) as an oil, which was used as such in the next step.

$^1$H NMR (200 MHz, $CDCl_3$): δ 3.91 (s, 3H). (s, 1H), 7.31–7.56 (m, 6H), 8.14 (d, 1H), 10.03 (s, 1H).

Step C. 3-Methoxy-2'-trifluoromethyl-[1,1'-biphenyl]-4-carboxylic acid

The 3-methoxy2'-trifluoromethyl-[1,1'-biphenyl]-4-carboxaldehyde of Step B (0.95 g, 3.41 mmol) and sulfamic acid (0.43 g, 4.43 mmol) were dissolved in a mixture of tetrahydrofuran and water (1:1, v/v, 30 mL). Sodium chlorite (0.31 g, 4.43 mmol) was added under stirring, and the solution turned yellow. After 30 minutes, additional sodium chlorite and sulfamic acid were added, and the solution stirred an additional hour. The solution was then concentrated, and the residue partitioned between ethyl acetate and water. The ethyl acetate layer was dried and concentrated to yield an oil, which solidified upon trituration with hexane to provide the title compound (0.84 g) as a yellow solid, which was used as such in the next step.

Step D. (10,11-Dihydro-5H-pyrrolo[2,1-c][1,4]benzodiazepin-10-yl)-(2-methoxy-2'-trifluoromethyl-[1,1'-biphenyl]-4-yl)-methanone The 3-methoxy-2'-trifluoromethyl-[1,1'-biphenyl]-4-carboxylic acid of Step C (1.6 g, 5.40 mmol) was added to a flask containing toluene (30 mL), thionyl chloride (1.4 mL) and one drop of N,N-dimethylformamide. The solution was stirred at 70° C. for 1 hour and then concentrated in vacuo. The residue was diluted with dichloromethane (40 mL) and to this solution was added 10,11-dihydro-5H-pyrrolo[2,1-c][1,4]benzodiazepine (0.94 g, 5.16 mmol). After the solution became homogeneous, N,N-diisopropylethyl amine (1.07 mL, 6.19 mmol) was added in one portion at 0° C. After 30 minutes the solution was concentrated, and the residue partitioned between water and ethyl acetate. The ethyl acetate was dried and concentrated to give a crude oil, which was chromatographed on silica gel eluting with 30% ethyl acetate in hexane to yield 1.2 g of product. The solid was recrystallized from ethyl acetate/hexane to provide the desired title product (0.87 g) as colorless crystals, m.p. 146–148° C.

$^1$H NMR (400 MHz, DMSO-$d_6$) δ 3.45 (s, 3H), 5.31 (br, 4H), 5.91 (s, 1H), 5.95 (br, 1H), 6.83 (s, 1H), 6.92–7.01 (m, 4H), 7.11 (t, 1H), 7.19 (m, 2H), 7.46 (d, 1H), 7.53 (t, 1H), 7.62 (t, 1H), 7.72 (d, 1H ).

MS [(+)ESI, m/z]: 463 $[M+H]^+$.

Anal. Calcd. for $C_{27}H_{21}F_3N_2O_2$: C 70.12, H 4.58, N 6.06. Found: C 70.53, H 4.72, N 5.89.

Step E. 10-{[2-Methoxy-2'-trifluoromethyl-[1,1'-biphenyl]-4-yl]carbonyl}-10,11-dihydro-5H-pyrrolo[2,1-c][1,4]benzodiazepine-3-carboxylic acid To a stirred solution of the (10,11-dihydro-5H-pyrrolo[2,1-c][1,4]benzodiazepin-10-yl)-(2-methoxy-2'-trifluoromethyl-[1,1'-biphenyl]-4-yl)-methanone of Step D (2.34 g, 5.0 mmol) and N,N-diisopropylethyl amine (1.04 mL, 6.0 mmol) in dichloromethane (100 mL) was added dropwise a solution of trichloroacetyl chloride (1.09 g, 6.0 mmol) in dichloromethane (20 mL) kept at 0° C. After the addition was complete, the solution was stirred overnight at room temperature, then washed with 10% aqueous potassium carbonate. The organic phase was dried and concentrated to yield a dark residue. The residue was purified by filtration through a plug of silica gel, eluting with 20% ethyl acetate in hexane. The resulting tan colored product was dissolved in acetone and 1 N sodium hydroxide (2:1, v/v) and the mixture was stirred for 30 minutes. The solution was then concentrated and extracted with ethyl acetate. The combined organic phases were dried and concentrated to yield a yellow oil. The oil was triturated with hexane, and the resulting off-white solid was removed by filtration and dried in vacuo to yield the title compound (1.86 g).

Step F. N-(2,3-Dihydroxypropyl)-10-{[2-methoxy-2'-trifluoromethyl-[1,1'-biphenyl]-4-yl]carbonyl}-N-methyl-10,11-dihydro-5H-pyrrolo[2,1-c][1,4]benzodiazepine-3-carboxamide To a stirred solution of the 10-{[2-methoxy-2'-trifluoromethyl-[1,1'-biphenyl]-4-yl]carbonyl}-10,11- dihydro-5H-pyrrolo[2,1-c][1,4]benzodiazepine-3-carboxylic acid of Step E (0.300 g, 0.65 mmol)) in N,N-dimethylformamide (15 mL) was added 1-[3-(dimethylamino)propyl]-3-ethylcarbodiimide hydrochloride (0.150 g, 0.78 mmol) and 1-hydroxybenzotriazole (0.110 g, 0.78 mmol). After the solution became homogeneous 3-methylamino-1,2-propanediol (0.082 g, 0.78 mmol) was added, and the solution was stirred at room temperature overnight. The mixture was then poured into water and extracted with ethyl acetate. The combined ethyl acetate layers were washed with water, dried and concentrated to dryness. The residue was subjected to silica chromatography eluting with 10% methanol in chloroform. The pure fractions were concentrated and the residue azeotroped and triturated several times with hexane to provide the title product (0.118 g) as a white solid, m.p. 119–123° C.

$^1$H NMR (400 MHz, DMSO-$d_6$): δ 3.08 (br, 3H), 3.51–3.48 (m, 5H), 3.80 (br, 1H), 4.62 (t, 1H), 4.85 (br, 1H), 5.42 (br, 2H), 6.04 (s, 1H), 6.34 (s, 1H), 6.85–6.973 (m, 4H), 7.06 (t, 1H), 7.11 (t, 1H), 7.19 (d, 1H), 7.40 (d, 1H), 7.56 (t, 1H), (d, 1H), 7.62 (t, 1H), 7.74 (d, 1H).

MS [EI , m/z]: 593 $[M]^+$.

Anal. Calcd. for $C_{32}H_{30}F_3N_3O_5$: C 64.75, H 5.09, N 7.08. Found: C 63.51, H 4.63, N 6.98.

EXAMPLE 22

N-[(3-Dimethylamino)-2-hydroxy-propyl]-10-{[2-methoxy-2'-trifluoromethyl-[1,1'-biphenyl]-4-yl]carbonyl}-N-methyl-10,11-dihydro-5H-pyrrolo[2,1-c][1,4]benzodiazepine-3-carboxamide The title compound was obtained from 10-{[2-methoxy-2'-trifluoromethyl-[1,1'-biphenyl]-4-yl]carbonyl}-10,11-dihydro-5H-pyrrolo[2,1-c][1,4]benzodiazepine-3-carboxylic acid of Example 21, Step E (0.15 g, 0.32 mmol) and N,N,N'-trimethyl-2-hydroxy-propane diamine (0.065 g, 0.32 mmol.) in the manner of Example 21, Step F, as a white solid (0.093 g), m.p. 120–125 (dec.).

$^1$H NMR (400 MHz, DMSO-$d_6$): δ 7.74 (d, 1H), 7.62 (t, 1H), 7.56 (t, 1H), 7.40 (d, 1H), 7.19 (d, 1H), 7.11 (t, 1H), 7.06 (t, 1H), 6.85–6.97 (m, 4H), 6.34 (s, 1H), 6.04 (s, 1H), 5.40 (br, 2H), 5.10 (br, 1H), 4.84 (br, 1H), 3.91 (br, 1H), 3.59 (br, 1H), 3.41 (s, 3H), 3.15 (br, 3H), 2.19 (br, 6H).

MS [EI, m/z]: 620 $[M]^+$.

Anal. Calcd. for $C_{34}H_{35}F_3N_4O_4$: C 65.8, H 5.69, N 9.03. Found: C 65.39, H 6.02, N 8.56.

EXAMPLE 23

10-{[2-Methoxy-2'-trifluoromethyl-[1,1'-biphenyl]-4-yl]carbonyl}-N-methyl-N-[(2R,3S,4R,5S)-2,3,4,5,6-pentahydroxyhexyl]-10,11-dihydro-5H-pyrrolo[2,1-c][1,4]benzodiazepine-3-carboxamide The title compound was obtained from 10-{[2-methoxy-2'-trifluoromethyl-[1,1'-biphenyl]-4-yl]carbonyl}-10,11-dihydro-5H-pyrrolo[2,1-c][1,4]benzodiazepine-3-carboxylic acid of Example 21, Step E (0.15 g, 0.32 mmol) and 1-deoxy-1-(methylamino)-D-galactitol (0.063 g, 0.32 mmol) in the manner of Example 21, Step F, as a white solid (0.078 g), m.p. 132–140° C. (dec).

$^1$H NMR (400 MHz, DMSO-$d_6$): δ 3.06 (br, 3H), 3.25–3.51 (m, 5H), d, 1H), 3.71 (m, 1H), 4.06 (d, 1H), 4.15 (d, 1H), 4.23 (br, 1H), 4.42 (t, 1H), 5.42 (br, 2H), 6.06 (s, 1H), 6.38 (s, 1H), 6.85–6.973 (m, 4H), 7.04 (t, 1H), 7.11 (t, 1H), 7.19 (d, 1H), 7.42 (d, 1H), 7.56 (t, 1H), 7.62 (t, 1H ).

MS [EI, m/z]: 683 $[M]^+$.

Anal. Calcd. for $C_{35}H_{36}F_3N_3O_8$: C 61.49, H 5.31, N 6.15. Found: C 60.38, H 4.88, N 5.88.

EXAMPLE 24

10-[4-(Naphthalen-1-yl)benzoyl]-10,11-dihydro-5H-pyrrolo[2,1-c][1,4]benzodiazepine-3-carboxylic acid bis-(2-hydroxy-ethyl)-amide Step A. 4-Naphthalen-1-yl-benzoic acid methyl ester Methyl 4-bromobenzoate (0.96 g, 4.46 mmol) was added to a mixture of 1-naphthaleneboronic acid (0.73 g, 4.25 mmol) and sodium carbonate (0.075 g, 7.08 mmol) in toluene (30 mL), ethanol (6 mL) and water (12 mL). The resultant solution was purged with nitrogen for 10 minutes before tetrakis(triphenylphosphine) palladium(0) (0.10 g, 0.09 mmol) was added. The reaction mixture was heated to reflux for 65 hours. The solution was cooled to ambient temperature, then filtered through a pad of Celite, which was subsequently rinsed with ethyl acetate. The combined filtrate was diluted to 100 mL with water/ethyl acetate (1:1, v/v). The aqueous layer was extracted with ethyl acetate, and the combined extracts were dried over anhydrous magnesium sulfate, filtered, and evaporated to dryness to yield the title compound as a gold oil (1.09 g). This material was used without further purification in the next step.

$^1$H NMR (300 MHz, DMSO-$d_6$): δ 8.10 (d, 2H), 8.02 (t, 2H), 7.75 (d, 1H), 7.57 (m, 6H), 3.92 (s, 3H).

Step B. 4-Naphthalen-1-yl-benzoic acid

To a stirred solution of the 4-naphthalen-1-yl-benzoic acid methyl ester of Step A (1.09 g, 4.15 mmol), in methanol (18 mL) and water (6 mL), cooled to 5° C., was added lithium hydroxide monohydrate (0.42 g, 10.0 mmol). The solution was allowed to warm to ambient temperature as stirring was continued for 20 hours. The reaction mixture was poured into water, acidified to pH 4 with acetic acid, and the resultant precipitate was isolated by vacuum filtration to afford the title compound as an off-white solid (0.92 g), m.p. 221–224° C.

$^1$H NMR (400 MHz, DMSO-$d_6$): δ 6.40–7.60 (m, 7H),. 7.56 (d, 1H), 7.98 (d, 1H), 8.01 (d, 1H), 8.07 (d, 2H).

MS [EI, m/z]: 248 $[M]^+$.

Anal. Calc'd. for $C_{17}H_{12}O_2$: C 82.24, H 4.87. Found: C 81.90, H 4.63.

Step C. [4-(Naphtalen-1-yl)phenyl][10,11-dihydro-5H-pyrrolo[2,1-c][1,4]benzodiazepin-10-yl]methanone N,N-Dimethylformamide (2 drops) was added to a solution of the 4-naphthalen-1-yl-benzoic acid of Step B (0.60 g, 2.40 mmol) in anhydrous tetrahydrofuran (15 mL). Oxalyl chloride (0.34 g, 2.64 mmol) was added and the mixture was warmed to reflux. The resultant solution was cooled to ambient temperature before being evaporated to dryness to give the crude acid chloride as a gold solid, which was used without further purification. To a mixture of 10,11-dihydro-5H-pyrrolo[2,1-c][1,4]benzodiazepine (0.37 g, 2.00 mmol) and triethylamine (0.24 g, 2.40 mmol) in dichloromethane (5 mL), cooled in an ice bath, was added dropwise a solution of the crude acid chloride in dichloromethane (5 mL). The cooling bath was removed and after stirring for 48 hours, the reaction mixture was washed sequentially with water, saturated aqueous sodium bicarbonate, saturated aqueous sodium chloride and 1 N sodium hydroxide. The dichloromethane solution was dried with anhydrous magnesium sulfate, filtered, then evaporated to dryness to yield a brown foam. Purification by flash chromatography on silica gel eluting with hexane-ethyl acetate (4:1) resulted in a white foam (0.47 g). Treatment of the white foam with diethyl ether and sonication resulted in a white solid (0.37 g), m.p. 169.5–171° C.

$^1$H NMR (400 MHz, DMSO-$d_6$): δ 5.32 (br, 4H), 5.93 (m, 1H), 5.97 (s, 1H), 6.83 (m, 1H), 7.01 (d, 1H), 7.18 (m, 2H), 7.32 (t, 2H), 7.41, (d, 1H), 6.45–7.60 (m, 5H), 7.93 (d, 1H), 7.97 (d, 1H).

MS [EI, m/z]: 414 $[M]^+$.

Anal. Calcd. for $C_{29}H_{22}N_2O+0.4H_2O$: C 82.60, H 5.45, N 6.64. Found: C 82.71, H 5.44, N 6.54.

Step D. 10-[4-(Naphthalen-1-yl)benzoyl]-10,11-dihydro-5H-pyrrolo[2,1-c][1,4]benzodiazepine-3-carboxylic acid Prepared by treatment of [4-(naphthalen-1-yl)phenyl][10,11-dihydro-5H-pyrrolo[2,1c][1,4]benzodiazepin-10-yl]-methanone of Step C with trichloroacetyl chloride, followed by basic hydrolysis of the intermediate trichloroacetate ester in the manner of Example 1, Step F.

Step E. 10-[4-(Naphthalen-1-yl)benzoyl]-10,11-dihydro-5H-pyrrolo[2,1-c][1,4]benzodiazepine-3-carboxylic acid bis-(2-hydroxy-ethyl)-amide The title compound was prepared by coupling the 10-[4-(naphthalen-1-yl)benzoyl]-10,11-dihydro-5H-pyrrolo[2,1-c][1,4]benzodiazepine-3-carboxylic acid of Step D, with diethanolamine (1.25 equiv) in the manner of Example 1, Step G.

EXAMPLE 25

2-{4-[10-{[2-Chloro-4-(naphthalen-1-yl)phenyl]carbonyl}-(10,11-dihydro-5H-pyrrolo[2,1-c][1,4]benzodiazepin-3-yl)carbonyl]piperazine-1-yl}-1-hydroxyethane Step A. (4-Bromo-2-chloro-benzoyl)-(10,11H-dihydro-5H-pyrrolo[2,1-c][1,4]benzodiazepin-10-yl)-methanone N,N-Dimethylformamide (1 drop) was added to a solution of 4-bromo-2-chlorobenzoic acid (2.20 g, 9.35 mmol) in anhydrous tetrahydrofuran (20 mL). Oxalyl chloride (1.46 g, 11.46 mmol) was added and the mixture was warmed to reflux. The resultant solution was cooled to ambient temperature before being evaporated to dryness to give the crude acid chloride as a gold viscous liquid, which was used without further purification. To a mixture of 10,11-dihydro-5H-pyrrolo[2,1-c][1,4]benzodiazepine (1.44 g, 7.79 mmol) and triethylamine (0.95 g, 9.35 mmol) in dichloromethane (40 mL), cooled in an ice bath, was added dropwise a solution of the acid chloride in dichloromethane (20 mL). The cooling bath was removed and after stirring for 22 hours, the reaction mixture was washed sequentially with water, saturated aqueous sodium bicarbonate, 0.5 N hydrochloric acid and water. The dichloromethane solution was dried over anhydrous sodium sulfate, filtered, then evaporated to dryness to yield an off-white foam. Purification by flash chromatography on silica gel eluting with hexane-ethyl acetate (2:1) resulted in a white foam (3.02 g), m.p. 77–80° C. This material was used as such in the next step.

$^1H$ NMR (400 MHz, DMSO-$d_6$): δ 5.45 (br, 4H), 7.02 (t, 1H), 7.07 (td, 1H), 7.14 (td, 1H), 7.32 (br, 1H), 7.38 (d, 2H), 7.68 (br ,1H).

MS [EI, m/z]: 400 $[M]^+$.

Step B. [2-Chloro-4-naphthalen-1-yl-phenyl)-(10,11-dihydro-5H-pyrrolo[2,1-c][1,4]benzodiazepin-10-yl)-methanone 1-Naphthaleneboronic acid (0.52 g, 3.00 mmol) was added to a mixture of (4-bromo-2-chloro-benzoyl)-(10,11-dihydro-5H—pyrrolo[2,1-c][1,4]benzodiazepin-10-yl)-methanone of Step A (1.27 g, 3.15 mmol) and sodium carbonate (0.53 g, 4.98 mmol) in toluene (22.5 mL), ethanol (4.5 mL) and water (9 mL). The resultant solution was purged with nitrogen for 10 minutes, then tetrakis (triphenylphosphine) palladium (0.18 g, 0.06 mmol) was added. The reaction mixture was heated to reflux for 76 hours, cooled to ambient temperature, then filtered through a pad of Celite, which was subsequently rinsed with ethyl acetate. The combined filtrate was diluted to 100 mL water/ethyl acetate (1:1). The aqueous layer was extracted with ethyl acetate, and the combined organic layer was dried over anhydrous magnesium sulfate, filtered, and evaporated to dryness to yield a brown oil. Purification by flash chromatography on silica gel eluting with hexane-ethyl acetate (5:1) resulted in a white solid which was dried under vacuum (0.62 g), m.p. 115–117.5° C.

$^1H$ NMR (400 MHz, DMSO-$d_6$): δ 5.91 (t, 1H), 6.02 (br, 1H), 6.84 (br, 1H), 7.14 (m, 2H), 7.24 (d, 1H), 7.34, (d, 1H), 7.95 (d, 1H), 7.98 (d, 1H).

MS [(+)ESI, m/z]: 449 $[M+H]^+$.

Anal. Calcd. for $C_{29}H_{21}ClN_2O+0.25H_2O$: C 76.72, H 4.79, N 6.17. Found C 76.72, H 4.53, N 5.95.

Step C. 10-{[2-Chloro-4-(naphthalen-1-yl)phenyl]carbonyl}-10,11-dihydro-5H-pyrrolo[2,1-c][1,4]benzodiazepine-3-carboxylic acid Prepared by treatment of [2-chloro-4-(naphthalen-1-yl)-phenyl]-(10,11-dihydro-5H-pyrrolo[2,1-c][1,4]benzodiazepin-10-yl)-methanone of Step B with trichloroacetyl chloride, followed by basic hydrolysis of the intermediate trichloroacetate ester in the manner of Example 1, Steps E and F.

Step D. 2-{4-[10-{[2-Chloro-4-(naphthalen-1-yl)phenyl]carbonyl}-(10,11-dihydro-5H-pyrrolo[2,1-c][1,4]benzodiazepin-3-yl)carbonyl]piperazine-1-yl}-1-hydroxyethane The title compound was prepared from 10-{[2-chloro-4-(naphthalen-1-yl)phenyl]carbonyl}-10,11-dihydro-5H-pyrrolo[2,1-c][1,4]benzodiazepine-3-carboxylic acid of Step C and 1-(2-hydroxyethyl)-piperazine in the manner of Example 1, Step G.

HRMS [(+)ESI, m/z]: 605.23105 $[M+H]^+$. Calcd. for $C_{36}H_{34}ClN_4O_3$ 605.23140.

EXAMPLE 26

10-{[4-(4-Methyl-naphthalen-1-yl)phenyl]carbonyl}-10,11-dihydro-5H-pyrrolo[2,1-c][1,4]benzodiazepine-3-carboxylic acid (2,3-dihydroxy-propyl)-N-methylamide Step A. 4-(4-Methyl)-napthalen-1-yl-benzoic acid To a mixture of 1-bromo-4-methyl napthalene (1.11 g, 5.00 mmol) and 4-carboxyphenyl boronic acid (1.00 g, 6.00 mmol) in ethylene glycol dimethyl ether (20 mL) was added a solution of sodium carbonate (2.37 g, 22.38 mmol) in water (18.75 mL). The resultant mixture was purged with nitrogen for 20 minutes before tetrakis(triphenylphosphine) palladium(0) (0.03 g, 0.02 mmol) was added. The reaction mixture was heated to reflux for 68 hours. After the solution cooled to ambient temperature, the solvent was removed in vacuo and the residue was acidified with 5 N hydrochloric acid to produce and orange-brown solid that was isolated by vacuum filtration. This material was used without further purification in the next step.

$^1H$ NMR (300 MHz, DMSO-$d_6$): δ 2.70 (s, 3H), 7.57 (d, 2H), 8.07 (d, 2H).

Step B. [4-(4-Methyl-naphthalen-1-yl)phenyl][10,11-dihydro-5H-pyrrolo[2,1-c][1,4]benzodiazepin-10(11H)-yl]methanone N,N-Dimethylformamide (2 drops) was added to a solution of 4-(4-methyl)-napthalen-1-yl-benzoic acid of Step A (0.90 g, 3.43 mmol), in anhydrous tetrahydrofuran (10 mL). Oxalyl chloride (0.52 g, 4.12 mmol) was added and the mixture was warmed to reflux. The resultant solution was cooled to ambient temperature before being evaporated to dryness to give the crude acid chloride as a brown residue, which was used without further purification. To a mixture of 10,11-dihydro-5H-pyrrolo[2,1-c][1,4]benzodiazepine (0.53 g, 2.86 mmol) and triethylamine (0.35 g, 3.43 mmol) in dichloromethane (10 mL), cooled in an ice bath, was added dropwise a solution of the crude acid chloride in dichloromethane (10 mL). The cooling bath was removed and after stirring for 137 hours, the reaction mixture was washed sequentially with water, saturated aqueous sodium bicarbonate, and saturated aqueous sodium chloride. The dichloromethane solution was dried over anhydrous magnesium sulfate, filtered, then evaporated to dryness to yield an amber oil. Purification by flash chromatography on silica gel eluting with hexane-ethyl acetate (4:1) resulted in a tan foam (0.49 g). Treatment of this material with diethyl ether and sonication resulted in an off-white solid (0.37 g), m.p. 160–162° C.

$^1H$ NMR (400 MHz, DMSO-$d_6$): δ 2.66 (s, 3H), 5.32 (br, 4H), 5.93 (t, 1H), 5.97 (br, 1H), 6.83 (t, 1H), 7.01 (d, 1H), 7.22 (d, 2H), 7.28 (d, 2H), 7.39 (t, 3H), 7.45 (m, 2H), 7.57 (m, 2H), 8.06 (d, 1H).

MS [(+)ESI, m/z]: 429 $[M+H]^+$.

Anal. Calcd. for $C_{30}H_{24}N_2O$+0.13$H_2O$: C 83.63, H 5.67, N 6.50. Found: C 83.63, H 5.64, N 6.43

Step C. 10-{[4-(4-Methyl-naphthalen-1-yl)phenyl]carbonyl}-10,11-dihydro-5H-pyrrolo[2,1-c][1,4]benzodiazepine-3-carboxylic acid Prepared from [4-(4-methyl-naphthalen-1-yl)-phenyl]-[10,11-dihydro-5H-pyrrolo[2,1-c][1,4]benzodiazepine-10-yl]methanone of Step B by treatment with trichloroacetyl chloride, followed by basic hydrolysis of the intermediate trichloroacetate ester in the manner of Example 1, Steps E and F.

Step D. 10-{[4-(4-Methyl-naphthalen-1-yl)phenyl]carbonyl}-10,11-dihydro-5H-pyrrolo[2,1-c][1,4]benzodiazepine-3-carboxylic Acid (2,3-dihydroxy-propyl)-N-methylamide Prepared by the coupling of the 10-{[4-(4-methyl-naphthalen-1-yl)phenyl]carbonyl}-10,11-dihydro-5H-pyrrolo[2,1-c][1,4]benzodiazepine-3-carboxylic acid of Step C, with 3-methylamino-1,2-propanediol (1.2 equiv.) in the manner of Example 2.

EXAMPLE 27

10-[(3-Methoxy-2'-methyl-[1,1'-biphenyl]-4-yl)carbonyl]-10,11-dihydro-5H-pyrrolo[2,1-c][1,4]benzodiazepine-3-carboxylic acid methyl-[(2S,3R,4R,5R)-2,3,4,5,6-pentahydroxyhexyl]-amide Step A. 4-Iodo-2-methoxybenzoic acid methyl ester 4-Amino-2-methoxybenzoic acid methyl ester (3.0 g, 16.6 mmol) was suspended in water (40 mL) and concentrated sulfuric acid (10 mL). The suspension was cooled in an ice/salt water bath, and an aqueous solution (10 mL) of sodium nitrite (1.26 g, 18.3 mmol) was added dropwise so that the temperature remained close to 0° C. After the addition, a homogeneous, yellow-green solution was obtained. An aqueous solution (60 mL) of potassium iodide (3.02 g, 18.2 mmol) and iodine (2.31 g, 9.1 mmol) was then added dropwise, and the reaction stirred for an additional 1 hour. The reaction mixture was then extracted with ethyl acetate, the organic extracts were combined and washed with 1 N sodium thiosulfate, 1 N sodium hydroxide and brine. After drying over anhydrous sodium sulfate the solution was filtered and concentrated in vacuo to give 2.7 g of the title product as an orange oil which was used in the next step.

$^1H$ NMR (DMSO-$d_6$, 400 MHz): δ 2.76 (s, 3H), 3.82 (s, 3H), 7.39 (s, 2H), 7.48 (s, 1H).

MS [EI, m/z]: 292 $[M]^+$.

Step B. 4-lodo-2-methoxybenzoic acid

The 4-iodo-2-methoxybenzoic acid methyl ester of Step A (2.7 g, 9.24 mmol) was dissolved in tetrahydrofuran (40 mL) and 1 N sodium hydroxide (20 mL, 20 mmol) was added. The reaction mixture was heated at reflux for 3 hours, then cooled and concentrated in vacuo to give an orange oil that was partitioned between ethyl acetate and 2 N hydrochloric acid. The organic layer was dried over anhydrous sodium sulfate, filtered and concentrated in vacuo to give 2.5 g of title product as a yellow-orange solid, m.p. 144–146° C.

$^1H$ NMR (DMSO-$d_6$, 400 MHz): δ 3.81 (s, 3H), 7.37 (s, 2H), 7.44 (s, 1H), 12.72 (br, 1H).

MS [EI, m/z]: 278 $[M]^+$.

Anal. Calcd. for $C_8H_{7103}$+0.10 $C_4H_8O_2$: C 35.17, H 2.74. Found: C 35.37, H 2.49.

Step C. 10-(4-Iodo-2-methoxybenzoyl)-10,11-dihydro-5H-pyrrolo[2,1-c][1,4]benzodiazepine A suspension of 4-iodo-2-methoxybenzoic acid of Step B (2.5 g, 9.0 mmol) in thionyl chloride (10 mL) was heated at reflux for 1 hour. After cooling, the thionyl chloride was removed in vacuo. The residue was dissolved in toluene and concentrated in vacuo to give the crude acid chloride as a brown solid. The acid chloride was then dissolved in dichloromethane (10 mL) and slowly added to a solution of 10,11-dihydro-5H-pyrrolo[2,1-c][1,4]benzodiazepine (1.75 g, 9.5 mmol) and N,N-diisopropylethyl amine (3.4 mL, 19.5 mmol) in dichloromethane (20 mL). After stirring for 2 hours, the reaction was quenched with water. The organic layer was washed with 1 N hydrochloric acid, 1 N sodium hydroxide and brine, dried over anhydrous sodium sulfate, filtered and concentrated in vacuo to give a yellow foam. Purification by flash chromatography on silica gel using a solvent gradient of 15 to 25% ethyl acetate in hexane provided 3.6 g of title product as a white foam, which was redissolved in dichloromethane and evaporated to dryness prior to use in the next step.

$^1H$ NMR (DMSO-$d_6$, 400 MHz): δ 3.55 (br, 3H), 4.80–5.32 (br, 4H), 5.88–5.90 (m, 1H), 5.94 (s, 1H), 6.79 (s, 1H), 6.94 (s, 1H), 7.03 (t, 1H), 7.09–7.13 (m, 3H), 7.20–7.22 (m, 1H), 7.36–7.38 (m, 1H).

MS [(+)ESI, m/z]: 445 $[M+H]^+$.

Anal. Calcd. for $C_{20}H_{17}1N_2O_2$+0.10 $C_4H_8O_2$+0.13 $CH_2Cl_2$: C 53.13, H 3.92, N 6.04.

Found: C 53.03, H 3.65, N 6.03.

Step D. (10,11-Dihydro-5H-pyrrolo[2,1-c][1,4]benzodiazepin-10-yl)-[3-methoxy-2'-methyl-[1,1'-biphenyl]-4-yl]-methanone A mixture of 10-(4-iodo-2-methoxybenzoyl)-10,11-dihydro-5H-pyrrolo[2,1-c][1,4]benzodiazepine of Step C (1.8 g, 4.1 mmol), 2-methylphenyl boronic acid (0.55 g, 4.1 mmol) and sodium carbonate (1.9 g, 17.9 mmol) in toluene:ethanol: water (20 mL:10 mL:10 mL) was purged with nitrogen for 1 hour. After addition of the tetrakis (triphenylphosphine) palladium(0) catalyst (0.24 g, 0.21 mmol), the reaction mixture was heated at 100° C. overnight. After cooling, the reaction was filtered through Celite and the cake washed with ethyl acetate. The organic layer was washed with water, dried over anhydrous sodium sulfate, filtered and concentrated in vacuo to give a brown oil. Purification by flash chromatography on silica gel using a solvent system of 20% ethyl acetate in hexane provided 1.5 g of title product as a white foam, which was redissolved in dichloromethane and evaporated to dryness in vacuo prior to use in the next step.

$^1H$ NMR (DMSO-$d_6$, 400 MHz): δ 2.08 (s, 3H), 3.54 (s, 3H), 4.80–5.30 (br, 4H), 5.89–5.91 (m, 1H), 5.97 (s, 1H), 6.66 (s, 1H), 6.77–6.80 (m, 2H), 6.93–7.01 (m, 2H), 7.09–7.10 (m, 2H), 7.19–7.24 (m, 3H), 7.36–7.38 (m, 2H).

MS [(+)ESI, m/z]: 409 $[M+H]^+$.

Anal. Calcd. for $C_{27}H_{24}N_2O_2$+0.10 $CH_2Cl_2$: C 78.05, H 5.84, N 6.72. Found: C 78.12, H 5.13, N 6.69.

Step E. 2,2,2-Trichloro-1-{10-[(3-methoxy-2'-methyl-[1,1'-biphenyl]-4-yl)carbonyl]-10,11-dihydro-5H-pyrrolo[2,1-c][1,4]benzodiazepin-3-yl}ethanone To a solution of (10,11-dihydro-5H-pyrrolo[2,1-c][1,4]benzodiazepin-10-yl)-[3-methoxy-2'-methyl-[1,1'-biphenyl]-4-yl]-methanone of Step D (1.36 g, 3.33 mmol) in dichloromethane (15 mL) was added N,N-diisopropylethyl amine (1.2 mL, 6.89 mmol) followed by slow addition of trichloroacetyl chloride (1.1 mL, 9.85 mmol). The reaction mixture was stirred overnight at room temperature then was quenched with water. The organic phase was washed with 0.1 N hydrochloric acid followed by water, then dried over anhydrous sodium sulfate, filtered and concentrated in vacuo to give a green oil. Purification by flash chromatography on silica gel using a solvent system of 20% ethyl acetate in hexane gave 1.7 g of title product as a yellow foam.

$^1$H NMR (DMSO-$d_6$, 400 MHz): δ 2.09 (s, 3H), 3.50 (s, 3H), 5.30 (br, 2H), 5.87 (br, 2H), 6.37–6.38 (m, 1H), 6.64 (s, 1H), 6.82–6.83 (m, 1H), 6.90–6.92 (m, 1H), 6.97–6.99 (m, 1H), 7.10–7.12 (m, 2H), 7.20–7.25 (m, 4H), 7.35–7.37 (m, 1H), 7.44–7.46 (m, 1H).

MS [(+)APCI, m/z]: 553 $[M+H]^+$.

Anal. Calcd. for $C_{29}H_{23}C_{13}N_2O_3$+0.20 $C_4H_8O_2$+0.40$H_2O$: C 61.85, H 4.42, N 4.84.

Found: C 61.50, H 4.07, N 4.72.

Step F. 10-[(3-Methoxy-2'-methyl-[1,1'-biphenyl]-4-yl)carbonyl]-10,11-dihydro-5H-pyrrolo[2,1-c][1,4]benzodiazepine-3-carboxylic acid To a solution of 2,2,2-trichloro-1-{10-[(3-methoxy-2'-methyl[1,1'-biphenyl]-4-yl)carbonyl]-10,11-dihydro-5H-pyrrolo[2,1-c][1,4]benzodiazepin-3-yl}ethanone of Step E (1.6 g, 2.9 mmol) in acetone (20 mL) was added 2.5 N sodium hydroxide (2.3 mL, 5.8 mmol). After stirring overnight, the reaction was acidified with 2 N hydrochloric acid (3.2 mL, 6.4 mmol) then concentrated in vacuo. The residue was partitioned between ethyl acetate and water. The layers were separated, and the organic layer was dried over anhydrous sodium sulfate, filtered and concentrated in vacuo to give a brown solid. Trituration with diethyl ether/hexane provided 1.2 g of desired product as an off-white solid, m.p. 201–204° C.

$^1$H NMR (DMSO-$d_6$, 400 MHz): δ 2.09 (s, 3H), 3.48 (s, 3H), 5.20 (br, 2H), 5.85 (br, 2H), 6.12 (s, 1H), 6.62 (s, 1H), 6.73 (d, 1H), 6.79–6.87 (m, 2H), 6.91–6.95 (m, 1H), 6.99–7.03 (m, 1H), 7.06–7.12 (m, 1H), 7.18–7.25 (m, 4H), 7.39 (br, 1H), 12.31 (br, 1H).

MS [(+) ESI, m/z]: 453 $[M+Na]^+$.

Anal. Calcd. for $C_{28}H_{24}N_2O_4$+0.10 $C_4H_{10}0$ +0.15 $C_4H_8O_2$: C 73.61, N 5.92.

Found: C 73.23, H 5.49, N 6.06.

Step G. 10-[(3-Methoxy-2'-methyl-]1,1'-biphenyl[-4-yl)carbonyl]-10,11-dihydro-5H-pyrrolo[2,1-c][1,4]benzodiazepine-3-carboxylic acid methyl-[(2S,3R,4R,5R)-2,3,4,5,6-pentahydroxy-hexyl]-amide To a solution of 10-[(3-methoxy-2'-methyl-[1,1'-biphenyl]-4-yl)carbonyl]-10,11-dihydro-5H-pyrrolo[2,1-c][1,4]benzodiazepine-3-carboxylic acid of Step F, N-methyl-D-glucamine and 1-hydroxybenzotriazole in N,N-dimethylformamide was added 1-[3-(dimethylamino)propyl]-3-ethyl carbodiimide hydrochloride followed by N,N-diisopropylethylamine in the manner of Example 17. The reaction mixture was stirred overnight, then diluted with ethyl acetate and washed with water and saturated aqueous sodium bicarbonate. The organic phase was then dried over anhydrous sodium sulfate, filtered and concentrated in vacuo to give a yellow foam. Purification by flash chromatography on silica gel using a solvent system of 5% methanol in dichloromethane afforded the title compound as a white foam.

EXAMPLE 28

{10-[(2'-Chloro-6-chloro-3-methoxy-[1,1'-biphenyl]-4-yl)carbonyl]-10,11-dihydro-5H-pyrrolo[2,1-c][1,4]benzodiazepine-3-yl}[(2S, 5S)-bis-hydroxymethyl-(3R, 4R)-bis-hydroxy-pyrrolidin-1-yl]-methanone Step A. 2'-Chloro-2-chloro-5-methoxy-[1,1'-biphenyl]-4-carboxylic acid.

To a stirred solution of 4-iodo-5-chloro-2-methoxy benzoic acid (3.12 g, 10 mmol) of Example 20, Step A in N,N-dimethylformamide (100 mL) was added 2-chlorophenyl boronic acid (5.07 g, 32.4 mmol) and potassium carbonate (12.73 g, 92 mmol). This mixture was purged with nitrogen and then treated with tetrakis (triphenylphosphine) palladium(0) (0.58 g, 0.5 mmol). The reaction was heated to reflux overnight, cooled, acidified with 2 N hydrochloric acid and extracted with ethyl acetate. The organic layer was washed with brine, dried over anhydrous magnesium sulfate, filtered, and evaporated to provide a nearly quantitative amount of the title acid which was used in the next step without further purification.

Step B. 10-{[2'-Chloro-6-chloro-3-methoxy-[1,1'-biphenyl]-4-yl]carbonyl}-10,11-dihydro-5H-pyrrolo[2,1-c][1,4]benzodiazepine A stirred solution of the 2'-chloro-2-chloro-5-methoxy-[1,1'-biphenyl]-4-carboxylic acid of Step A (3.09 g, 10.46 mmol) in tetrahydrofuran (20 mL) containing a catalytic amount of N,N-dimethylformamide was treated dropwise with thionyl chloride (1.36 g, 11.51 mmol). The reaction mixture was stirred for 2 hours, and then added dropwise to a solution of 10,11-dihydro-5H-pyrrolo[2,1-c][1,4]benzodiazepine (1.92 g 10.46 mmol) in tetrahydrofuran (20 mL) containing triethylamine (2.32 g, 23 mmol). The reaction mixture was stirred for 2 hours, diluted with dichloromethane and washed with saturated aqueous sodium bicarbonate and brine. The organic layer was dried over anhydrous magnesium sulfate, filtered, and evaporated to dryness. Trituration of the residue with ethyl acetate gave the title compound (1.93 g) which was recrystallized from ethyl acetate/hexanes as white crystals, m.p. 209–211° C.;

$^1$H NMR (DMSO-$d_6$, 400 MHz) δ 3.55 (s, 3H), 5.16–5.20 (br m, 3H), 5.89 (t, 1H), 5.97 (s, 1H), 6.71 (s, 1H), 6.80 (s, 1H), 7.04–7.60 (m, 10H).

MS [(+) APCI, m/z]: 463 $[M+H]^+$.

Anal. Calcd. for $C_{26}H_{20}C_2N_2O_2$+0.25 $C_4H_8O_2$: C 66.81, H 4.57, N 5.77, Found: C 66.76, H 4.24, N 5.93.

Step C. 10-{[2'-Chloro-6-chloro-3-methoxy-[1,1'-biphenyl]-4-yl]carbonyl}-10,11-dihydro-5H-pyrrolo[2,1-c][1,4]benzodiazepine-3-carboxylic acid A solution of 10-{[2'-chloro-6-chloro-3-methoxy-[1,1'-biphenyl]-4-yl]carbonyl}-10,11-dihydro-5H-pyrrolo[2,1-c][1,4]benzodiazepine of Step B (2.1 g, 4.6 mmol) in dichloromethane (30 mL) was treated with N,N-diisopropylethyl amine (0.62 g, 4.84 mmol) and stirred for 10 minutes. Trichloroacetyl chloride (0.92 g, 5.07 mmol) was then added dropwise. The reaction mixture was stirred overnight, diluted with dichloromethane, washed with 0.1 N hydrochloric acid, saturated aqueous sodium bicarbonate, and brine. The organic phase was dried over anhydrous magnesium sulfate, filtered, and evaporated to yield the crude trichloroketone intermediate which without further purification, was dissolved in acetone and treated with an excess of 1 N sodium hydroxide. The mixture was stirred overnight, diluted with isopropyl acetate and acidified with 1 N hydrochloric acid. The organic layer was washed with brine, dried over anhydrous magnesium sulfate, filtered, and evaporated to dryness. The solid residue was triturated with methanol to provide the title compound as a white solid, which was used without further purification.

Step D. {10-[(2'-Chloro-6-chloro-3-methoxy-[1,1'-biphenyl]-4-yl)carbonyl]-10,11-dihydro-5H-pyrrolo[2,1-c][1,4]benzodiazepine-3-yl}[(2S, 5S)-bis-hydroxymethyl-(3R, 4R)-bis-hydroxy-pyrrolidin-1-yl]-methanone The title compound was prepared in the manner of Example 1, Step G, by the coupling of the 10-{[2'-chloro-6-chloro-3-methoxy-[1,1'-biphenyl]-4-yl]carbonyl}-10,11-dihydro-5H-pyrrolo[2,1-c][1,4]benzodiazepine-3-carboxylic acid of Step C with (2S, 5S)-bis-hydroxymethyl-(3R, 4R)-bis-hydroxy-pyrrolidine [prepared in the manner of Bennani et al., EP 0 558 395 A1 (1993)].

EXAMPLE 29

10-[(6-Chloro-2'-ethoxy-3-methoxy-[1,1'-biphenyl]-4-yl)carbonyl]-N-methyl-10,11-dihydro-5H-pyrrolo[2,1-c][1,4]benzodiazepine-3-carboxylic acid methyl-(2,3,4-trihydroxy-butyl)-amide Step A. 2-Chloro-2'-ethoxy-5-methoxy[1,1'-biphenyl]-4-carboxylic acid To a stirred solution of 4-iodo-5-chloro-2-methoxy benzoic acid of Example 15, Step A (0.500 g, 1.6 mmol) in N,N-dimethylformamide (30 mL) was added 2-ethoxy phenyl boronic acid (0.8 g, 4.8 mmol) and potassium carbonate (2.04 g, 14.7 mmol). This mixture was purged with nitrogen and then treated with a catalytic amount of tetrakis (triphenylphosphine) palladium(0) (0.093 g, 0.08 mmol). The reaction was heated to reflux overnight, cooled, acidified with 2 N hydrochloric acid and extracted with ethyl acetate. The organic layer was washed with brine, dried over anhydrous magnesium sulfate, filtered, and evaporated to yield the title acid which was used in the next step without further purification.

Step B. 10-{[6-Chloro-3-methoxy-2'-ethoxy-[1,1'-biphenyl]-4-yl]carbonyl}-10,11-dihydro-5H-pyrrolo[2,1-c][1,4]benzodiazepine To a stirred solution of the 2-chloro-2'-ethoxy-5-methoxy[1,1'-biphenyl]-4-carboxylic acid of Step A (0.491 g) in tetrahydrofuran (5 mL) containing a catalytic amount of N,N-dimethylformamide was added dropwise thionyl chloride (0.210 g, 1.76 mmol). The reaction mixture was stirred for 2 hours, and then added dropwise to a solution of 10,11-dihydro-5H-pyrrolo[2,1-c][1,4]benzodiazepine (0.294 g, 1.60 mmol) in tetrahydrofuran (5 mL) containing triethylamine (0.357 g, 3.52 mmol). The reaction mixture was stirred for 2 hours, diluted with dichloromethane and washed with saturated aqueous sodium bicarbonate and brine. The organic layer was dried over anhydrous magnesium sulfate, filtered, and evaporated to dryness. Trituration of the residue with methanol provided the title compound as an off-white solid, 99.24% pure by analytical HPLC [Primesphere C-18 column (2.0×150 mm); mobile phase 70/30 acetonitrile/water containing 0.1% phosphoric acid], m.p. 213–215° C.

$^1$H NMR (DMSO-$d_6$, 400 MHz): δ 1.11, (t, 3H), 3.51 (s, 3H), 3.92 (q, 2H), 5.17–5.20 (br, m, 3H), 5.89 (t, 1H), 5.97 (s, 1H), 6.67–7.55 (m, 10H).

MS [(+)APCI, m/z]: 473 $[M+H]^+$.

Anal. Calcd. for $C_{28}H_{25}ClN_2O_3$: C 71.11, H 5.33, N 5.92. Found: C 70.31, H 5.27, N 5.79.

Step C. 10-{[6-Chloro-3-methoxy-2'-ethoxy[1,1'-biphenyl]-4-yl]carbonyl}-10,11-dihydro-5H-pyrrolo[2,1-c][1,4]benzodiazepine-3-carboxylic acid Prepared by treatment of 10-{[6-chloro-3-methoxy-2'-ethoxy-1,1'-biphenyl]-4-yl]carbonyl}-10,11-dihydro-5H-pyrrolo[2,1-c][1,4]benzodiazepine of Step B with trichloroacetyl chloride, followed by basic hydrolysis of the intermediate trichloroacetate ester in the manner of Example 1, Step F.

Step D. 10-[(6-Chloro-2'-ethoxy-3-methoxy-[1,1'-biphenyl]-4-yl)carbonyl]-N-methyl-10,11-dihydro-5H-pyrrolo[2,1-c][1,4]benzodiazepine-3-carboxylic acid methyl-(2,3,4-trihydroxy-butyl)-amide Obtained by coupling the 10-{[6-chloro-3-methoxy-2'-ethoxy[1,1'-biphenyl]-4-yl]carbonyl}-10,11-dihydro-5H-pyrrolo[2,1-c][1,4]benzodiazepine-3-carboxylic acid of Step C with 4-methylamino-butane-1,2,3-triol [prepared in the manner of Bennani et al., EP 0 558 395 A1 (1993)] (1.25 equiv.) in the manner of Example 2.

EXAMPLE 30

N-(2,3-Dihydroxy-propyl)-N-(2,3,4-trihydroxy-butyl)-10-{[6-chloro-2'-fluoro-3-methoxy-[1,1'-biphenyl]-4-yl]carbonyl}-10,11-dihydro-5H-pyrrolo[2,1-c][1,4]benzodiazepine-3-carboxamide Step A. 2-Chloro-2'-fluoro-5-methoxy[1,1'-biphenyl]-4-carboxylic acid To a stirred solution of 4-iodo-5-chloro-2-methoxy benzoic acid of Example 20, Step A (3.72 g, 19.1 mmol) in N,N-dimethylformamide (20 mL) was added 2-fluorophenyl boronic acid (5.0 g, 35.7 mmol) and potassium carbonate (14.8 g, 107 mmol). This mixture was purged with nitrogen and then treated with a catalytic amount of tetrakis (triphenylphosphine) palladium(0) (0.688 g, 0.59 mmol). The reaction was heated to reflux overnight, cooled, acidified with 2 N hydrochloric acid and extracted with ethyl acetate. The organic layer was washed with brine, dried over anhydrous magnesium sulfate, filtered, and evaporated to dryness. The residue was flash chromatographed on acid washed silica using a 10 to 50% gradient of diethyl ether in hexane to provide the desired title compound (3.8 g) as a white solid.

$^1$H NMR (DMSO-$d_6$, 400 MHz): δ 3.83 (s, 3H), 7.15 (s, 1H), 7.30–7.35 (m, 2H), 7.42 (m, 1H), 7.48–7.54 (m, 1H), 7.74 (s, 1H).

MS [(+)ESI, m/z]: 298 $[M+NH_4]^+$.

Anal. Calcd. for $C_{14}H_{10}ClFO_3$: C 59.91, H 3.59. Found: C 59.79, H 3.35.

Step B. 10-{[6-Chloro-3-methoxy-2'-fluoro-[1,1'-biphenyl]-4-yl]carbonyl}-10,11-dihydro-5H-pyrrolo[2,1-c][1,4]benzodiazepine To a stirred solution of 2-chloro-2'-fluoro-5-methoxy[1,1'-biphenyl]-4-carboxylic acid of Step A (3.80 g, 13.5 mmol) in tetrahydrofuran (20 mL) containing a catalytic amount of N,N-dimethylformamide was added dropwise thionyl chloride (1.77 g, 14.9 mmol). The reaction mixture was stirred for 2 hours, and then added dropwise to a solution of 10,11-dihydro-5H-pyrrolo[2,1-c][1,4]benzodiazepine (2.49 g, 13.5 mmol) in tetrahydrofuran (20 mL) containing triethylamine (3.0 g, 29.8 mmol). The reaction mixture was stirred for 2 hours, diluted with dichloromethane and washed with saturated aqueous sodium bicarbonate and brine. The organic layer was dried over anhydrous magnesium sulfate, filtered, and evaporated to dryness. Recrystallization of the residue from ethyl acetate/heptane provided the title compound as a pale yellow solid, m.p. 192–194° C., found to be 99.99% pure by analytical HPLC [Primesphere C-18 column (2.0×150 mm); mobile phase: gradient from 10 to 100% of acetonitrile/water containing 0.1% phosphoric acid, 7 minute gradient].

$^1$H NMR (DMSO-$d_6$, 400 MHz) δ 3.55 (s, 3H), 5.19 (br m, 2H), 5.90 (t, 1H), 5.96 (s, 1H), 6.80 (s, 2H), 7.07–7.63 (m, 10H).

MS [(+)ESI, m/z]: 447 $[M+H]^+$.

Anal. Calcd. for $C_{26}H_{20}ClFN_2O_2+H_2O$: C 69.60, H 4.54, N 6.24. Found: C 69.39, H 4.41, N 6.20.

Step C. 10-{[6-Chloro-3-methoxy-2'-fluoro-[1,1'-biphenyl]-4-yl]carbonyl}-10,11-dihydro-5H-pyrrolo[2,1-c][1,4]benzodiazepine-3-carboxylic acid A solution of the 10-{[6-chloro-3-methoxy-2'-fluoro-[1,1'-biphenyl]-4-yl]carbonyl}-10,11-dihydro-5H-pyrrolo[2,1-c][1,4]benzodiazepine of Step B (3.02 g, 6.76 mmol) in dichloromethane (35 mL) was treated with N,N-diisopropylethyl amine (0.960 g, 7.43 mmol) and stirred for 10 minutes. Trichloroacetyl chloride (1.47 g, 8.10 mmol) was then added dropwise. The reaction mixture was stirred overnight, diluted with dichloromethane, washed with 0.1 N hydrochloric acid, saturated aqueous sodium bicarbonate, and brine. The organic phase was dried over anhydrous magnesium sulfate, filtered, and evaporated to yield the crude trichloroketone intermediate which without further purification, was dissolved in acetone and treated with an excess of 1 N sodium hydroxide. The mixture was stirred overnight, and then diluted with isopropyl acetate and acidified with 1 N hydrochloric acid. The organic layer was washed with brine, dried over anhydrous magnesium sulfate, filtered, and evaporated to dryness. The solid residue was triturated with methanol to provide the title compound (2.95 g) as a beige solid, m.p. 207–208° C.

$^1$H NMR (DMSO-$d_6$, 400 MHz) δ 3.49 (br, 3H), 6.12 (d, 1H), 6.72 (d, 1H), 6.77 (s, 1H), 7.01 (d, 2H), 7.09 (m, 1H), 7.26 (m, 4H), 7.45 (m, 2H), 7.61 (br, 1H), 12.35 (br, 1H).

MS [(+)APCI, m/z]: 491 $[M+H]^+$.

Anal. Calcd for $C_{27}H_{20}ClFN_2O_4$: C 66.06, H 4.11, N 5.71. Found: C 65.68, H 4.24, N 5.48.

Step D. N-(2,3-Dihydroxy-propyl)-N-(2,3,4-trihydroxy-butyl)-110-{[6-chloro-2'-fluoro-3-methoxy-[1,1'-biphenyl]-4-yl]carbonyl}-10,11-dihydro-5H-pyrrolo[2,1-c][1,4]benzodiazepine-3-carboxamide The title compound was obtained in the manner of Example 1, Step F by coupling the [(6-chloro-3-methoxy-2'-fluoro-[1,1'-biphenyl]-4-yl)carbonyl]-10,11-dihydro-5H-pyrrolo[2,1-c][1,4]benzodiazepine-3-carboxylic acid of Step C, with 4-(2,3-dihydroxy-propylamino)-butane-1,2,3-triol (1.25 equiv.) [prepared in the manner of Bennani et al., EP 0 558 395 B1 (1993)].

EXAMPLE 31

N-Methyl-N-(2-hydroxy-1,1-bis-hydroxymethyl-ethyl)-{[10-(2-methoxy)-2'-methoxy-[1,1'-biphenyl]-4-yl]carbonyl}-10,11-dihydro-5H-pyrrolo[2,1-c][1,4]benzodiazepin-3-carboxamide 10-{[2-Methoxy-2'-chloro-[1,1'-biphenyl]-4-yl]carbonyl}-10,11-dihydro-5H-pyrrolo[2,1-c][1,4]benzodiazepine-3-carboxylic acid (0.230 g, 0.54 mmol) [prepared from trifluoromethanesulfonic acid 4-formyl-2-methoxy-phenyl ester of Example 21, Step A and 2-chlorophenyl boronic acid, in the manner of Example 21, Steps B-E], 1-[3-(dimethylamino)propyl]-3-ethylcarbodiimide hydrochloride (0.120 g, 0.625 mmol) and 1-hydroxybenzotriazole (0.087 g, 0.625 mmol) were added to a flask containing N,N-dimethylformamide (15 mL). To the homogeneous solution was added 2-hydroxymethyl-2-methylamino-propane-1,3-diol [prepared in the manner of Bennani et al., EP 0 558 395 A1 (1993)] (0.625 mmol) and stirring continued at room temperature overnight. At the end of this time the solution was poured into water and extracted with ethyl acetate. The combined extracts were washed with water, dried and concentrated and the residue was chromatographed on silica gel using a solvent system of 5% methanol in chloroform to provide the title product

EXAMPLE 32

N-(2-Hydroxy-ethyl)-N-(2',3',4'-trihydroxy-butyl)-110-[(3,6-dimethoxy-2'-trifluoromethyl-[1,1'-biphenyl]-4-yl)carbonyl]-10,11-dihydro-5H-pyrrolo[2,1-c][1,4]benzodiazepine-3-carboxamide Step A. 2,5-Dimethoxy-2'-trifluoromethyl-[1,1'-biphenyl]-4-carboxylic acid A suspension of 4-bromo-2,5-dimethoxybenzoic acid [prepared in the manner of Bortnik et al., *Zh. Org. Khim.* 8, 340 (1972)] (2.43 g, 9 mmol), 2-trifluoromethyl phenyl boronic acid (5.3 g, 28 mmol), and potassium carbonate (6.21 g, 60 mmol) in dioxane (40 mL) was sparged with nitrogen and treated with tetrakis(triphenylphosphine) palladium(0) (0.328 g, 0.2 mmol). The mixture was heated to reflux for 48 hours, cooled, acidified with 1 N hydrochloric acid and extracted with ethyl acetate The extracts were dried over anhydrous magnesium sulfate, filtered and stripped to a solid which was used as such in the next step $^1$H NMR (300 MHz, $CDCl_3$): δ 3.90 (s, 3H), 4.05 (s, 3H), 7.30 (d, 1H), 7.70 (s, 1H).

Step B. 10-{[3,6-Dimethoxy-2'-trifluoromethyl-[1,1'-biphenyl]-4-yl]carbonyl}-[10,11-dihydro-5H-pyrrolo[2,1-c][1,4]benzodiazepine The title compound was prepared in the manner of Example 33, Step A using 2,5-dimethoxy-2'-trifluoromethyl-[1,1'-biphenyl]-4-carboxylic acid of Step A (1.63 g, 5 mmol), oxalyl chloride (700 μL, 8 mmol), N,N-dimethylformamide (10 μL), 10,11-dihydro-5H-pyrrolo[2,1-c][1,4]benzodiazepine (0.93 g, 5 mmol) and H ünig's base (1.78 ml, 10 mmol). Flash chromatography over silica gel using a solvent gradient from 30% ethyl acetate in hexane to 100% ethyl acetate provided the title compound (0.900 g) as a solid. Recrystallization from acetone/hexane yielded white needles, m.p. 210–213° C.

$^1$H NMR (400 MHz, DMSO-$d_6$: 6 3.41 (s, 3H), 3.56 (s, 3H), 5.21 (br, 4H), 5.90 (t, 1H), 5.96 (s, 1H), 6.50 (s, 1H), 6.80 (s, 1H), 7.00 (s, 2H), 7.07 (s, 1H), 7.10 (t, 1H), 7,18 (d, 1H), 7.37 (d, 1H), 7.53 (t, 1H), 7.62 (t, 1H), 7.73 (d, 1H).

MS [(+)ESI, m/z]: 493 $[M+H]^+$.

Anal. Calcd. for $C_{28}H_{23}F_3N_2O_3$: C 68.29, H 4.71, N 5.69. Found: C 67.98, H 4.66, N 5.61.

Step C. 10-{[3,6-Dimethoxy-2'-trifluoromethyl-[1,1'-biphenyl]-4-yl]-carbonyl}-10,11-dihydro-5H-pyrrolo[1,2-c][1,4]benzodiazepine-3-carboxylic acid Prepared from 10-{[3,6-dimethoxy-2'-trifluoromethyl-[1,1'-biphenyl]-4-yl]-carbonyl}-10,11-dihydro-5H-pyrrolo[2,1-c][1,4]benzodiazepine of Step B and trichloroacetyl chloride, followed by basic hydrolysis of the intermediate trichloroacetate ester, in the manner of Example 1, Steps E and F.

Step D. N-(2-Hydroxy-ethyl)-N-(2',3',4'-trihydroxy-butyl)-10-[(3,6-dimethoxy-2'-trifluoromethyl-[1,1'-biphenyl]-4-yl)carbonyl]-10,11-dihydro-5H-pyrrolo[2,1-c][1,4]benzodiazepine-3-carboxamide The title compound was obtained in the manner of Example 2, by coupling the 10-[(3,6-dimethoxy-2'-trifluoromethyl-[1,1'-biphenyl]-4-yl]-carbonyl}-10,11-dihydro-5H-pyrrolo[1,2-c][1,4]benzodiazepine-3-carboxylic acid of Step C and 4-[(2-hydroxy-ethylamino)-butane -1,2,3-triol (1 equiv.) [prepared in the manner of Bennani et al., EP 0 558 395 A1 (1993)].

EXAMPLE 33

N-(2,3-Dihydroxy-propyl)-N-(1-hydroxymethyl-2,3-dihydroxy-propyl)-10-{[3-methyl-4-(4-pyridinyl)phenyl]carbonyl}-10,11-dihydro-5H-pyrrolo[2,1-c][1,4]benzodiazepine-3-carboxamide Step A. (4-Bromo-3-methylphenyl)[10,11-dihydro-5H-pyrrolo[2,1-c][1,4]benzodiazepin-10-yl]methanone A solution of 4-bromo-3-methyl benzoic acid (4.3 g, 2 mmol) in dry tetrahydrofuran (100 mL) was cooled to 0° C. under nitrogen. To this was added N,N-dimethylformamide (50 $\mu$L) followed by oxalyl chloride (2.2 mL, 25 mmol) dropwise to control the gas evolution. When the gas evolution ceased, the mixture was warmed to reflux for 5 minutes then cooled to room temperature and concentrated in vacuo. The sample was treated with tetrahydrofuran and evaporated to dryness (twice) to yield the crude acid chloride as an orange oil. A solution of 10,11-dihydro-5H-pyrrolo[2,1-c][1,4]benzodiazepine (3.60 g, 20 mmol) and Hünig's base (4.35 mL, 25 mmol) in dichloromethane was cooled to 0° C., and a solution of the crude acid chloride in dichloromethane (25 mL) was added dropwise. The mixture was stirred overnight at room temperature, washed with 1 N hydrochloric acid, saturated aqueous sodium bicarbonate and brine. The solution was dried over anhydrous sodium sulfate, filtered and evaporated in vacuo to yield a solid (8.01 g) which was purified by flash chromatography on silica gel eluting with 20% ethyl acetate in hexane to provide the title compound (6.03 g) as a white solid.

$^1$H NMR (300 MHz, $CDCl_3$): δ 2.30 (s, 3H), 5.20 (br, 4H), 6.05 (d, 2H), 6.70 (s, 1H), 6.85 (br, 2H), 7.17 (m, 2H), 7.30 (m, 2H), 7.37 (d, 1H).

Step B. [3-Methyl-4-(pyridin-4-yl)phenyl]-[10,11-dihydro-5H-pyrrolo[2,1-c][1,4]-benzodiazepin-10-yl]methanone A suspension of (4-bromo-3-methylphenyl)-[10,11-dihydro-5H-pyrrolo[2,1-c][1,4]benzodiazepin-10-yl] methanone of Step A (1.14 g, 2.9 mmol), pyridine-4-boronic acid (0.368 mg, 2.9 mmol) and sodium carbonate (0.760 g, 7.2 mmol) in a mixture of toluene (30 mL), water (10 mL), and ethanol (5 mL) was sparged with nitrogen for 15 minutes. To this was added tetrakis(triphenylphosphine) palladium(0) (0.027 g) and the mixture was heated to reflux under a static pressure of nitrogen. After 24 hours additional boronic acid (0.128 mg, 1 mmol) and sodium carbonate (0.116 g) were added and the heating was continued for 24 hours. Additional catalyst (0.012 g) was added and heating was continued for another 24 hours. The mixture was partitioned between ethyl acetate and hexane. The water layer was washed twice with ethyl acetate and the combined organic layers were dried over anhydrous magnesium sulfate and stripped to a solid. Flash chromatography of the residue on silica gel eluting with 30% ethyl acetate in hexane provided 0.379 g of the desired product which was recrystallized from ethyl acetate/hexanes as tan plates, m.p. 208–210° C.

$^1$H NMR (400 MHz, DMSO-$d_6$): δ 1.75 (s, 3H), 1.77 (s, 3H), 5.18 (br s, 4H), 5.89 (s, 2H), 6.05 (brs, 1H), 6.08 (t, 1H), 6.69 (t, 1H), 6.85 (brs, 1H), 7.03 (brs, 3H), 7.16 (t, 1H), 7.35 (d, 1H)

MS [(+)ESI, m/z]: 379 $[M]^+$.

Anal. Calc'd for $C_{25}H_{21}N_3O$+0.5$H_2O$: C 77.30, H 5.71, N 10.82. Found: C 77.01, H 5.37, N 10.68

Step C. 10-[3-Methyl-4-(4-pyridinyl)benzoyl]-10,11-dihydro-5H-pyrrolo[2,1-c][1,4]benzodiazepine-3-carboxylic acid To a stirred solution of [3-methyl-4-(pyridin-4-yl)phenyl] [10,11-dihydro-5H-pyrrolo[2,1-c][1,4]benzodiazepin-10-yl] methanone of Step B (5 mmol) and N,N-diisopropylethyl amine (12 mmol) in dichloromethane (200 mL) cooled to 0° C. was added dropwise a solution of trichloroacetyl chloride (12 mmol) in dichloromethane. The temperature was maintained at 0° C. until the addition was complete. The reaction was stirred overnight as it warmed to room temperature. The solution was then washed with 10% aqueous sodium bicarbonate and the organic layer was dried, concentrated and filtered through a pad of silica gel with 1:1 ethyl acetate/hexane containing 0.1% acetic acid. The filtrate was concentrated in vacuo and the residue was dissolved in acetone and 1N sodium hydroxide (2:1,v/v) and stirred at room temperature for 1 hour and then the pH was adjusted to pH 4 with glacial acetic acid. The solution was concentrated to one half the volume in vacuo and the residue extracted with ethyl acetate. The combined organic layers were dried and evaporated to an oil which was triturated with hexane to yield a solid (0.98 g).

Step D. N-(2,3-Dihydroxy-propyl)-N-(1-hydroxymethyl-2,3-dihydroxy-propyl)-10-{[3-methyl-4-(4-pyridinyl)phenyl] carbonyl}-10,11-dihydro-5H-pyrrolo[2,1-c][1,4] benzodiazepine-3-carboxamide The title compound was obtained in the manner of Example 1, Step G from the 10-[3-methyl-4-(4-pyridinyl) benzoyl]-10,11-dihydro-5H-pyrrolo[2,1-c][1,4] benzodiazepine-3-carboxylic acid of Step C and 3-(2,3-dihydroxy-propylamino)-butane-1,2-4-triol (1.2 equiv.) [prepared in the manner of Bennani et al., EP 0 558 395 A1 (1993)].

EXAMPLE 34

10-[(6-Phenyl-pyridin-3-yl)-carbonyl]-10,11-dihydro-5H-pyrrolo[2,1-c][1,4]benzodiazepine-3-carboxylic acid bis-(2-hydroxy-ethyl)-amide Step A. 10-(Methoxycarbonyl)-10,11-dihydro-5H-pyrrolo[2,1-c][1,4]benzodiazepine-3-carboxylic acid A solution of 10,11-dihydro-5H-pyrrolo[2,1-c][1,4] benzodiazepine (5 mmol) and N,N-diisopropylethyl amine (12 mmol) in dichloromethane (100 mL) was cooled to 0° C. and treated dropwise with trichloroacetyl chloride (12 mmol) in dichloromethane (20 mL). The solution was maintained at 0° C. for two hours and then allowed to warm to room temperature overnight. The solution was then treated with methanol (25 mL) and stirring was continued for 2 hours. The solution was washed with 0.1 N hydrochloric acid, water and brine, dried over anhydrous magnesium sulfate, filtered and concentrated to yield the title compound as a white solid, m.p. 153–154° C. (dec.).

Anal. Calcd. for $C_{15}H_{14}N_2O_4$+0.06 $C_4H_8O_2$+0.07 $C_3H_6O$: C 62.77, H 5.08, N 9.48.

Found: C 62.26, H 5.22, N 9.37.

Step B. 10-(Methoxycarbonyl)-10,11-dihydro-5H-pyrrolo[2,1-c][1,4]benzodiazepine-3-carboxylic acid bis-(2-hydroxy-ethyl)-amide The title compound was prepared by coupling the 10-(methoxycarbonyl)-10,11-dihydro-5H-pyrrolo[2,1-c][1,4] benzodiazepine-3-carboxylic acid of step A with diethanolamine (1.2 equiv.), in the manner of Example 1, Step G, Step C. 10,11-Dihydro-5H-pyrrolo[2,1-c][1,4] benzodiazepine-3-carboxylic acid bis-(2-hydroxy-ethyl)-amide A solution of 10-(methoxycarbonyl)-10,11-dihydro-5H-pyrrolo[2,1-c][1,4]benzodiazepine-3-carboxylic acid bis-(2-hydroxy-ethyl)-amide (5 mmol) of Step B in methanol (50 mL) was treated with potassium carbonate and stirred at room temperature overnight. Water was then added to the solution and the pH adjusted to 6 with 6N hydrochloric acid. The solution was saturated with solid sodium chloride and extracted with dichloromethane. The combined organic layers were dried over anhydrous magnesium sulfate and evaporated to dryness to yield the title compound.

Step D. 10-[(6-Phenyl-pyridin-3-yl)carbonyl]-10,11-dihydro-5H-pyrrolo[2,1-c][1,4]benzodiazepine-3-carboxylic acid bis-(2-hydroxy-ethyl)-amide A solution of 6-phenyl-nicotinyl chloride (6 mmol) [prepared by the method of Ogawa (Ogawa et al WO 9534540)] in dichloromethane (20 mL) was added dropwise to a cold (0° C.) solution of 10,11-dihydro-5H-pyrrolo[2,1-c][1,4]benzodiazepine-3-carboxylic acid bis-(2-hydroxy-ethyl)-amide of Step C (5 mmol) and N,N-diisopropylethyl amine (6 mmol) in dichloromethane (100 mL). The solution was stirred at 0° C. for 2 hours and then allowed to warm to room temperature overnight. The solution was washed with pH 6 buffer, and brine, dried over anhydrous sodium sulfate, filtered and concentrated. The residue was chromatographed on silica gel using 5% methanol in chloroform containing 0.5% ammonium hydroxide, to provide the title compound.

EXAMPLE 35

10-{[6-(Naphthalen-1-yl)-pyridin-3-yl]-carbonyl}-N-methyl-N-[(2S, 3R, 4R, 5R)-2,3,4,5,6-pentahydroxy-hexyl]-10,11-dihydro-5H-pyrrolo[2,1-c][1,4]benzodiazepine-3-carboxamide Step A. (6-Chloro-pyridin-3-yl)-[10,11-dihydro-5H-pyrrolo[2,1-c][1,4]benzodiazepin-10-yl]methanone A solution of 10,11-dihydro-5H-pyrrolo[2,1-c][1,4]benzodiazepine (100 mmol) and N,N'-diisopropylethyl amine (130 mmol) in dichloromethane (500 mL) was cooled to 0° C. 6-Chloronicotinoyl chloride (130 mmol) was added dropwise under nitrogen. The solution was stirred for one hour as it returned to room temperature. The reaction mixture was filtered through a sica gel pad, washed with 0.5 N sodium hydroxide and water, dried over anhydrous magnesium sulfate. The solution was again filtered through a silica gel pad and evaporated to dryness in vacuo. The residual oil crystallized from diethyl ether to provide the title compound as a colorless crystalline solid, m.p. 165–167° C.

$^1$H NMR (400 MHz, DMSO-$d_6$): δ 5.35 (br, 4H), 5.91 (t, 1H), 5.97 (s, 1H), 6.83 (t, 1H), 7.0 (br d, 1H), 7.18 (t, 1H), 7.19 (t, 1H), 7.39 (d, 1H), 7.46 (dd, 1H), 7.71 (d, 1H), 8.26 (s, 1H).

MS [EI, m/z]: 323 $[M]^+$.

Anal. Calcd. for $C_{18}H_{14}ClN_3O$: C 66.77, H 4.36, N 12.98. Found: C 65.91, H 4.18, N 12.69.

Step B. [6-(Naphthalen-1-yl)-pyridin-3-yl]-[10,11-dihydro-5H-pyrrolo[2,1-c][1,4]benzodiazepin-10-yl]methanone A suspension of (6-chloro-pyridin-3-yl)-[10,11-dihydro-5H-pyrrolo{2,1-c][1,4]benzodiazepin-10-yl]methanone of Step A (0.645 g, 1.9 mmol) and naphthalene boronic acid (0.372 g, 2.1 mmol) in a mixture of toluene (1.2 mL), ethanol (2 mL) and 1M aqueous sodium carbonate (0.4 mL) was sparged with nitrogen for 10 minutes. To this was added palladium(I) acetate (0.026 g, 0.1 mmol). The mixture was heated at reflux under a static pressure of nitrogen for 48 hrs. The reaction was diluted with ethyl acetate and water. The organic layer was washed with saturated aqueous sodium bicarbonate then water. The sample was dried over anhydrous magnesium sulfate, filtered and concentrated in vacuo to a brown oil. Flash chromatography of the residue on silica gel eluting with 20–50% ethyl acetate in hexane, yielded 0.180 g of a solid which was recrystallized from chloroform to provide the title compound as off white crystals, m.p. 155–158° C.

$^1$H NMR (400 MHz, DMSO-$d_6$): δ 5.40 (br, 4H), 5.93 (m, 1H), 5.99 (s, 1H), 6.84 (s, 1H), 7.08 (brd, 1H), 7.16 (t, 1H), 7.23 (t, 1H), 7.52 (m, 6H), 7.84 (d, 2H), 7.98 (dd, 2H), 8.55 (s, 1H).

MS [(+)ESI, m/z]: 416 $[M+H]^+$.

Anal. Calcd. for $C_{28}H_{21}N_3O+0.5H_2O$: C 79.22, H 5.23, N 9.90., Found: C 79.08, H 4.94, N 9.73.

Step C. 10-{[6-(Naphthalen-1-yl)-pyridin-3-yl]carbonyl}-10,11-dihydro-5H-pyrrolo[1,2-c][1.4]benzodiazepine-3-carboxylic acid Prepared from [6-(naphthalen-1-yl)-pyridin-3-yl][10,11-dihydro-5H-pyrrolo[2,1-c][1,4]benzodiazepin-10-yl] methanone of Step C by treatment with trichloroacetyl chloride, followed by basic hydrolysis of the intermediate trichloroacetate ester in the manner of Example 1, Step F.

Step D. 10-{[6-(Naphthalen-1-yl)-pyridin-3-yl]-carbonyl}-N-methyl-N-[(2S, 3R, 4R, 5R)-2,3,4,5,6-pentahydroxy-hexyl]-10,11-dihydro-5H-pyrrolo[2,1-c][1,4]benzodiazepine-3-carboxamide The title compound was prepared by the coupling of 10-{[6-(naphthalen-1-yl)-pyridin-3-yl]carbonyl}-10,11-dihydro-5H-pyrrolo[1,2-c][1.4]benzodiazepine-3-carboxylic acid of Step C, and N-methyl-D-glucamine (1.25 equiv) in the manner of Example 4.

EXAMPLE 36

{(2S)-1-[(10-{[2-Methoxy-2(trifluoromethyl)[1,1'-biphenyl]-4-yl]carbonyl}-10,11-dihydro-5H-pyrrolo[2,1-c][1,4]benzodiazepin-3-yl)carbonyl]pyrrolidin-2-yl}-methanol The title compound was prepared from 10-{[2-methoxy-2'-trifluoromethyl-[1,1'-biphenyl]-4-yl]carbonyl}-10,11-dihydro-5H-pyrrolo[2,1-c][1,4]benzodiazepine-3-carboxylic acid of Example 21, Step E (0.225 g, 0.48 mmol) and (S)-(+)-2-pyrrolidinemethanol (0.070 g, 0.7 mmol) in the manner of Example 21, Step F, as an amorphous solid (0.112 g), m.p. 203–205° C. (dec).

$^1$H NMR (400 MHz, DMSO-$d_6$): δ 1.89–2.03 (m, 4H), 3.25 (s, 3H), 3.56 (m, 2H), 4.35 (s, 2H), 5.43 (m, 2H), 5.56 (br, 2H), 6.06 (s, 1H), 6.41 (s, 1H), 6.85–6.97 (m, 4H), 7.04 (t, 1H), 7.18 (t, 1H), 7.20 (d, 1H), 7.23 (d, 1H), 7.42 (m, 2H), 7.56 (t, 1H), 7.62 (t, 1H), 7.74 (d, 1H).

MS (El, m/z): 590 $[M]^+$.

Anal. Calcd. for $C_{33}H_{30}F_3N_3O_4$: C 67.22, H 5.13, N 7.13. Found: C 66.84, H 5.49, N 6.81

EXAMPLE 37

7,8-Dimethoxy-10-[(2'-methoxy-2-methyl-[1,1'-biphenyl]-4-yl)carbonyl]-10,11-dihydro-5H-pyrrolo[2,1-c][1,4]benzodiazepine-3-carboxylic acid methyl-[(2S, 3R, 4R, 5R)-2,3,4,5,6-pentahydroxy-hexyl)-amide Step A. 7,8-Dimethoxy-(2'-methoxy-2-methyl-[1,1'-biphenyl]-4-yl)carbonyl]-10,11-dihydro-5H-pyrrolo[2,1-c][1,4]benzodiazepine The title compound was obtained as a white solid, m.p. 160–161° C., by reacting 7,8-dimethoxy-(10,11-dihydro-5H-pyrrolo[2,1-c][1,4]benzodiazepin-10-yl)-(4-bromo-3-methyl-phenyl)-methanone of Example 18, Step C with 2-methoxyphenyl boronic acid in the manner of Example 18, Step D.

$^1$H NMR (400 MHz, DMSO-$d_6$): δ 1.95 (s, 3H), 3.45 (s, 3H), 3.65 (s, 3H), 3.75 (s, 3H), 5.10 (br, 2H), 5.20 (s, 2H), 5.90 (t, 1H), 5.95 (s, 1H), 6.60 (s, 1H), 6.75 (t 1H), 6.90 (s, 1H), 6.95–7.10 (m, 5H), 7.25 (s, 1H), 7.35 (m, 1H).

MS [APCI, m/z]: 469 $[M+H]^+$.

Anal. Calcd. for $C_{29}H_{28}N_2O_4$: C 74.34, H 6.02, N 5.98. Found: C 74.01, H 6.10, N 5.94

Step B. 7,8-Dimethoxy-10-[(2'-methoxy-2-methyl-[1,1'-biphenyl]-4-yl)carbonyl]-10,11-dihydro-5H-pyrrolo[2,1-c][1,4]benzodiazepine-3-carboxylic Acid methyl-[(2S,3R,4R,5R)-2,3,4,5,6-pentahydroxy-hexyl)-amide Reaction of 7,8-dimethoxy-(2'-methoxy-2-methyl-[1,1'-biphenyl]-4-yl)carbonyl]-10,11-dihydro-5H-pyrrolo[2,1-c][1,4]benzodiazepine of Step A with diphosgene and N-methyl-D-glucamine in the manner of Example 18, Step E provided the title compound as a pale green solid, m.p. 110–120° C.

$^1$H NMR (400 MHz, DMSO-$d_6$): δ 1.95 (s, 3H), 3.05 (s, 3H), 3.30–3.60 (m, 10H), 3.65 (s, 3H), 3.70 (s, 3H), 3.90 (s,

1H), 4.30 (t, 2H), 4.40 (s, 1H), 4.50 (s, 1H), 4.90 (s, 1H), 5.10 (br, 2H), 5,25 (dd, 2H), 6.00 (s, 1H), 6.30 (s, 1H), 6.50 (s, 1H), 6.90–7.10 (m, 6H), 7.25 (s, 1H), 7.35 (s, 1H).

MS [APCI, m/z]: 690 $[M+H]]^+$.

Anal. Calcd. for $C_{37}H_{43}N_3O_{10}$+$0.5H_2O$: C 63.60, H 6.35, N 6.01. Found: C 63.63, H 6.37, N 5.89.

EXAMPLE 38

9-[(2-Methyl-2'-trifluoromethyl-[1,1'-biphenyl]-4-yl) carbonyl]-9,10-dihydro-4H-3a, 5,9-triaza-benzo[f]azulene-3-carboxylix acid (3-hydroxy-propyl)-amide Step A. 2-Chloromethyl-pyridine-3-carboxylic acid methyl ester A solution of methyl 2-methylnicotinate (20.0 g, 0.132 mol) and trichloroisocyanuric acid (46.0 g, 0.198 mol) in dichloromethane (100 mL) was stirred at room temperature overnight. The reaction mixture was then washed with saturated aqueous sodium carbonate and saturated aqueous sodium chloride, dried over anhydrous magnesium sulfate, filtered, and the solvent evaporated in vacuo to provide the title compound as a yellow liquid (11.2 g), which is used as such in the next step.

Step B. 2-(2-Formyl-pyrrol-1-ylmethyl)-pyridine-3-carboxylic acid methyl ester

To a suspension of sodium hydride (5.8 g, 0.12 mol) in dry N,N-dimethyl formamide (25 mL) was added slowly under nitrogen a solution of pyrrole 2-carboxaldehyde (10.5 g, 0.11 mol) in N,N-dimethylformamide (10 mL). The reaction mixture was stirred at room temperature for 30 minutes, then cooled to 5° C. and 2-chloromethyl-pyridine-3-carboxylic acid methyl ester of Step A added slowly while the temperature was being maintained at or below 20° C. After the addition was complete the reaction was stirred at room temperature for 30 minutes. The mixture was evaporated to dryness, and the residue was dissolved in ethyl acetate (250 mL). This solution was washed with water and dried over anhydrous magnesium sulfate. The solvent was then removed in vacuo leaving a dark crystalline solid (23.4 g), which was purified by chromatography on silica gel eluting with a gradient of ethyl acetate/petroleum ether to provide the title compound as a tan crystalline solid (13.75 g), m.p. 91–93° C.

Step C. 1-(3-Phenylacetyl-pyridin-2-ylmethyl)-1H-pyrrole-2-carbaldehyde

To a stirred solution of 2-(2-formyl-pyrrol-1-ylmethyl)-pyridine-3-carboxylic acid methyl ester of Step B (13.65 g, 55.9 mmol) in methanol (50 mL) was added sodium hydroxide (2.2 g, 55.9 mmol.). The reaction mixture was refluxed under nitrogen for 2 hours, and then the solvent was removed in vacuo. A portion of the residual yellow solid.(5 g) was suspended in a mixture of benzyl alcohol (20 mL) and benzene (30 mL). Diphenylphosphoryl azide (6.54 g, 1.2 equiv.) was added, and the reaction was slowly heated to reflux. After refluxing for 1 hour, the mixture was cooled and washed with water, dried over anhydrous magnesium sulfate, filtered and evaporated to dryness to provide the title compound as a tan crystalline solid (4.4 g), m.p. 109–111° C.

Step D. 9,10-Dihydro-4H-3a,5,9-triaza-benzo[f]azulene

A stirred mixture of 1-(3-phenylacetyl-pyridin-2-ylmethyl)-1H-pyrrole-2-carbaldehyde of Step C (1.0 g), in ethyl acetate (10 mL) containing 10% palladium on charcoal (10 mg.), magnesium sulfate (0.010 g) and 5 drops of acetic acid was hydrogenated at atmospheric pressure until hydrogen uptake ceased. The reaction mixture was then filtered through Celite and the solvent removed in vacuo. The crude product (yellow crystalline solid, 0.530 g) was purified by chromatography on silica gel eluting with a gradient of ethyl acetate in petroleum ether to provide the title product as a yellow crystalline solid, m.p. 171–172° C.

Step E. (4-Bromo-3-methyl-phenyl)-(4H,10H-3a,5,9-triaza-benzo[f]azulen-9-yl)-methanone To a stirred solution of 9,10-dihydro-4H-3a,5,9-triaza-benzo[f]azulene of Step D (1.0 g) in dichloromethane (10 mL) was added 3-methyl-4-bromobenzoyl chloride (1.39 g) and triethylamine (1.1 mL). After stirring for 2.5 hours, the reaction mixture was washed with water, dried over anhydrous magnesium sulfate, filtered and the solvent removed in vacuo to provide the title product as a tan crystalline solid (2.3 g), which was used without further purification.

Step F. (2-Methyl-2'-trifluoromethyl-[1,1'-biphenyl]-4-yl)-(4H,10H-3a,5,9-triaza-[f]azulen-9-yl)-methanone A stirred mixture of (4-bromo-3-methyl-phenyl)-(4H,1 OH-3a,5,9-triaza-benzo[f]azulen-9-yl)-methanone of Step E (1.0 g), 2-trifluoromethylboronic acid (1.49 g, 3.0 equiv.), potassium phosphate (2.2 g) and a catalytic amount (0.050 g) of tetrakis(triphenylphosphine) palladium (0) in dioxane (10 mL) was refluxed for 2 hours. The solvent was then removed in vacuo and the residue dissolved in dichloromethane. The solution was then washed with water, dried over anhydrous magnesium sulfate, filtered and evaporated to dryness. The residue was then chromatographed on silica gel eluting with 5% ethyl acetate in dichloromethane to yield a colorless gum which crystallized upon addition of a little diethyl ether to provide the title compound as a cream-colored crystalline solid (0.500 g), m.p. 153–155° C.

$^1$H NMR (DMSO-$d_6$, 400 MHz): δ 1.85 (s, 3H), 5.10 (s, 2H), 5.40 (s, 2H), 5.90 (t, 1H), 6.00 (s, 1H), 6.90 (t, 1H), 6.94 (d, 1H), 7.03 (d, 1H), 7.12 (dd, 1H), 7.23 (d, 1H), 7.28 (s, 1H), 7.37 (d, 1H), 7.58 (t, 1H), 7.68 (t, 1H), 7.80 (d, 1H), 8.27 (d, 1H)

MS [(+)ESI, m/z]: 448 $[M+H]^+$.

Anal. Calcd. for $C_{26}H_2OF_3N_3O$: C 69.79, H 4.51, N 9.39. Found: C 69.91, H 4.30, N 9.26)

Step G. 2,2,2-Trichloro-1-{[9-(2-methyl-2'-trifluoromethyl-[1,1'-biphenyl]-4-yl)carbonyl]-9,10-dihydro-4H-3a,5,9-triaza-benzo[f]azulen-3-yl}-ethanone To a solution of (2-methyl-2'-trifluoromethyl-[1,1'-biphenyl]-4-yl)-(4H,10H-3a,5,9-triaza-benzo[f]azulen-9-yl)-methanone of Step F in dichloromethane was added trichloroacetyl chloride (1.1 equiv.) and triethylamine (1.5 equiv,) After stirring overnight at room temperature, the reaction was washed with water, dried over anhydrous magnesium sulfate, and evaporated to dryness to provide the crude title compound which was used as such in the next step.

Step H. 9-[(2-Methyl-2'-trifluoromethyl-[1,1'-biphenyl]-4yl)carbonyl]-9,10-dihydro-3a, 5,9-triaza-benzo[f]azulen-3-carboxylic acid To a solution of 2,2,2-trichloro-1-{[9-(2-methyl-2'-trifluoromethyl-[1,1'-biphenyl]-4yl)carbonyl]-9,10-dihydro-4H-3a,5,9-triaza-benzo[f]azulen-3-yl}-ethanone of Step G in acetone was added 2.5 N sodium hydroxide (1.0 equiv.). After stirring overnight, the solvent was removed in vacuo leaving the crude sodium salt of the carboxylic acid. This was dissolved in anhydrous ethanol and treated with 2 N hydrochloric acid (1.0 equiv.). The solvent was removed in vacuo, the residue redissolved in anhydrous ethanol and the solvent again removed in vacuo. The crude title compound was then dried in vacuo over phosphorus pentoxide.

Step I. 9-[(2-Methyl-2'-trifluoromethyl-[1,1'-biphenyl]-4-yl) carbonyl]-9,10-dihydro-4H-3a,5,9-triaza-benzo[f]azulene-3-carboxylic Acid (3-hydroxy-propyl)-amide To a solution of the 9-[(2-methyl-2'-trifluoromethyl-[1,1'-biphenyl]-4yl)carbonyl]-9,10-dihydro-3a,5,9-triaza-benzo

[f]azulen-3-carboxylic acid (3.38 mmol) of Step H in N,N-dimethylformamide (20 mL) was added 1-hydroxybenzotriazole (1.1 equiv.) and [3-(dimethylamino) propyl]-3-ethylcarbodiimide hydrochloride (1.2 equiv. ), followed by 3-aminopropanol (1.2 equiv.) and N,N-diisopropylethyl amine (1.5 equiv.). The reaction mixture was stirred overnight, then diluted with ethyl acetate and washed with water and saturated aqueous sodium bicarbonate. The organic phase was dried over anhydrous sodium sulfate, filtered and concentrated in vacuo. Purification of the residue was effected by chromatography on silica gel eluting with a gradient of methanol in dichloromethane to provide the title compound as a white foam.

The following examples were prepared according to the general procedures described below.

General Procedure A

Step A. An appropriately substituted haloaryl carboxylic acid (1.1 mol) was converted to the acid chloride by using oxalyl chloride (1.5 mmol) and a catalytic amount of N,N-dimethylformamide in dichloromethane. Upon consumption of the acid as determined by HPLC analysis, all volatiles were removed in vacuo. The resulting residue was dissolved in dichloromethane and added dropwise to a stirred and cooled (0° C.) solution of an appropriately substituted 5H-pyrrolo[2,1-c][1,4]benzodiazepine (1 mmol) and N,N-diisopropylethyl amine (1.2 mmol) in dichloromethane. After 1–16 hours, the mixture was diluted with dichloromethane and washed with 10% aqueous sodium bicarbonate. The combined organic extracts were dried over anhydrous sodium sulfate, filtered and concentrated.

Step B. To the residue was added an appropriately substituted boronic acid (1.2 mmol), potassium carbonate (2.5 mmol), tetrabutylammonium bromide (1 mmol), palladium (II) acetate (3% mole) and water/acetonitrile (1:1, 2 mL). The contents were heated to 70° C. for 1.5 hours, then ethyl acetate was added and the organic phase washed with water. The solution was filtered through a small plug of Celite and concentrated to dryness.

Step C. The residue was dissolved in dichloromethane and N,N-diisopropylethyl amine (2 mmol) was added. The flask was purged with nitrogen and trichloroacetyl chloride was added dropwise to the stirred reaction mixture. After 16 hours, the reaction was quenched by adding aqueous potassium carbonate (100 g/300 mL) and the organic phase removed. The aqueous layer was extracted with additional dichloromethane and the combined extracts dried over anhydrous sodium sulfate, filtered and concentrated .

Step D. The crude product from Step C was dissolved in tetrahydrofuran (1 mL) and 2N sodium hydroxide (1.5 mL) was added. The mixture was heated (70° C.) for 1.5 hours, 2N hydrochloric acid was added and the product extracted with ethyl acetate. The organic phase was dried, filtered and concentrated. The residue was purified by column chromatography using a gradient of ethyl acetate in hexane contaning 1% glacial acetic acid as the eluant.

Step E. To a stirred solution of a carboxylic acid of Step D above (1.85 mmol) in anhydrous tetrahydrofuran (14 mL) was added 1,1'-carbonyl diimidazole in one portion. The mixture was stirred at room temperature (6–8 hours). The progress of the reaction was monitored by HPLC and when the starting carboxylic acid was consumed, the mixture was worked up to provide the intermediate imidazolide.

Step F. An aliquot of a tetrahydrofuran solution (400 $\mu$L, 0.05 mmole) containing the imidazolide of Step E (0.05 mmol) was treated with a 0.25 M solution of an appropriate amine (0.1 mmol). The mixture was heated at 60° C. and the progress of the reaction followed by HPLC. The solvent was removed and the residue dissolved in dichloromethane (1 mL). The organic phase was washed with brine-water (1:1, v/v, 1 mL) and the aqueous layer extracted with additional dichloromethane. The combined extracts were dried and evaporated to dryness and the residue was purified by flash chromatography on silica gel. The column (prepacked in 2.5% methanol in dichloromethane contaning 1% triethylamine) was eluted with a solvent gradient from 2.5 to 5% methanol in dichloromethane, to provide desired title compound. The desired title compounds were either obtained as crystalline solids by exposure to diethyl ether or were further converted into their salts by any of the following procedures.

Step G. Compounds prepared according to Step E that dissolved in diethyl ether were treated with a stoichiometric amount of 1 N hydrochloric acid in diethyl ether whereby the hydrochloride salts precipitated out as white solids. Compounds that did not conform to the above category, were dissolved in the minimal amount of tetrahydrofuran, then diluted with diethyl ether. The hydrochloride salts were formed upon addition of 1 N hydrochloric acid in diethyl ether with stirring. Compounds that did not immediately precipitate out of solution were stirred for 12–16 hours whereupon a white solid precipitated out.

General Procedure B

To a stirred solution of an appropriately substituted carboxylic acid of General Procedure A, Step D (2 mmol), 1-ethyl-3-(3-dimethylamino-propyl) carbodiimide (0.229 g, 2.2 mmol) and a catalytic amount of 4-(dimethylamino) pyridine in dichloromethane (6 mL) was added the appropriately substituted amine (2.2 mmol) in dichloromethane (2 mL). The reaction was allowed to stir at room temperature for 16 hours, then diluted with dichloromethane. The organic layer was washed with water, and saturated aqueous sodium bicarbonate, dried over anhydrous sodium sulfate and evaporated to dryness. The residue was purified by flash chromatography on silica gel (prepacked in dichloromethane containing 2.5% methanol and 1% triethylamine and eluted with a solvent gradient of 2.5 to 5% methanol in dichloromethane) to provide the desired title compound.

General Procedure C

Triphosgene (742 mg, 2.5 mmol) was added to a stirred solution of a carboxylic acid of General Procedure A, Step D (5.0 mmol) in dichloromethane (10 mL). The clear solution was allowed to stir at room temperature (14 hours) after which time the solution turned red. To the reaction mixture was added a solution of the required amine (10.0 mmol) and N,N-diisopropylethyl amine (10.0 mmol) in dichloromethane (5 mL). The mixture was diluted with dichloromethane and washed with water and brine. The organic phase was dried, filtered and concentrated to afford a residue which was purified by flash chromatography on silica gel. The column (prepacked in 2.5% methanol in dichloromethane contaning 1% triethylamine) was eluted with a solvent gradient from 2.5 to 5% methanol in dichloromethane, to provide the title compound.

General Procedure D

A stirred solution of a carboxylic acid of General Procedure A, Step D (3.54 mmol) and the appropriately substituted amine (3.72 mmol) in N,N-dimethylformamide (10 mL) was cooled to 0° C. N,N-diisopropylethyl amine (3.89 mmol) was added and the mixture stirred for five minutes. O-(1-Benzotriazolyl)-N,N,N',N'-tetramethyluronium hexafluorophosphate (HBTU) (1.42 g, 3.72 mmol) was added to the mixture in one portion. HPLC analysis revealed that the reaction was complete within five minutes. The solvent was removed at reduced pressure. The residue was diluted with water and extracted with ethyl acetate. The combined extracts were dried and concentrated to dryness. The residue was purified by flash chromatography on silica gel (prepacked in ethyl acetate containing 2% triethylamine and eluted with 100% ethyl acetate) to provide the title compound.

General Procedure E

To a 0.25 M solution of a carboxylic acid of General Procedure A, Step D (200 μL) in N,N-dimethylformamide was added sequentially a 0.5 M solution of N,N-diisopropylethyl amine (200 1L) in N,N-dimethylformamide, and a 0.25 M solution of O-(7-aza-1-benzotriazolyl)-N,N,N',N'-tetramethyluronium hexafluorophosphate (HATU) (210 μL) in N,N-dimethylformamide. The mixture was stirred vigorously at room temperature and then a 0.25 M solution of the appropriately substituted amine (200 μL) in N,N-dimethylformamide was added. Stirring was continued for 24 hours at room temperature, then the mixture was diluted-with ethyl acetate, and washed with 1:1 water/brine. The organic layer was dried and concentrated to dryness. The residue was purified by flash chromatography on silica gel (prepacked in ethyl acetate containing 2% triethylamine and eluted with 100% ethyl acetate) to provide the title compound.

General Procedure F

Step A. To a solution of an appropriately substituted anilino carboxylic acid in methanol was added thionyl chloride. The mixture was heated for 16 hours. The volatiles were removed under reduced pressure and the hydrochloride salt of the carboxylic acid methyl ester was recovered after trituration with methanol/diethyl ether. The solid was dissolved in concentrate hydrochloric acid and cooled. An aqueous solution of sodium nitrite was added and the mixture was stirred at 0° C. for one hour. An aqueous solution of $KI/I_2$ was prepared and added to the cooled mixture so that the reaction temperature did not exceed 0° C. After 1–2 hours the reaction was complete as evidenced by TLC/HPLC analysis. The product was recovered by extraction with ethyl acetate. The combined extracts were dried, filtered and concentrated to afford the desired substituted aryl iodide which could be further purified by recrystallization.

Step B. To a solution of an appropriately substituted aryl halide methyl ester of Step A (2 mmol) and an appropriately substituted boronic acid (2 mmol) in 20% aqueous acetone was added cesium carbonate (3 mmol) followed by palladium(II) acetate (60 μmol). The mixture was heated (70° C.) with stirring for 8–16 hours. The reaction was concentrated to remove the acetone after TLC/HPLC analysis indicated the reaction was complete. The aqueous phase was extracted with ethyl acetate and the combined extracts were filtered through a pad of Celite. The filtrate was washed with 5% aqueous sodium bicarbonate and brine, dried over anhydrous sodium sulfate, filtered and evaporated to dryness. The residue was purified by flash chromatography on silica gel.

Step C. The product from Step B was dissolved in tetrahydrofuran (1 mL) and 2N sodium hydroxide (1.5 mL) was added. The mixture was heated (70° C.) for 1.5 hours, 2N hydrochloric acid was added and the product extracted with ethyl acetate. The organic phase was dried, filtered and concentrated. The residue was purified by column chromatography using ethyl acetate in hexane contaning 1% glacial acetic acid as the eluant.

Step D. To a suspension of the carboxylic acid of Step C (60 μmol) in dichloromethane (100 μL) was added a 0.45 M solution of oxalyl chloride (200 μL) in dichloromethane followed by dichloromethane (100 μL) containing a catalytic amount of N,N-dimethylformamide. The mixture was allowed to sit at room temperature for 16 hours, then the volatiles were removed in vacuo to afford the crude acid chloride. A solution of the acid chloride in tetrahydrofuran (0.3 M, 200 μL) was utilized to acylate a solution (0.3 M, 200 μL) of an appropriately substituted 5H-pyrrolo[2,1-c][1,4]benzodiazepine in tetrahydrofuran according to the General Procedure A, Step A.

General Procedure G

A mixture of an appropriately substituted aryl bromide methyl ester (or an aryl iodode methyl ester of General Procedure F, Step A) (8.3 mmol), an appropriately substituted boronic acid (9.1 mmol), potassium carbonate (20.8 mmol), tetrabutylammonium bromide (or iodide) (8.3 mmol), palladium(II) acetate and water (8–9 mL) was stirred with heating (70° C.) for 1.5 hours, whereupon the reaction was deemed complete by HPLC analysis. The oily upper layer was extracted with ethyl acetate, the extracts washed with brine, dried and concentrated to dryness. The residue was filtered through a column of silica gel to provide the desired coupled product of General Procedure F, Step B.

General Procedure H

The coupling of an appropriately substituted aryl bromide methyl ester (or an aryl iodide methyl ester of General Procedure F, Step A) (8.3 mmol) to an appropriately substituted pyridyl borane was carried out using potassium hydroxide as the base, in the presence of tetrabutylammonium bromide (or iodide) and a tetrakis(triphenylphoshine) palladium(0) catalyst essentially according to the published procedure of M. Ishikura, *Synthesis*, 936–938 (1994), to provide the desired coupled product of General Procedure F, Step B.

General Procedure I

The coupling of an appropriately substituted aryl bromide methyl ester (or an iodide methyl ester of General Procedure F, Step A) (8.3 mmol) to an appropriately substituted boronic acid was carried out essentially according to General Procedure F, Step B except that the solvent was acetonitrile.

General Procedure J

The desired substituted aryl iodide of General Procedure F, Step A was prepared by reaction of an appropriately substituted amino carboxylic acid in concentrated hydrochloric acid at 0° C. with an aqueous solution of sodium nitrite followed by the addition of an aqueous solution of potassium/iodine at 0° C., followed by esterification of the resulting iodo aryl carboxylic acid with methanolic hydrochloric acid.

General Procedure K

The acylation of an activated appropriately substituted arylpyridine carboxylic acid of Procedure H was carried out by dissolving the acid (0.06 mmol) in a solution of oxalyl chloride in dichloromethane (12 mg/200 μL) followed by a catalytic amount of N,N-dimethylformamide in dichloromethane (100 μL). After stirring at room temperature for 16 hours, the volatiles were removed and tetrahydrofuran added, followed by the addition of a solution of the appropriately substituted 5H-pyrrolo[2,1-c][1,4]benzodiazepine and N,N-diisopropylethyl amine (1:2 molar ratio) in tetrahydrofuran. After stirring for 20 hours, the reaction was worked up essentially as described in General Procedure A, Step A.

EXAMPLE 39

{10-[(6-Chloro-3-methoxy-2'-methyl[1,1'-biphenyl]-4-yl) carbonyl]-10,11-dihydro-5H-pyrrolo[2,1-c][1,4] benzodiazepin-3-yl}[4-(2-hydroxyethyl)-1-piperazinyl] methanone HRMS [(+)ESI, m/z]: 599.24233 $[M+H]^+$. Calcd. for $C_{34}H_{36}ClN_4O_4$: 599.24196

EXAMPLE 40

[4-(2-Hydroxyethyl)-1-piperazinyl]{10-[(2'-methoxy-2-methyl[1,1'-biphenyl]-4yl)carbonyl]-10,11-dihydro-5H-pyrrolo[2,1-c][1,4]benzodiazepin-3-yl}methanone HRMS [(+)ESI, m/z]: 565.28069 $[M+H]^+$. Calcd. for $C_{34}H_{37}N_4O_4$. 565.28094

EXAMPLE 41

[4-(2-Hydroxyethyl)-1-piperazinyl]{10-[3-methoxy-4-(1-naphthyl)benzoyl]-10,11-dihydro-5H-pyrrolo[2,1-c][1,4] benzodiazepin-3-yl}methanone HRMS [(+)ESI, m/z]: 601.27922 $[M+H]^+$. Calcd. for $C_{37}H_{37}N_4O_4$ 601.28094

EXAMPLE 42

[4-(2-Hydroxyethyl)-1-piperazinyl]{10-[(2-methoxy-2'-methyl[1,1'-biphenyl]-4yl)carbonyl]-10,11-dihydro-5H-pyrrolo[2,1-c][1,4]benzodiazepin-3-yl}methanone HRMS [(+)ESI, m/z]: 565.28120 $[M+H]^+$. Calcd. for $C_{34}H_{37}N_4O_4$ 565.28094

EXAMPLE 43

{10-[(2,2'-Dimethoxy[1,1'-biphenyl]-4-yl)carbonyl]-10,11-dihydro-5H-pyrrolo[2,1-c][1,4]benzodiazepin-3-yl}[4-(2-hydroxyethyl)-1-piperazinyl]methanone HRMS [(+)ESI, m/z]: 581.27378 $[M+H]^+$. Calcd. for $C_{34}H_{37}N_4O_5$ 581.27585

EXAMPLE 44

[4-(2-Hydroxyethyl)-1-piperazinyl]{10-[(3'-methoxy-2-methyl[1,1'-biphenyl]-4yl)carbonyl]-10,11-dihydro-5H-pyrrolo[2,1-c][1,4]benzodiazepin-3-yl}methanone HRMS [(+)ESI, m/z]: 565.27969 $[M+H]^+$. Calcd. for $C_{34}H_{37}N_4O_4$ 565.28094

EXAMPLE 45

[4-(2-Hydroxyethyl)-1-piperazinyl]{10-[(2'-methyl[1,1'-biphenyl]-4-yl)carbonyl]-10,11-dihydro-5H-pyrrolo[2,1-c][1,4]benzodiazepin-3-yl}methanone HRMS [(+)ESI, m/z]: 535.26943 $[M+H]^+$. Calcd. for $C_{33}H_{35}N_4O_3$ 535.27037

EXAMPLE 46

{10-[(2,2'-Dimethyl[1,1'-biphenyl]-4-yl)carbonyl]-10,11-dihydro-5H-pyrrolo[2,1-c][1,4]benzodiazepin-3-yl}[4-(2-hydroxyethyl)-1-piperazinyl]methanone HRMS [(+)ESI, m/z]: 549.28658 $[M+H]^+$. Calcd. for $C_{34}H_{37}N_4O_3$: 549.28602

EXAMPLE 47

[4-(2-Hydroxyethyl)-1-piperazinyl]{10-[(2'-methoxy[1,1'-biphenyl]-4-yl)carbonyl]-10,11-dihydro-5H-pyrrolo[2,1-c][1,4]benzodiazepin-3-yl}methanone HRMS [(+)ESI, m/z]: 551.26476 $[M+H]^+$. Calcd. for $C_{33}H_{35}N_4O_4$ 551.26529

EXAMPLE 48

[4-(2-Hydroxyethyl)-1-piperazinyl](10-{[2-methyl-2'-(trifluoromethyl)[1,1'-biphenyl]-4-yl)carbonyl}-10,11-dihydro-5H-pyrrolo[2,1-c][1,4]benzodiazepin-3-yl) methanone HRMS [(+)ESI, m/z]: 603.25707 $[M+H]^+$. Calcd. for $C_{34}H_{34}F_3N_4O_3$ 603.2577

EXAMPLE 49

{10-[(6-Chloro-3,3'-dimethoxy[1,1'-biphenyl]-4-yl) carbonyl]-10,11-dihydro-5H-pyrrolo[2,1-c][1,4] benzodiazepin-3-yl}[4-(2-hydroxyethyl)-1-piperazinyl] methanone HRMS [(+)ESI, m/z]: 615.23646 $[M+H]^+$. Calcd. for $C_{34}H_{36}ClN_4O_5$ 615.23688

EXAMPLE 50

{10-[(2,3'-Dimethoxy[1,1'-biphenyl]-4-yl)carbonyl]-10,11-dihydro-5H-pyrrolo[2,1-c][1,4]benzodiazepin-3-yl}[4-(2-hydroxyethyl)-1-piperazinyl]methanone HRMS [(+)ESI, m/z]: 581.27577 $[M+H]^+$. Calcd. for $C_{34}H_{37}N_4O_5$ 581.27585

EXAMPLE 51

10-(3-Methoxy-4-pyridin-3-yl-benzoyl)-10,11-dihydro-5H-pyrrolo[1,2-c][1,4]benzodiazepin-3-carboxylic acid (2,3-dihydroxy-propyl)-methyl-amide MS [(+)ESI, m/z]: 527 $[M+H]^+$. Calcd. for $C_{30}H_{31}N_4O_5$ 527.23.

General Procedure L

Step A. To a stirred cooled (0° C.) solution of an appropriately substituted 10-(4-amino)benzoyl-10,11-dihydro-5H-pyrrolo[2,1-c][1,4]benzodiazepine (10 mmol) in dichloromethane (20 mL) was added N,N-diisopropylethyl amine (2.09 mL, 12 mmol) followed by the addition of 9-fluorenylmethylchloroformate (2.85 g, 11 mmol) in one portion. The reaction was allowed to warm to room temperature. TLC analysis was used to monitor the progress of the reaction and after 8 hours, indicated that a single product was formed. The reaction mixture was diluted with dichloromethane and washed with water and brine. The organic phase was dried over anhydrous sodium sulfate, filtered and concentrated. The resulting residue was purified by flash column chromatography (Biotage Flash 40S, 10–20% EtOAc-hexanes) to provide the desired appropriately substituted 4-(fluorenylmethoxycarbonyl)-10,1-dihydro-5H-pyrrolo[2,1-c][1,4]benzodiazepine.

Step B. Trichloroacetyl chloride (3.35 mL, 30 mmol) was added to a solution of an appropriately substituted 4-(fluorenylmethoxycarbonyl)-10,1-dihydro-5H-pyrrolo[2,1-c][1,4]benzodiazepine of Step A (10 mmol) and N,N-didisopropylethyl amine (3.48 mL, 20 mmol) in dichloromethane, and the solution was stirred at ambient temperature for 2 hours. An aqueous solution of sodium bicarbonate (0.5 M) was added to the mixture and the organic layer was separated, dried over anhydrous sodium sulfate, filtered and concentrated. The residue was dissolved in a solution of piperidine in N,N-dimethylformamide (20%, v/v) and stirred until the starting material was no longer observed by HPLC/TLC analysis. The mixture was diluted with ethyl acetate and washed with water. The organic phase was dried over anhydrous sodium sulfate, filtered and concentrated. The desired appropriately substituted 2,2,2-trichloro-1-[10-(4-aminobenzoyl)-10,11-dihydro-5H-pyrrolo[2,1-c][1,4]benzodiazepin-3-yl}-ethanone was isolated by flash chromatography (Biotage, Flash 40M, gradient elution Of 20–30% ethyl acetate in hexanes).

Step C. An appropriately substituted 1,4-diketone (25 mmol) was added to a vial containing an appropriately substituted aniline of Step B (4.4 mmol) followed by the addition of acetic acid (1 mL). The contents of the vial were stirred and heated (80° C.) without the vial capped (to allow for the removal of water). After 1 hour the solution was diluted with ethyl acetate (20 mL). The organic phase was washed with water, aqueous sodium bicarbonate and brine. The organic layer was dried over anhydrous sodium sulfate, filtered and concentrated. The resulting residue was purified by flash column chromatography to afford the desired appropriately substituted 2,2,2-trichloro-1-{10-{4-(1H-pyrrol-1-yl)-benzoyl]-10,11-dihydro[2,1-c][1,4]benzodiazepin-3-yl}-ethanone.

Step D. The material from Step C (3.85 mmol) was dissolved in tetrahydrofuran (10 mL) and treated with aqueous sodium hydroxide (2 N, 3 mL). The mixture was allowed to stir with heating (80° C.) overnight. After cooling to room temperature, aqueous hydrochloric acid (2 N, 3.2 mL) was added and product was recovered by extraction with ethyl acetate. The combined extracts were evaporated and the residue purified by flash column chromatography, eluting with a gradient of 20 to 50% ethyl acetate in hexanes to provide the desired appropriately substituted title compound.

EXAMPLE 52

{10-[4-(2,5-Dimethyl-1H-pyrrol-1-yl)-3-methoxybenzoyl]-10,11-dihydro-5H-pyrrolo[2,1-c][1,4]benzodiazepin-3-yl}[4-(2-hydroxyethyl)-1-piperazinyl]methanone HRMS [(+)ESI, m/z]: 568.29191 $[M+H]^+$. Calcd. for $C_{33}H_{38}N_5O_4$ 568.29184

What is claimed:

1. A compound of the formula:

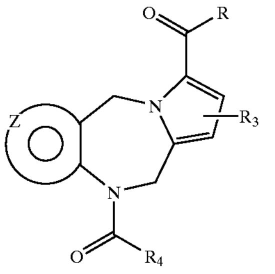

(I)

wherein:

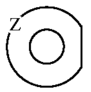

is selected from the moieties:

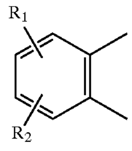

or

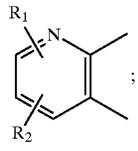

;

$R_1$ and $R_2$ are, independently, hydrogen, $(C_1-C_6)$ lower alkyl, halogen, cyano, trifluoromethyl, hydroxy, amino, $(C_1-C_6)$ lower alkylamino, $(C_1-C_6)$ lower alkoxy, —$OCF_3$, $(C_1-C_6)$ lower alkoxycarbonyl, —NHCO $[(C_1-C_6)$lower alkyl], carboxy, —$CONH_2$, —CONH $[(C_1-C_6)$ lower alkyl] or —$CON[(C_1-C_6)$ lower alkyl$]_2$;

$R_3$ is hydrogen, $(C_1-C_6)$ lower alkyl, $(C_1-C_6)$ lower alkoxy, hydroxy, amino, $(C_1-C_6)$ lower alkylamino, —CO lower alkyl $(C_1-C_6)$, or halogen;

$R_4$ consists of the moiety B—C; wherein:

B is:

(a)

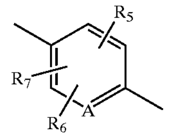

or (b)

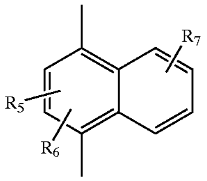

and C is selected from any of the following groups:

(c)

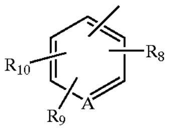

(d)

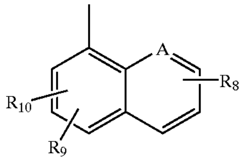

(e)

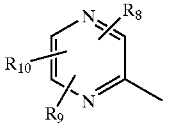

(f)

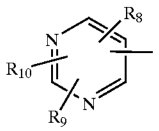

or (g)

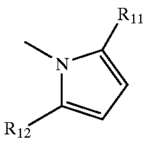

wherein:

A is CH or N;

$R_5$, $R_6$, $R_7$, $R_8$, $R_9$, $R_{10}$ are, independently, hydrogen, $(C_1-C_6)$ lower alkyl, $(C_1-C_6)$ lower alkoxy, hydroxy $(C_1-C_6)$ lower alkyl, alkoxy , $(C_1-C_6)$ lower alkyl, alkoxy, $(C_1-C_6)$ lower alkyl, $(C_1-C_6)$ lower alkylcarbonyl, $(C_3-C_6)$ lower alkenyl, $(C_3-C_6)$ lower alkynyl, $(C_3-C_8)$ cycloalkyl, formyl, cycloalkylcarbonyl, carboxy, lower alkoxycarbonyl, cycloalkyloxycarbonyl, aryl alkyloxycarbonyl, carbamoyl, —O—$CH_2$—CH=$CH_2$, halogen, halo lower alkyl, trifluoromethyl, —$OCF_3$, —$S[(C_1-C_6)$ lower alkyl], —$OC(O)N[(C_1-C_6)$ lower alkyl$]_2$, —$CONH[(C_1-C_6)$ lower alkyl], —$CON[(C_1-C_6)$ lower alkyl$]_2$, $(C_1-C_6)$ lower alkyl]amino, di-$[(C_1-C_6)$ lower alkylamino, $(C_1-C_6)$ lower alkyl di-$[(C_1-C_6)$ lower alkyl]amino, hydroxy, cyano, trifluoromethylthio, nitro, amino, ($C_1$–$C_6$) lower alkylsulfonyl, aminosulfonyl, ($C_1$–$C_6$) lower alkylaminosulfonyl,

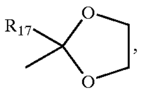

phenyl or naphthyl;

$R_{11}$ and $R_{12}$ are, independently, hydrogen, ($C_1$–$C_6$) lower alkyl, ($C_3$–$C_6$) lower alkenyl, ($C_1$–$C_6$) lower alkynyl, cyclo lower alkyl, or aryl, optionally substituted by hydroxy, ($C_1$–$C_6$) lower alkyl, ($C_1$–$C_6$) lower alkoxy, halogen, cyano, —$SO_2$[($C_1$–$C_6$) lower alkyl], or —S[($C_1$–$C_6$) lower alkyl];

R is selected from any of the following groups:

(g)

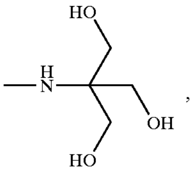

(h)

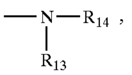

(i)

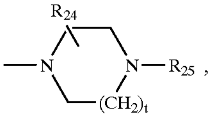

(j)

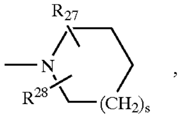

(k)

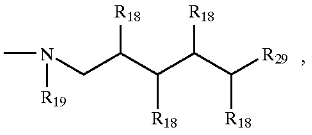

(l)

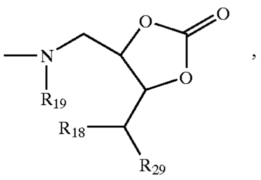

(m)

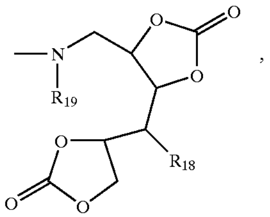

-continued (n)

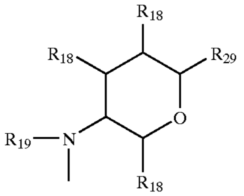

or (o)

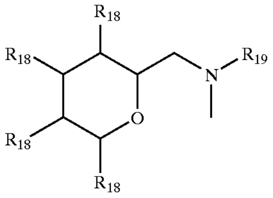

wherein:

$R_{13}$ is hydrogen, ($C_1$–$C_6$) lower alkyl, ($C_7$–$C_{12}$) aryl lower alkyl wherein the aryl moiety is optionally substituted with lower alkoxy, or any of the following groups:

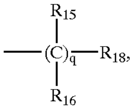

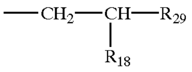

or

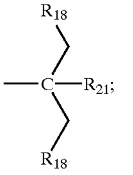

$R_{14}$ is selected from any of the following groups:

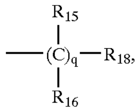

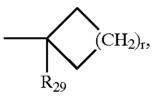

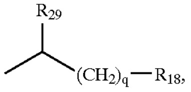

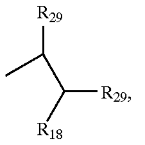

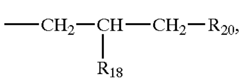

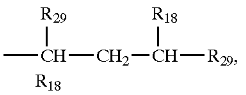

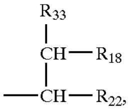

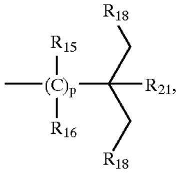

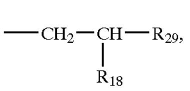

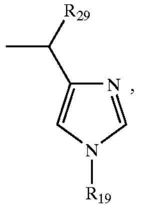

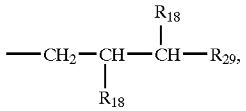

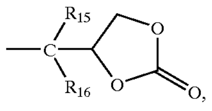

-continued

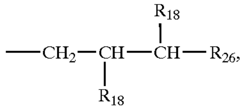

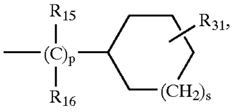

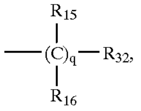

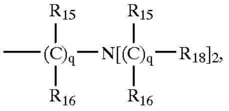

or

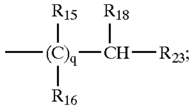

$R_{15}$ and $R_{16}$ are, independently, hydrogen, $(C_1-C_6)$ lower alkyl or $(C_7-C_{12})$ aryl lower alkyl;

$R_{17}$ is hydrogen, or $(C_1-C_6)$ lower alkyl;

$R_{18}$ is hydroxy, lower alkoxy, or OP wherein P is a hydroxy protecting group;

$R_{19}$ is hydrogen, $(C_1-C_6)$ lower alkyl or $(C_7-C_{12})$ aryl lower alkyl;

$R_{20}$ is —N[lower alkyl]$_2$, —N[aryl lower alkyl]$_2$,

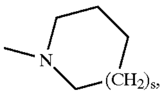

or

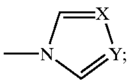

$R_{21}$ is hydrogen, $(C_1-C_6)$ lower alkyl, or $R_{29}$;

$R_{22}$ is $(C_1-C_6)$ lower alkyl, —COR$_{18}$, —CONH[lower alkyl], or —CON[lower alkyl]$_2$;

$R_{23}$ is aryl, optionally substituted by one to three substituents chosen from hydroxy, $(C_1-C_6)$ lower alkoxy, aryloxy lower alkyl, or halogen;

$R_{24}$ represents one to four substituents chosen, independently, from the group of hydrogen or $(C_1-C_6)$ lower alkyl;

$R_{25}$ is selected from any of the following groups:

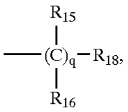

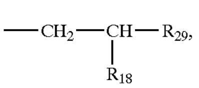

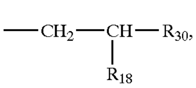

or

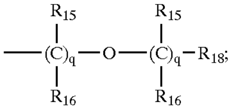

$R_{26}$ is $(C_1-C_6)$ lower alkyl, or aryl $(C_1-C_6)$ lower alkyl;

$R_{27}$ and $R_{28}$ taken together represent one to four substituents chosen, independently, from the group of $R_{18}$, $R_{29}$, $(C_1-C_6)$ lower alkyl, $[(C_1-C_6)$ lower alkyl$]_2$, —CONH [lower alkyl], —CON[lower alkyl]$_2$, $R_{32}$,

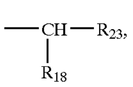

or

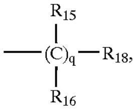

with the proviso that at least one substituent is not $(C_1-C_6)$ lower alkyl, —$[C_1-C_6)$ lower alkyl$]_2$, —CONH[lower alkyl] or —CON[lower alkyl]$_2$; and with further proviso that $R_{27}$ and $R_{28}$ can be joined together to form a 5 or 6 membered saturated ring optionally substituted by one or more substituents selected from $R_{18}$ or $R_{29}$;

$R_{29}$ is selected from the group of hydroxy lower alkyl, lower alkoxy lower alkyl, or lower alkyl OP wherein P is a hydroxy protecting group;

$R_{30}$ is $(C_1-C_6)$ lower alkyl, or $(C_7-C_{12})$ aryl lower alkyl;

$R_{31}$ represents one to four substituents chosen from the group of $R_{18}$ or $R_{29}$;

$R_{32}$ is

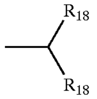

or

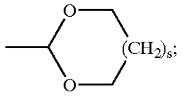

$R_{33}$ is hydrogen or $(C_1-C_6)$ lower alkyl;

X and Y are either CH, or N;

p is an integer from 0 to 1;

q is an integer from 2 to 4;

r is an integer from 0 to 3;

s in integer from 0 to 2; and t is an integer from 1 to 2;

or a pharmaceutically acceptable salt thereof.

2. A compound of claim 1, wherein R is selected, independently, from the groups:

(g)

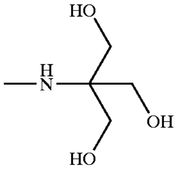

(h)

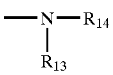

(i)

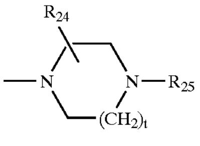

-continued (k)

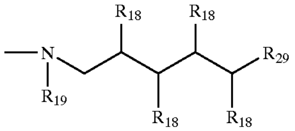

or (m)

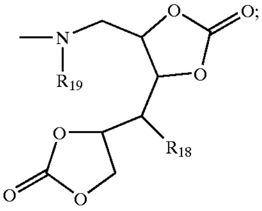

and $R_{14}$ is selected, independently from the groups:

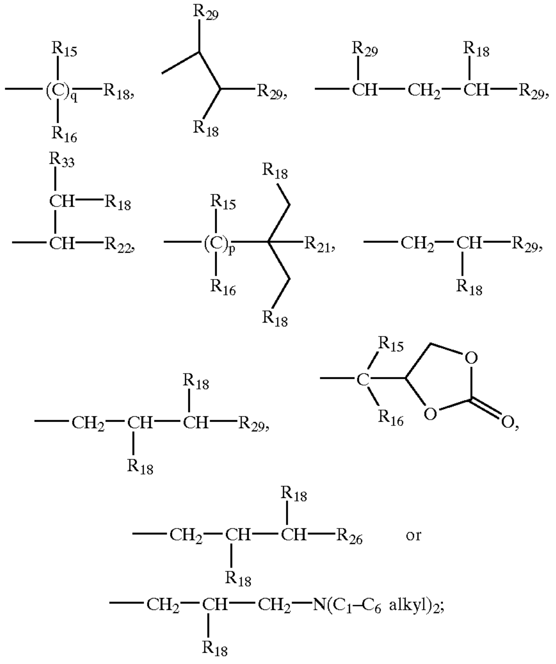

or a pharmaceutically acceptable salt thereof.

3. A compound of claim 1 having the formula:

(II)

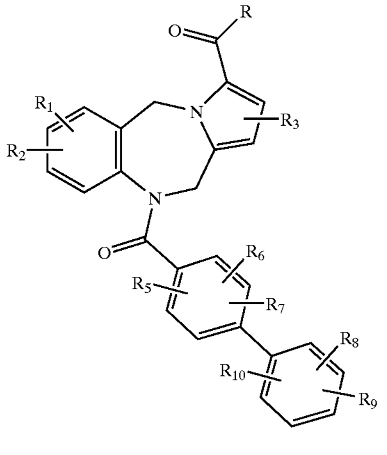

wherein R, $R_1$, $R_2$, $R_3$, $R_5$, $R_6$, $R_7$, $R_8$, $R_9$, $R_{10}$ are as defined in claim 1, or a pharmaceutically acceptable salt form thereof.

4. A compound of claim 1 of the formula:

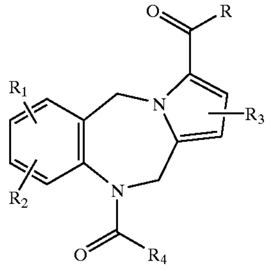

$R_1$ and $R_2$ are, independently, selected from hydrogen, $(C_1–C_6)$lower alkyl, halogen, cyano, trifluoromethyl, hydroxy, amino, $(C_1–C_6)$ lower alkylamino, $(C_1–C_6)$ lower alkoxy, $—OCF_3$, $(C_1–C_6)$ lower alkoxycarbonyl, $—NHCO[(C_1–C_6)$lower alkyl], carboxy, $—CONH_2$, $—CONH[(C_1–C_6)$ lower alkyl] or $—CON[(C_1–C_6)$ lower alkyl$]_2$;

$R_3$ is a substituent selected from hydrogen, $(C_1–C_6)$ lower alkyl, $(C_1–C_6)$ lower alkoxy, hydroxy, amino, $(C_1–C_6)$ lower alkylamino, —CO lower alkyl $(C_1–C_6)$, or halogen;

$R_4$ consists of the moiety B—C; wherein:

B is:

(a)

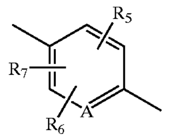

or (b)

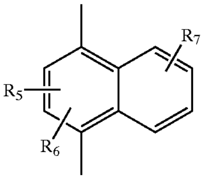

and C is:

(c)

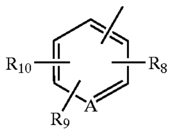

(d)

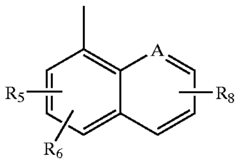

-continued (e)

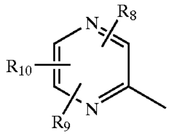

(f)

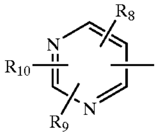

or (g)

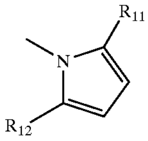

wherein:

A is CH or N;

$R_5$, $R_6$, $R_7$, $R_8$, $R_9$, $R_{10}$ are, independently, selected from hydrogen, ($C_1$–$C_6$) lower alkyl, ($C_1$–$C_6$) lower alkoxy, hydroxy($C_1$–$C_6$) lower alkyl, alkoxy($C_1$–$C_6$) lower alkyl, acyloxy($C_1$–$C_6$) lower alkyl, ($C_1$–$C_6$) lower alkylcarbonyl, ($C_3$–$C_6$) lower alkenyl, ($C_3$–$C_6$) lower alkynyl, ($C_3$–$C_8$) cycloalkyl, formyl, cycloalkylcarbonyl, carboxy, lower alkoxycarbonyl, cycloalkyloxycarbonyl, aryl alkyloxycarbonyl, carbamoyl, —O—$CH_2$—CH═$CH_2$, halogen, halo lower alkyl, trifluoromethyl, —$OCF_3$, —S[($C_1$–$C_6$) lower alkyl], —OC(O)N[($C_1$–$C_6$) lower alkyl]$_2$, —CONH[($C_1$–$C_6$) lower alkyl], —CON[($C_1$–$C_6$) lower alkyl]$_2$, ($C_1$–$C_6$) lower alkylamino, di-[($C_1$–$C_6$) lower alkyl]amino, ($C_1$–$C_6$) lower alkyl di-[($C_1$–$C_6$) lower alkyl]amino, hydroxy, cyano, trifluoromethylthio, nitro, amino, ($C_1$–$C_6$) lower alkylsulfonyl, aminosulfonyl, ($C_1$–$C_6$) lower alkylaminosulfonyl,

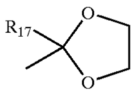

, phenyl or naphthyl;

$R_{11}$ and $R_{12}$ are, independently, selected from the group of hydrogen, ($C_1$–$C_6$) lower alkyl, ($C_3$–$C_6$) lower alkenyl, ($C_1$–$C_6$) lower alkynyl, cyclo lower alkyl, or aryl, optionally substituted by hydroxy, ($C_1$–$C_6$) lower alkyl, ($C_1$–$C_6$) lower alkoxy, halogen, cyano, —$SO_2$[($C_1$–$C_6$) lower alkyl], or —S[($C_1$–$C_6$) lower alkyl];

R is selected, independently, from the groups:

(g)

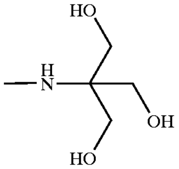

-continued (h)

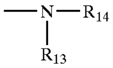

(i)

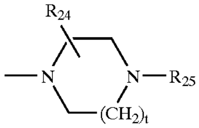

(k)

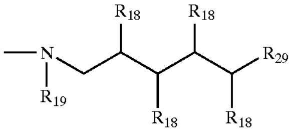

or (m)

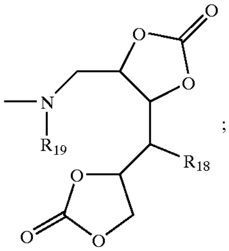

;

$R_{13}$ is selected from hydrogen, ($C_1$–$C_6$) lower alkyl, ($C_7$–$C_{12}$) aryl lower alkyl wherein the aryl moiety is optionally substituted with lower alkoxy, or any of the following groups:

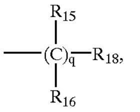

,

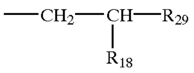

or

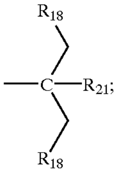

;

$R_{14}$ is selected from the groups:

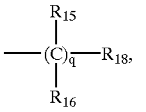

,

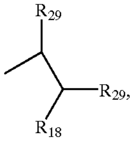

,

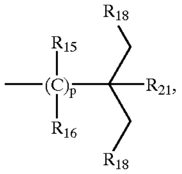

,

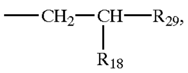

,

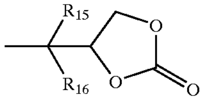

or

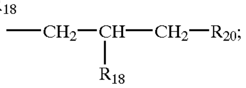

;

$R_{15}$ and $R_{16}$ are, independently, chosen from the group of hydrogen, ($C_1$–$C_6$) lower alkyl or ($C_7$–$C_{12}$) aryl lower alkyl;

$R_{18}$ is hydroxy, lower alkoxy, or OP wherein P is a hydroxy protecting group;

$R_{19}$ is selected from the group of hydrogen, ($C_1$–$C_6$) lower alkyl or ($C_7$–$C_{12}$) aryl lower alkyl;

$R_{21}$ is hydrogen, ($C_1$–$C_6$) lower alkyl, or $R_{29}$;

$R_{25}$ is selected from the groups:

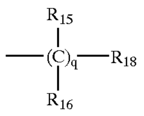
or
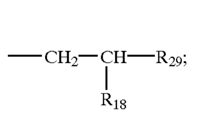

$R_{26}$ is ($C_1$–$C_6$) lower alkyl, or aryl ($C_1$–$C_6$) lower alkyl;

$R_{29}$ is selected from the group of hydroxy lower alkyl, lower alkoxy lower alkyl, or lower alkyl OP wherein P is a hydroxy protecting group;

p is an integer from 0 to 1;

q is an integer from 2 to 4;

t is an integer from 1 to 2;

or a pharmaceutically acceptable salt thereof.

5. A compound of claim 1 selected from the group of:

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid bis-(2-hydroxy-ethyl)-amide;

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid (2,3-dihydroxy-propyl)-methyl-amide;

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid (2-hydroxy-1,1-bis-hydroxymethyl-ethyl)-amide;

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid methyl-((2S,3R,4R,5R)-2,3,4,5,6-pentahydroxy-hexyl)-amide;

(2S)-3-{4-[(10-{[2-Methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}propane-1,2-diol;

(2R)-3-{4-[(10-{[2-Methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}propane-1,2-diol;

Methyl 2-{4-[(10-{[2-methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}ethyl ether;

(2R)-1-Methoxy-3-{4-[(10-{[2-methyl-2'-trifluoromethyl-[1,1'-biphenyl]-4-yl]carbonyl}-10,11-dihydro-5H-pyrrolo[2,1-c][1,4]benzodiazepin-3-yl)carbonyl]piperazin-1-yl}propan-2-ol;

[3-({4-[(2S)-2-Hydroxy-3-methoxypropyl]-1-piperazinyl}carbonyl)-5H-pyrrolo[2,1-c][1,4]benzodiazepin-10(11H)-yl][2-methyl-2'-trifluoromethyl-[1,1'-biphenyl]-4-yl]methanone; or N-(2,3-Dimethoxypropyl)-N-methyl-10-{[2-methyl-2'-trifluoromethyl-[1,1'-biphenyl]-4-yl]carbonyl}-10,11-dihydro-5H-pyrrolo[2,1-c][1,4]benzodiazepine-3-carboxamide; or a pharmaceutically acceptable salt form thereof.

6. A compound of claim 1 selected from the group of:

10-[(2-Methyl-2'-trifluoromethyl-[1,1'-biphenyl]-4-yl)carbonyl]-10,11-dihydro-5H-pyrrolo[2,1-c][1,4]benzodiazepine-3-carboxylic acid methyl-[(2-oxo-[1,3]dioxolan-4-yl)methyl]-amide;

N-[((4S,5S)-5-{(R)-Hydroxy[(4R)-2-oxo-1,3-dioxolan-4-yl]methyl}-2-oxo-1,3-dioxolan-4-yl)methyl]-N-methyl-10-{[2-methyl-2'-trifluoromethyl-[1,1'-biphenyl]-4-yl]carbonyl}-10,11-dihydro-5H-pyrrolo[2,1-c]benzodiazepine-3-carboxamide;

2-(Acetyloxy)-1-({methyl[(10-{[2-methyl-2'-trifluoromethyl-[1,1'-biphenyl]-4-yl]carbonyl}-10,11-dihydro-5H-pyrrolo[2,1-c][1,4]benzodiazepin-3-yl)carbonyl]amino}methyl)ethyl acetate;

10-[(2'-Methoxy-2-methyl-[1,1'-biphenyl]-4-yl)carbonyl]-10,11-dihydro-5H-pyrrolo[2,1-c][1,4]benzodiazepine-3-carboxylic acid (2,3-dihydroxy-propyl)-methyl-amide;

N-[(2S)-2,3-Dihydroxypropyl]-10-[(2'-methoxy-2-methyl-[1,1'-biphenyl]-4-yl)carbonyl]-N-methyl-10,11-dihydro-5H-pyrrolo[2,1-c][1,4]benzodiazepine-3-carboxamide;

N-[(2R)-2,3-Dihydroxypropyl]-10-[(2'-methoxy-2-methyl-[1,1'-biphenyl]-4-yl)carbonyl]-N-methyl-10,11-dihydro-5H-pyrrolo[2,1-c][1,4]benzodiazepine-3-carboxamide;

10-[(2'-Methoxy-2-methyl-[1,1'-biphenyl]-4-yl)carbonyl]-10,11-dihydro-5H-pyrrolo[2,1-c][1,4]benzodiazepine-3-carboxylic acid methyl-[(2S,3R,4R,5R)-2,3,4,5,6-pentahydroxy-hexyl)-amide;

N-(2,3-Dihydroxypropyl)-7,8-dimethoxy-N-methyl-10-{[2-methyl-2'-trifluoromethyl-[1,1'-biphenyl]-4-yl]carbonyl}-10,11-dihydro-5H-pyrrolo[2,1-c][1,4]benzodiazepine-3-carboxamide;

N,N-Bis(2-hydroxyethyl)-7,8-dimethoxy-10-{[2-methyl-2'-trifluoromethyl-[1,1'-biphenyl]-4-yl]carbonyl}-10,11-dihydro-5H-pyrrolo[2,1-c][1,4]benzodiazepine-3-carboxamide; or 10-{[6-Chloro-3-methoxy-2'-trifluoromethyl-[1,1'-biphenyl]-4-yl]carbonyl}-N-methyl-N-[(2S,3R,4R,5R)-2,3,4,5,6-pentahydroxy-hexyl]-10,11-dihydro-5H-pyrrolo[2,1-c][1,4]benzodiazepine-3-carboxamide;

or a pharmaceutically acceptable salt form thereof.

7. A compound of claim 1 selected from the group of:

N-(2,3-Dihydroxypropyl)-10-{[2-methoxy-2'-trifluoromethyl-[1,1'-biphenyl]-4-yl]carbonyl}-N-methyl-10,11-dihydro-5H-pyrrolo[2,1-c][1,4]benzodiazepine-3-carboxamide;

N-[(3-Dimethylamino)-2-hydroxy-propyl]-10-{[2-methoxy-2'-trifluoromethyl-[1,1'-biphenyl]-4-yl]carbonyl}-N-methyl-10,11-dihydro-5H-pyrrolo[2,1-c][1,4]benzodiazepine-3-carboxamide;

10-{[2-Methoxy-2'-trifluoromethyl-[1,1'-biphenyl]-4-yl]carbonyl}-N-methyl-N-[(2R,3S,4R,5S)-2,3,4,5,6-pentahydroxy-hexyl]-10,11-dihydro-5H-pyrrolo[2,1-c][1,4]benzodiazepine-3-carboxamide;

10-[4-(Naphthalen-1-yl)benzoyl]-10,11-dihydro-5H-pyrrolo[2,1-c][1,4]benzodiazepine-3-carboxylic acid bis-(2-hydroxy-ethyl)-amide;

2-{4-[10-{[2-Chloro-4-(naphthalen-1-yl)phenyl]carbonyl}-(10,11-dihydro-5H-pyrrolo[2,1-c][1,4]benzodiazepin-3-yl)carbonyl]piperazine-1-yl}-1-hydroxyethane;

10-{[4-(4-Methyl-naphthalen-1-yl)phenyl]carbonyl}-10,11-dihydro-5H-pyrrolo[2,1-c][1,4]benzodiazepine-3-carboxylic acid (2,3-dihydroxy-propyl)-N-methylamide;

10-[(3-Methoxy-2'-methyl-[1,1'-biphenyl]-4-yl)carbonyl]-10,11-dihydro-5H-pyrrolo[2,1-c][1,4]benzodiazepine-3-carboxylic acid methyl-[(2S, 3R, 4R, 5R)-2,3,4,5,6-pentahydroxy-hexyl]-amide;

{10-[(2'-Chloro-6-chloro-3-methoxy-[1,1'-biphenyl]-4-yl)carbonyl]-10,11-dihydro-5H-pyrrolo[2,1-c][1,4]benzodiazepine-3-yl}[(2S, 5S)-bis-hydroxymethyl-(3R, 4R)-bis-hydroxy-pyrrolidin-1-yl]-methanone;

10-[(6-Chloro-2'-ethoxy-3-methoxy-[1,1'-biphenyl]-4-yl)carbonyl]-N-methyl-10,11-dihydro-5H-pyrrolo[2,1-c][1,4]benzodiazepine-3-carboxylic acid methyl-(2,3,4-trihydroxybutyl)-amide; or N-(2,3-Dihydroxy-propyl)-N-(2,3,4-trihydroxy-butyl)-10-{[6-chloro-2'-fluoro-3-methoxy-[1,1'-biphenyl]-4-yl]carbonyl}-10,11-dihydro-5H-pyrrolo[2,1-c][1,4]benzodiazepine-3-carboxamide;

or a pharmaceutically acceptable salt form thereof.

8. A compound of claim 1 selected from the group of:

N-Methyl-N-(2-hydroxy-1,1-bis-hydroxymethyl-ethyl)-{[10-(2-methoxy)-2'-methoxy-[1,1'-biphenyl]-4-yl]carbonyl}-10,11-dihydro-5H-pyrrolo[2,1-c][1,4]benzodiazepin-3-carboxamide;

N-(2-Hydroxy-ethyl)-N-(2',3',4'-trihydroxy-butyl)-10-[(3,6-dimethoxy-2'-trifluoromethyl-[1,1'-biphenyl]-4-yl)carbonyl]-10,11-dihydro-5H-pyrrolo[2,1-c][1,4]benzodiazepine-3-carboxamide;

N-(2,3-Dihydroxy-propyl)-N-(1-hydroxymethyl-2,3-dihydroxy-propyl)-10-{[3-methyl-4-(4-pyridinyl)phenyl]carbonyl}-10,11-dihydro-5H-pyrrolo[2,1-c][1,4]benzodiazepine-3-carboxamide;

10-[(6-Phenyl-pyridin-3-yl)-carbonyl]-10,11-dihydro-5H-pyrrolo[2,1-c][1,4]benzodiazepine-3-carboxylic acid bis-(2-hydroxy-ethyl)-amide;

10-{[6-(Naphthalen-1-yl)-pyridin-3-yl]-carbonyl}-N-methyl-N-[(2S,3R,4R,5R)-2,3,4,5,6-pentahydroxy-hexyl]-10,11-dihydro-5H-pyrrolo[2,1-c][1,4]benzodiazepine-3-carboxamide;

{(2S)-1-[(10-{[2-Methoxy-2'(trifluoromethyl)[1,1'-biphenyl]-4-yl]carbonyl}-10,11-dihydro-5H-pyrrolo[2,1-c][1,4]benzodiazepin-3-yl)carbonyl]pyrrolidin-2-yl}-methanol;

7,8-Dimethoxy-10-[(2'-methoxy-2-methyl-[1,1'-biphenyl]-4-yl)carbonyl]-10,11-dihydro-5H-pyrrolo[2,1-c][1,4]benzodiazepine-3-carboxylic acid methyl-[(2S,3R,4R,5R)-2,3,4,5,6-pentahydroxy-hexyl)-amide;

9-[(2-Methyl-2'-trifluoromethyl-[1,1'-biphenyl]-4-yl)carbonyl]-9,10-dihydro-4H-3a,5,9-triaza-benzo[f]azulene-3-carboxylix acid (3-hydroxy-propyl)amide;

{10-[(6-Chloro-3-methoxy-2'-methyl-[1,1'-biphenyl]-4-yl)carbonyl]-10,11-dihydro-5H-pyrrolo[2,1-c][1,4]benzodiazepin-3-yl}[4-(2-hydroxyethyl)-1-piperazinyl]methanone; or

[4-(2-Hydroxyethyl)-1-piperazinyl]{10-[(2'-methoxy-2-methyl-[1,1'-biphenyl]-4-yl)carbonyl]-10,11-dihydro-5H-pyrrolo[2,1-c][1,4]benzodiazepin-3-yl}methanone;

or a pharmaceutically acceptable salt form thereof.

9. A compound of claim 1 selected from the group of:

[4-(2-Hydroxyethyl)-1-piperazinyl]{10-[3-methoxy-4-(1-naphthyl)benzoyl]-10,11-dihydro-5H-pyrrolo[2,1-c][1,4]benzodiazepin-3-yl}methanone;

[4-(2-Hydroxyethyl)-1-piperazinyl]{110-[(2-methoxy-2'-methyl[1,1'-biphenyl]-4-yl)carbonyl]-10,11-dihydro-5H-pyrrolo[2,1-c][1,4]benzodiazepin-3-yl}methanone;

{10-[(2,2'-Dimethoxy[1,1'-biphenyl]-4-yl)carbonyl]-10,11-dihydro-5H-pyrrolo[2,1-c][1,4]benzodiazepin-3-yl}[4-(2-hydroxyethyl)-1-piperazinyl]methanone;

[4-(2-Hydroxyethyl)-1-piperazinyl]{10-[(3'-methoxy-2-methyl-[1,1'-biphenyl]-4-yl)carbonyl]-10,11-dihydro-5H-pyrrolo[2,1-c][1,4]benzodiazepin-3-yl}methanone;

[4-(2-Hydroxyethyl)-1-piperazinyl]{10-[(2'-methyl-[1,1'-biphenyl]-4-yl)carbonyl]-10,11-dihydro-5H-pyrrolo[2,1-c][1,4]benzodiazepin-3-yl}methanone;

{10-[(2,2'-Dimethyl-[1,1'-biphenyl]-4-yl)carbonyl]-10,11-dihydro-5H-pyrrolo[2,1-c][1,4]benzodiazepin-3-yl}[4-(2-hydroxyethyl)-1-piperazinyl]methanone;

[4-(2-Hydroxyethyl)-1-piperazinyl]{10-[(2'-methoxy-[1,1'-biphenyl]-4-yl)carbonyl]-10,11-dihydro-5H-pyrrolo[2,1-c][1,4]benzodiazepin-3-yl}methanone;

[4-(2-Hydroxyethyl)-1-piperazinyl](10-{[2-methyl-2'-trifluoromethyl-[1,1'-biphenyl]-4-yl)carbonyl}-10,11-dihydro-5H-pyrrolo[2,1-c][1,4]benzodiazepin-3-yl)methanone;

{10-[(6-Chloro-3,3'-dimethoxy-[1,1'-biphenyl]-4-yl)carbonyl]-10,11-dihydro-5H-pyrrolo[2,1-c][1,4]benzodiazepin-3-yl}[4-(2-hydroxyethyl)-1-piperazinyl]methanone;

{10-[(2,3'-Dimethoxy[1,1'-biphenyl]-4-yl)carbonyl]-10,11-dihydro-5H-pyrrolo[2,1-c][1,4]benzodiazepin-3-yl}[4-(2-hydroxyethyl)-1-piperazinyl]methanone;

10-(3-Methoxy-4-pyridin-3-yl-benzoyl)-10,11-dihydro-5H-pyrrolo[1,2-c][1,4]benzodiazepin-3-carboxylic acid (2,3-dihydroxy-propyl)-methyl-amide; or {10-[4-(2,5-Dimethyl-1H-pyrrol-1-yl)-3-methoxybenzoyl]-10,11-dihydro-5H-pyrrolo[2,1-c][1,4]benzodiazepin-3-yl}[4-(2-hydroxyethyl)-1-piperazinyl]methanone or a pharmaceutically acceptable salt form thereof.

10. A pharmaceutical composition comprising a pharmaceutically effective amount of a compound of claim 1, or a pharmaceutically acceptable salt form thereof, and a pharmaceutically acceptable carrier or excipient.

11. A method for inhibiting or preventing preterm labor, dysmenorrhea, or endometritis in a mammal, the method comprising administering to a mammal in need thereof a pharmaceutically effective amount of a compound of claim 1, a pharmaceutically acceptable salt form thereof.

12. A method comprising contacting an oxytocin receptor with a compound of claim 1.

13. A method of antagonizing the oxytocin receptor in a mammal comprising providing to the mammal an effective amount of a compound of claim 1.

14. A method comprising contacting a vasopressin receptor with a compound of claim 1.

15. A method of antagonizing the vasopressin receptor in a mammal comprising providing to the mammal an effective amount of a compound of claim 1.

* * * * *